(12) United States Patent
Zhu et al.

(10) Patent No.: US 7,622,491 B2
(45) Date of Patent: Nov. 24, 2009

(54) MODULATORS OF PPAR AND METHODS OF THEIR PREPARATION

(75) Inventors: Yan Zhu, Foster City, CA (US); Jingyuan Ma, Fremont, CA (US); Peng Cheng, Union City, CA (US); Zuchun Zhao, Pleasanton, CA (US); Francine M. Gregoire, Lafayette, CA (US); Vera A. Rakhmanova, Foster City, CA (US)

(73) Assignee: Metabolex Inc., Hayward, CA (US)

( * ) Notice: Subject to any disclaimer, the term of this patent is extended or adjusted under 35 U.S.C. 154(b) by 281 days.

(21) Appl. No.: 11/202,963

(22) Filed: Aug. 11, 2005

(65) Prior Publication Data

US 2006/0058301 A1    Mar. 16, 2006

Related U.S. Application Data

(60) Provisional application No. 60/601,305, filed on Aug. 13, 2004.

(51) Int. Cl.
*A61K 31/40* (2006.01)
*A61K 31/415* (2006.01)
*C07D 207/00* (2006.01)
*C07D 231/00* (2006.01)
*C07D 233/00* (2006.01)

(52) U.S. Cl. .............. 514/385; 514/403; 514/408; 548/215; 548/255; 548/300.1; 548/356.1; 548/400

(58) Field of Classification Search ............... 548/255, 548/215
See application file for complete search history.

(56) References Cited

U.S. PATENT DOCUMENTS 7,323,480 B2 *   1/2008   Zhu et al. ................. 514/359

* cited by examiner

*Primary Examiner*—Golam M. M. Shameem
*Assistant Examiner*—Susannah Chung
(74) *Attorney, Agent, or Firm*—Townsend and Townsend and Crew LLP

(57) ABSTRACT

The present invention is directed to certain novel compounds represented by Formula (I) and pharmaceutically acceptable salts, solvates, hydrates and prodrugs thereof. The present invention is also directed to methods of making and using such compounds and pharmaceutical compositions containing such compounds to treat or control a number of diseases mediated by PPAR such as glucose metabolism, lipid metabolism and insulin secretion, specifically Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity and eating disorders.

57 Claims, 12 Drawing Sheets

MODULATORS OF PPAR AND METHODS OF THEIR PREPARATION

CROSS-REFERENCES TO RELATED APPLICATIONS

This application claims benefit of priority under 35 U.S.C. §119(e) to U.S. Provisional Application Ser. No. 60/601,305 filed Aug. 13, 2004, which is herein incorporated by reference in its entirety.

BACKGROUND OF THE INVENTION

Peroxisome Proliferator-Activated Receptors (PPARs) are implicated in a number of biological processes and disease states including Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity, eating disorders and suppressing appetite.

Diabetes, Hyperinsulinemia, Hypertriglyceridemia, Hyperglycemia, Atherosclerosis and Cardiovascular Disease Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996) and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease, coronary heart disease and other cardiovascular diseases. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as non-insulin dependent diabetes or NIDDM).

Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β-cells of the pancreas; and Idiopathic Diabetes Mellitus, which refers to forms of the disease that have no known etiologies.

Type 2 diabetes is a complex disease characterized by defects in glucose and lipid metabolism. Typically there are perturbations in many metabolic parameters including increases in fasting plasma glucose levels, free fatty acid levels and triglyceride levels (hypertriglyceridemia), as well as a decrease in the ratio of HDL/LDL. One of the principal underlying causes of diabetes is thought to be when muscle, fat and liver cells fail to respond to normal concentrations of insulin (insulin resistance). Insulin resistance may be due to reduced numbers of insulin receptors on these cells or a dysfunction of signaling pathways within the cells or both. Insulin resistance is characteristically accompanied by a relative, rather than absolute, insulin deficiency. Type 2 diabetes can range from predominant insulin resistance with relative insulin deficiency to predominant insulin deficiency with some insulin resistance.

The beta cells in insulin resistant individuals initially compensate for this insulin resistance by secreting abnormally high amounts of insulin (hyperinsulinemia). Over time, these cells become unable to produce enough insulin to maintain normal glucose levels, indicating progression to Type 2 diabetes. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased. Consequently, in Type 2 diabetics, adipose tissue mass is often increased.

Type 2 diabetes is brought on by a combination of genetic and acquired risk factors—including a high-fat diet, lack of exercise and aging. Worldwide, Type 2 diabetes has become an epidemic, driven by increases in obesity and a sedentary lifestyle, widespread adoption of western dietary habits and the general aging of the population in many countries. In 1985, an estimated 30 million people worldwide had diabetes—by 2000, this figure had increased 5-fold, to an estimated 154 million people. The number of people with diabetes is expected to double between now and 2025, to about 300 million.

Therapies aimed at reducing peripheral insulin resistance are available. The most relevant to this invention are drugs of the thiazolidinedione (TZD) class namely troglitazone, pioglitazone and rosiglitazone. In the US these have been marketed under the names Rezulin™, Avandia™ and Actos™, respectively. The principal effect of these drugs is to improve glucose homeostasis. Notably in diabetics treated with TZDs there are increases in peripheral glucose disposal rates indicative of increased insulin sensitivity in both muscle and fat. Treatment of diabetes also improves Islet (of Langerhans) function, specifically, insulin secretion, islet architecture, beta cell mass and the like.

Premature development of atherosclerosis and increased rate of cardiovascular and peripheral vascular diseases are characteristic features of patients with diabetes, with hyperlipidemia being an important precipitating factor for these diseases.

Hyperlipidemia

Hyperlipidemia is a condition generally characterized by an abnormal increase in serum lipids in the bloodstream and, as noted above, is an important risk factor in developing atherosclerosis and coronary heart disease. For a review of disorders of lipid metabolism, see, e.g., Wilson, J. et al., (ed.), *Disorders of Lipid Metabolism*, Chapter 23, Textbook of Endocrinology, 9th Edition, (W.B. Sanders Company, Philadelphia, Pa. U.S.A. 1998; this reference and all references cited therein are herein incorporated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs and dietary factors. Alternatively, hyperlipidemia can result from both a combination of primary and secondary causes of hyperlipidemia.

Hypercholesterolemia

Hypercholesterolemia, a form of hyperlipidemia, is characterized by excessive high levels of blood cholesterol. The blood cholesterol pool is generally dependant on dietary uptake of cholesterol from the intestine and biosynthesis of cholesterol throughout the body, especially the liver. The majority of the cholesterol in plasma is carried on apolipoprotein B-containing lipoproteins, such as the very-low-density lipoproteins (VLDL), low-density lipoproteins (LDL), intermediate density lipoproteins (IDL) and high density lipoproteins (HDL). Hypercholesterolemia is characterized by elevated LDL cholesterol levels. The risk of coronary artery disease in man increases when LDL and VLDL levels increase. Conversely, high HDL levels are protective against coronary artery disease (see Gordon, D. and Rifkind, B. *N. Engl. J. Med.* 1989 321: 1311-15; and Stein, O and Stein, Y. *Atherosclerosis* 1999 144: 285-303). Therefore, although it is desirable to lower elevated levels of LDL, it is also desirable to increase HDL levels.

Initial treatment for hypercholesterolemia is to place the patients on a low fat/low cholesterol diet coupled with adequate physical exercise, followed by drug therapy when LDL-lowering goals are not met by diet and exercise alone. HMG-CoA reductase inhibitors (statins) are useful for treating conditions associated with high LDL levels. Other important anti-lipidemia drugs include fibrates such as gemfibril and clofibrate, bile acid sequestrant such as cholestyramine and colestipol, probucol and nicotinic acid analogs.

Elevated cholesterol levels are in turn associated with a number of disease states, including coronary artery disease, angina pectoris, carotid artery disease, strokes, cerebral arteriosclerosis and xanthoma.

Dyslipidemia

Dyslipidemia or abnormal levels of lipoproteins in blood plasma, is a frequent occurrence among diabetics and has been shown to be one of the main contributors to the increased incidence of coronary events and deaths among diabetic subjects (see, e.g., Joslin, E. *Ann. Chim. Med.* (1927) 5: 1061-1079). Epidemiological studies since then have confirmed the association and have shown a several-fold increase in coronary deaths among diabetic subjects when compared with nondiabetic subjects (see, e.g., Garcia, M. J. et al., Diabetes (1974) 23: 105-11; and Laakso, M. and Lehto, S. *Diabetes Reviews* (1997) 5(4): 294-315). Several lipoprotein abnormalities have been described among diabetic subjects (Howard B., et al., *Atherosclerosis* (1978) 30: 153-162).

Obesity

Obesity has reached epidemic proportions globally with more than 1 billion adults overweight—at least 300 million of them clinical obese—and is a major contributor to the global burden of chronic diseases including cardiovascular disease problems, conditions associated with insulin resistance such as Type 2 diabetes and certain types of cancers. The likelihood of developing Type 2 diabetes and hypertension rises steeply with increasing body fatness. Weight reduction leads to correction of a number of obesity-associated endocrine and metabolic disorders.

Effective weight management for individuals and groups at risk of developing obesity involves a range of long term strategies. These include prevention, weight maintenance, management of co-morbidities and weight loss. Existing treatment strategies include caloric restriction programs, surgery (gastric stapling) and drug intervention. The currently available anti-obesity drugs can be divided into two classes: central acting and peripheral acting. Three marketed drugs are Xenical (Orlistat), Merida (Sibutramine) and Adipex-P (Phentermine). Xenical is a non-ic acting GI lipase inhibitor which is indicated for short and long term obesity management. Merida reduces food intake by re-uptake inhibition of primarily norepinephrine and serotonin. Adipex-P is a phenteramine with sympathomimetic activities and suppresses appetite. It is indicated only for short term use. A more drastic solution to permanent weight loss is surgery and a gastric by-pass which limits absorption of calories through massive reduction in stomach size.

Carrying extra body weight and body fat go hand and hand with the development of diabetes. People who are overweight (BMI greater than 25) are at a much greater risk of developing type 2 diabetes than normal weight individuals. Almost 90% of people with type 2 diabetes are overweight.

Syndrome X, Hyperuricemia, Eating Disorders and Suppressing Appetite

Syndrome X (including metabolic syndrome) is loosely defined as a collection of abnormalities including hyperinsulinemia, hyperuricemia, obesity, elevated levels of triglycerides, fibrinogen, small dense LDL particles and plasminogen activator inhibitor 1 (PAI-1) and decreased levels of HDL-c. These abnormalities are associated with eating disorders, particularly an overactive appetite.

PPAR

PPARs are members of the nuclear receptor superfamily of transcription factors, a large and diverse group of proteins that mediate ligand-dependent transcriptional activation and repression. They play a role in controlling expression of proteins that regulate lipid metabolism. Furthermore, the PPARs are activated by fatty acids and fatty acid metabolites. Three PPAR subtypes have been isolated: PPARα, PPARβ (also referred to as δ or NUC1) and PPARγ. Each receptor shows a different pattern of gene expression by binding to DNA sequence elements, termed PPAR response elements (PPRE). In addition, each receptor show a difference in activation by structurally diverse compounds. To date, PPREs have been identified in the enhancers of a number of genes encoding proteins that regulate lipid metabolism suggesting that PPARs play a pivotal role in the adipogenic signaling cascade and lipid homeostasis (Keller, H. and Wahli, W. *Trends Endoodn. Met.* (1993) 4:291-296. PPARα is found in the liver, heart, kidney, muscle, brown adipose tissue and gut and is involved in stimulating β-oxidation of fatty acids. PPARα is also involved in the control of cholesterol levels in rodents and in humans. Fibrates are weak PPARα agonists that are effective in the treatment of lipid disorders. In humans, they have been shown to lower plasma triglycerides and LDL cholesterol. In addition, PPARα agonists have also been reported to prevent diabetes and to improve insulin sensitivity and reduce adiposity in obese and diabetic rodents (see Koh, E. H. et al. *Diabetes* (2003) 52:2331-2337; and Guerre-Millo, M. et al. *J. Biol. Chem.* (2000) 275: 16638-16642).

PPARβ is ubiquitously expressed. Activation of PPARβ increases HDL levels in rodents and monkeys (see Oliver, W. R. et al. *PNAS* (2001) 98:5306-5311; and Leibowitz, M. D. et al. *FEBS Letters* (2000) 473:333-336). Moreover, PPARβ has been recently shown to be a key regulator of lipid catabolism and energy uncoupling in skeletal muscle cells (Dressel, U. et al. *Mol Endocrinol.* (2003) 17: 2477-2493). In rodents, activation of PPARβ induces fatty β-oxidation in skeletal muscle and adipose tissue, leading to protection against diet-induced obesity and diabetes (see Wang, Y. X. et al. *Cell* (2003) 113: 159-170; and Tanaka et al. PNAS (2003) 100:15924-15929). In human macrophages, PPARβ activation also increases the reverse cholesterol transporter ATP-binding cassette A1 and induces apolipoprotein A1-specific cholesterol efflux (see Oliver, W. R. et al. *PNAS* (2001) 98:5306-5311). Activation also increases energy expenditure.

PPAR-γ is expressed most abundantly in adipose tissue and is thought to regulate adipocyte differentiation. Drugs of the thiazolidinedione (TZD) class namely troglitazone, pioglitazone and rosiglitazone are potent and selective activators of PPAR-γ. In human, they increase insulin action, reduce serum glucose and have small but significant effects on reducing serum triglyceride levels in patients with type 2 diabetes.

Certain compounds that activate or otherwise interact with one or more of the PPARs have been implicated in the regulation of triglyceride and cholesterol levels in animal models. (See e.g., U.S. Pat. No. 5,859,501 and PCT publications WO 97/28149 and 99/04815.

Taken together, these data clearly indicate that PPARs agonists are useful in treating hypertriglyceridemia, hypercholesterolemia, obesity and type 2 diabetes.

Anti-lipidemia, anti-obesity and anti-diabetes agents are still considered to have non-uniform effectiveness, in part because of poor patient compliance due to unacceptable side effects. For Anti-lipidemia and anti-obesity agents, these side effects include diarrhea and gastrointestinal discomfort. For anti-diabetic agents, they include weight gain, edema and hepatotoxicity. Furthermore, each type of drug does not work equally well in all patients.

What is needed in the art are new compounds and methods useful for modulating peroxisome proliferators activated receptor, insulin resistance, fibrinogen levels, leptin levels, LDLc shifting LDL particle size from small dense to normal dense or large dense LDL. What is also needed in the art are new compounds and methods useful for treating Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity, eating disorders and suppressing appetite. The present invention fulfills this and other needs by providing such compounds, compositions and methods modulating peroxisome proliferators activated receptor, insulin resistance, fibrinogen levels, leptin levels, LDLc, decreasing LDL particles numbers or shifting LDL particle size from small dense to large dense LDL, increasing HDL particles numbers or shifting HDL particle size from small dense to large dense HDL, decreasing VLDL-triglyceride levels, decreasing VLDL-triglyceride levels, decreasing adipose tissue mass, increasing fatty acid oxidation in adipose tissue or skeletal muscle, increasing energy expenditure and improving islet function. The present invention also provides compounds, compositions and methods useful for treating Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity, eating disorders and suppressing appetite.

BRIEF SUMMARY OF THE INVENTION

In one aspect, the present invention provides compounds having the formula:

(I)

wherein $Ar^1$ represents a monocyclic or bicyclic aromatic ring selected from the group consisting of benzene, naphthylene, imidazole, benzimidazole, pyrrole, indole, indazole, thiophene, benzothiophene, furan, benzofuran and benzodioxole. Each of these rings can be optionally substituted with a $R^2$ substituent, a $R^3$ substituent or a combination of $R^2$ and $R^3$ substituents.

In the above formula, the symbol $Ar^2$ represents a 6-membered monocyclic aromatic ring. A variety of $Ar^2$ aryl groups provide compounds having the desired activity. In particular, $Ar^2$ aryl groups can be benzene, pyridine, pyrazine, pyrimidine, pyridazine and triazine. Each of these rings can be optionally substituted with from one to two $R^4$ substituents.

Within $Ar^1$ and $Ar^2$, variables $R^2$, $R^3$ and $R^4$ represent from one to two substituents on their respective rings, wherein each substituent present can be the same or different from any other substituent. More particularly, each $R^2$ or $R^3$ substituent is independently selected from the group consisting of halogen, $(C_1-C_8)$alkyl, halo$(C_1-C_8)$alkyl, $-OR^7$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^7$, $-CO_2R^7$, $-NR^7R^{24}$, $-NO_2$, $-CN$, $-S(O)_{r1}R^7$, $-X^1OR^7$, $-X^1COR^7$, $-X^1CO_2R^7$, $-X^1NR^7R^{24}$, $-X^1NO_2$, $-X^1CN$ and $-X^1S(O)_{r1}R^7$. More particularly, $R^4$ is independently selected from the group consisting of halogen, $(C_1-C_8)$alkyl, halo$(C_1-C_8)$alkyl, $-OR^7$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^7$, $-CO_2R^7$, $-NR^7R^{24}$, $-NO_2$, $-CN$, $-S(O)_{r1}R^7$, $-X^2OR^7$, $-X^2COR^7$, $-X^2CO_2R^7$, $-X^2NR^7R^{24}$, $-X^2NO_2$, $-X^2CN$, $-X^2S(O)_{r1}R^7$,

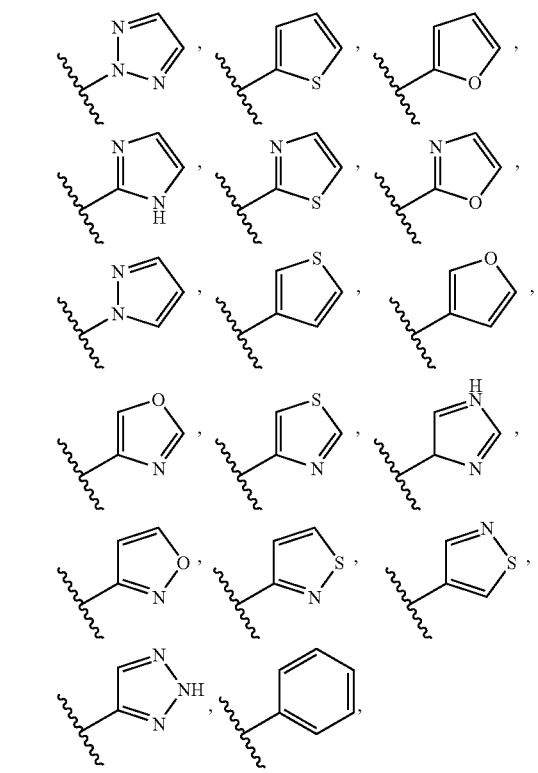

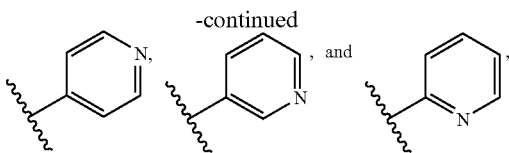

each ring of which is optionally substituted with from one to two substituents independently selected from the group consisting of halo and $(C_1-C_8)$alkyl; and the wavy line indicates the point of attachment to $Ar^2$. Within these designations, each $R^7$ and $R^{24}$ is a member independently selected from the group consisting of H, $(C_1-C_8)$alkyl, halo$(C_1-C_8)$alkyl, —$X^3OR^{25}$, —CO, aryl, aryl$(C_1-C_4)$alkyl and heteroaryl or optionally, if both are present on the same atom, may be joined together to form a three- to eight-membered ring. $R^{25}$ is a member selected from the group consisting of H, $(C_1-C_8)$ alkyl, halo$(C_1-C_8)$alkyl, aryl, aryl$(C_1-C_4)$alkyl and heteroaryl. Each $X^1$, $X^2$ and $X^3$ is a member independently selected from the group consisting of $(C_1-C_4)$alkylene, $(C_2-C_4)$alkenylene and $(C_2-C_4)$alkynylene. The subscript r1 is an integer of from 0 to 2.

Returning to formula (I), K represents a linking group having from one to seven main chain atoms and having the formula —$Y^1_{m1}Y^2_{m2}Y^3_{m3}$— wherein K can be attached to any available ring member of $Ar^1$.

Similarly, L represents a linking group having from one to seven main chain atoms and having the formula —$Y^4_{m4}Y^5_{m5}Y^6_{m6}$— wherein L can be attached to any available ring member of $Ar^1$ or $Ar^2$. Each $Y^1, Y^2, Y^3, Y^4, Y^5$ and $Y^6$ represents a member independently selected from the group consisting of —$(CR^5R^6)_p$—, —C=O—, —C=ONR^7—, —C=NOR^7—, —NR^7C=O—, —NR^7—, —O—, —S(O)_{r2}—, —NR^7SO_2— and —SO_2NR^7—; wherein $R^7$ is as defined above. Each $R^5$ and $R^6$ are members independently selected from the group consisting of H, halogen, $(C_1-C_8)$ alkyl, halo$(C_1-C_8)$alkyl, $OR^7$, aryl, heteroaryl and aryl$(C_1-C_4)$alkyl or optionally, if both are present on the same atom, may be joined together to form a three- to eight-membered ring or if present on adjacent carbon atoms are combined to form a double bond or triple bond between the atoms to which they are attached. Each subscript m1-m6 is an integer of from 0 to 1, the subscript r2 is an integer of from 0 to 2; and the subscript p is an integer of from 1 to 4. More preferably the subscript m1 is 0, the subscript r2 is 0; and the subscripts m2-m6 are 1. More preferably the subscript p is 3.

Returning to formula (I), Z is selected from the group consisting of $CH_2OR^8$, $CO_2R^8$, CN, tetrazol-5-yl, $CONR^8_2$, $CONHSO_2R^7$ and CHO; wherein each $R^8$ is a member independently selected from the group consisting of H, $(C_1-C_8)$ alkyl, halo$(C_1-C_8)$alkyl, —$X^4OR^7$, —$X^4NR^7R^{24}$, $(C_2-C_8)$ alkenyl, $(C_3-C_7)$cycloalkyl, heterocyclyl, heteroaryl, aryl, aryl$(C_1-C_4)$alkyl and aryl$(C_2-C_8)$alkenyl. $X^4$ is a member independently selected from the group consisting of $(C_1-C_4)$ alkylene, $(C_2-C_4)$alkenylene and $(C_2-C_4)$alkynylene. $R^7$ and $R^{24}$ are as defined above.

Returning to formula (I), the symbol $R^1$ represents a member independently selected from the group consisting of:

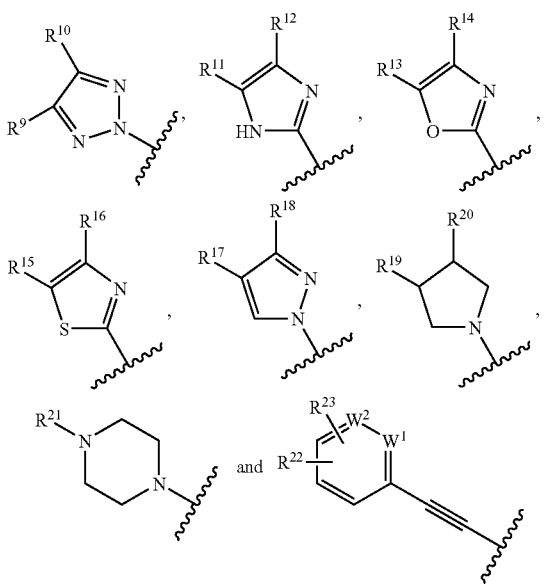

wherein the wavy line indicates the point of attachment to the rest of the molecule.

Each $R^9$ or $R^{10}$ is independently selected from the group consisting of H, $(C_1-C_8)$alkyl, halo and $(C_1-C_8)$haloalkyl or is joined together with the triazole ring to form a triazolopyridine, benzotriazole or tetrahydrobenzotriazole ring optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

Each $R^{11}$ or $R^{12}$ is independently selected from the group consisting of H, $(C_1-C_8)$alkyl, halo and $(C_1-C_8)$haloalkyl or is joined together with the imidazole ring to form a benzimidazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

Each $R^{13}$ or $R^{14}$ is independently selected from the group consisting of H, $(C_1-C_8)$alkyl, halo and $(C_1-C_8)$haloalkyl or is joined together with the oxazole ring to form a benzoxazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

Each $R^{15}$ or $R^{16}$ is independently selected from the group consisting of H, $(C_1-C_8)$alkyl, halo and $(C_1-C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

Each $R^{17}$ or $R^{18}$ is independently selected from the group consisting of H, $(C_1-C_8)$alkyl, halo and $(C_1-C_8)$haloalkyl or is joined together with the pyrazole ring to form a indazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

Each $R^{19}$ or $R^{20}$ is independently selected from the group consisting of H, $(C_1-C_8)$alkyl, halo and $(C_1-C_8)$haloalkyl or is joined together with the pyrrolidine ring to form a dihydroisoindole ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

$R^{21}$ is $CH_3$, phenyl or pyridyl, wherein the phenyl and pyridyl substituents are, optionally substituted with from one to two substituents independently selected from the group consisting of —$OR^7$, halo, $(C_1-C_8)$alkyl and $(C_1-C_8)$haloalkyl.

Each of $R^{22}$ or $R^{23}$ is independently selected from the group consisting of H, $(C_1-C_8)$alkyl, —$OR^7$, halo or $(C_1-C_8)$haloalkyl.

Each $W^1$ or $W^2$ is independently N or $CR^{22}$.

In addition to compounds having formula (I) above, the present invention further includes all salts thereof and particularly, pharmaceutically acceptable salts thereof. Still further, the invention includes compounds that are single isomers of the above formula (e.g., single enantiomers of compounds having a single chiral center), as well as solvate, hydrate and prodrug forms thereof.

In other aspects, the present invention provides compositions containing one or more compounds of Formula (I), as well as methods for the use of such compounds and compositions, either alone or in combination with other pharmaceutical agents as provided in detail below. In particular, the present invention provides methods of using the compounds and/or compositions for the treatment of Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity, eating disorders, suppressing appetite. In addition, the present invention provides methods of using the compounds and/or compositions for the modulation of peroxisome proliferators activated receptor, insulin resistance, fibrinogen levels, leptin levels, LDLc, decreasing LDL particles numbers or shifting LDL particle size from small dense to large dense LDL, increasing HDL particles numbers or shifting HDL particle size from small dense to large dense HDL, decreasing VLDL-triglyceride levels, decreasing VLDL-triglyceride levels, decreasing adipose tissue mass, increasing fatty acid oxidation in adipose tissue or skeletal muscle, increasing energy expenditure and improving islet function. Additionally, the present invention provides methods of using the compounds and/or compositions for the treatment of diseases modulated by any of the isoforms of peroxisome proliferation activated receptor (PPAR).

DETAILED DESCRIPTION OF THE INVENTION

Abbreviations and Definitions

Figure 1A:
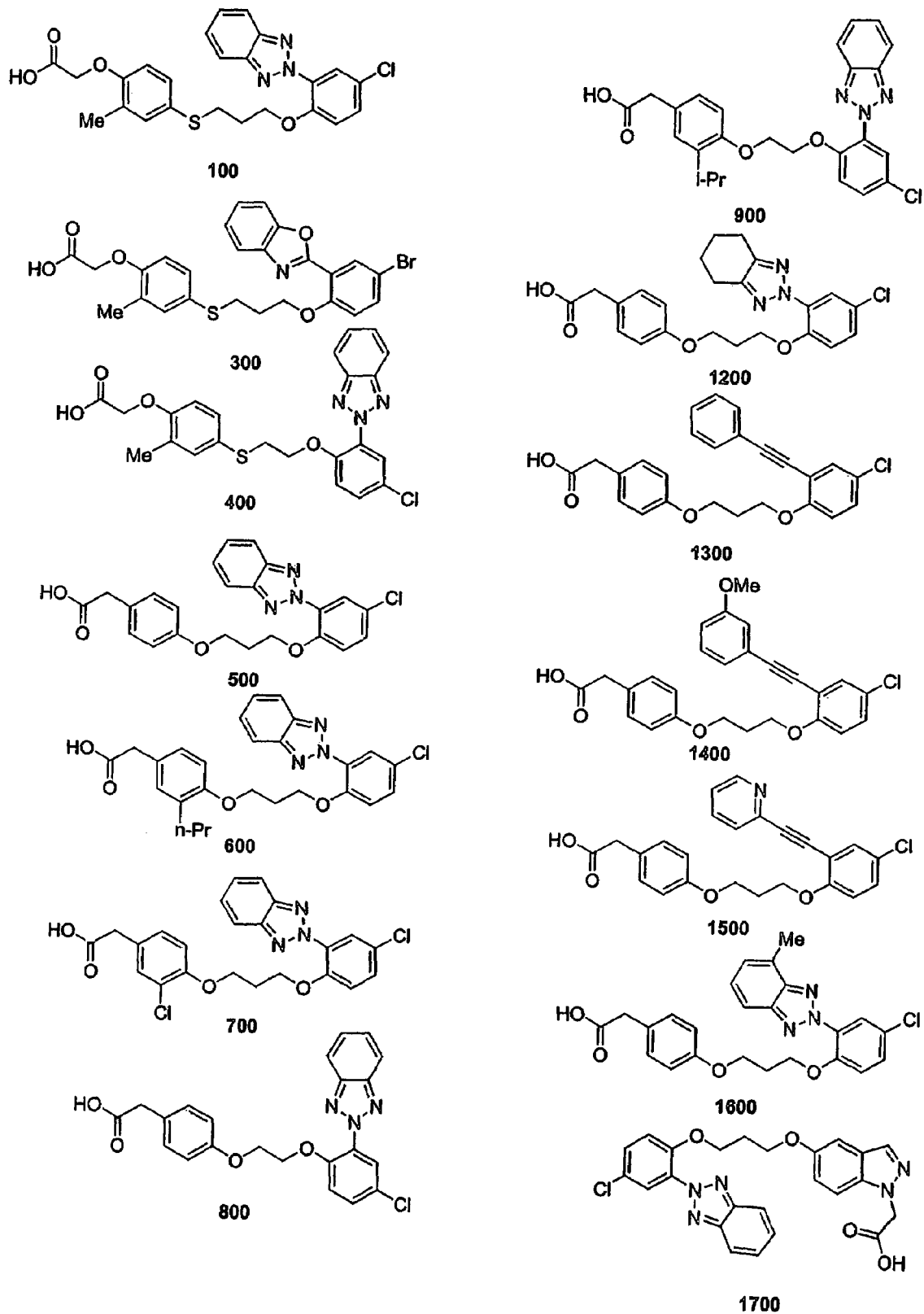
FIG. 1 illustrates a variety of preferred compounds of the invention.

The abbreviations used herein are conventional, unless otherwise defined: AcOH: acetic acid; BPO: benzoyl peroxide; $CBr_4$: tetrabromomethane; $Cs_2CO_3$: cesium carbonate; $CH_2Cl_2$: dichloromethane; $CuCl_2$: copper chloride; DIBAL: diisobutylaluminum hydride; DMSO: dimethyl sulfoxide; EtOAc: ethyl acetate; $H_2$: hydrogen; $H_2O$: water; HBr: hydrogen bromide; HCl: hydrogen chloride; KCN: potassium cyanide; $LiAlH_4$: lithium aluminum hydride; LiOH: lithium hydroxide; MeCN: acetonitrile; MeOH: methanol; $N_2$: nitrogen; $Na_2CO_3$: sodium carbonate; $NaHCO_3$: sodium bicarbonate; $NaNO_2$: sodium nitrite; NaOH: sodium hydroxide; $Na_2S_2O_3$: sodium thiosulfate; $Na_2SO_4$: sodium sulfate; NBS: N-bromosuccinamide; $NH_4Cl$: ammonium chloride; $NH_4OAc$: ammonium acetate; NMR: nuclear magnetic resonance; Pd/C: palladium on carbon; $PPh_3$: triphenyl phosphine; $SOCl_2$: thionyl chloride; THF: tetrahydrofuran; TLC: thin layer chromatography.

Unless otherwise stated, the following terms used in the specification and claims have the meanings given below:

"Alkyl" refers to a linear saturated monovalent hydrocarbon radical or a branched saturated monovalent hydrocarbon radical having the number of carbon atoms indicated in the prefix. For example, $(C_1-C_8)$alkyl is meant to include methyl, ethyl, n-propyl, 2-propyl, n-butyl, 2-butyl, tert-butyl, pentyl and the like. For each of the definitions herein (e.g., alkyl, alkenyl, alkoxy, araalkyloxy), when a prefix is not included to indicate the number of main chain carbon atoms in an alkyl portion, the radical or portion thereof will have six or fewer main chain carbon atoms.

"Alkylene" refers to a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene and the like.

"Alkenyl" refers to a linear monovalent hydrocarbon radical or a branched monovalent hydrocarbon radical having the number of carbon atoms indicated in the prefix and containing at least one double bond, but no more than three double bonds. For example, $(C_2-C_6)$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $(C_2-C_6)$alkynyl is meant to include ethynyl, propynyl and the like.

"Alkoxy", "aryloxy" or "araalkyloxy" refers to a radical —OR wherein R is an alkyl, aryl or arylalkyl, respectively, as defined herein, e.g., methoxy, phenoxy, benzyloxy and the like.

"Aryl" refers to a monovalent monocyclic or bicyclic aromatic hydrocarbon radical of 6 to 10 ring atoms which is substituted independently with one to four substituents, preferably one, two or three substituents selected from the group consisting of alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl, phenyl or phenylalkyl), —(CR'R")n-COOR (where n is an integer from 0 to 5, R' and R" are independently hydrogen or alkyl and R is hydrogen, alkyl, cycloalkyl, cycloalkylalkyl, phenyl or phenylalkyl) and —$(CR'R")_n$—$CONR^xR^y$ (where n is an integer from 0 to 5, R' and R" are independently hydrogen or alkyl and $R^x$ and $R^y$ are independently selected from the group consisting of hydrogen, alkyl, cycloalkyl, cycloalkylalkyl, phenyl and phenylalkyl). More specifically the term aryl includes, but is not limited to, phenyl, biphenyl, 1-naphthyl and 2-naphthyl and the substituted forms thereof.

"Araalkyl" or "Aryl$(C_1-C_x)$alkyl" refers to the radical —$R^xR^y$ where $R^x$ is an alkylene group (having eight or fewer main chain carbon atoms) and $R^y$ is an aryl group as defined above. Thus, "araalkyl" refers to groups such as, for example, benzyl, phenylethyl, 3-(4-nitrophenyl)-2-methylbutyl and the like. Similarly, "Araalkenyl" means a radical —$R^xR^y$ where Rx is an alkenylene group (an alkylene group having one or two double bonds) and $R^y$ is an aryl group as defined above, e.g., styryl, 3-phenyl-2-propenyl and the like.

"Cycloalkyl" refers to a monovalent cyclic hydrocarbon radical of three to seven ring carbons. The cycloalkyl group may have one double bond and may also be optionally substituted independently with one, two or three substituents selected from the group consisting of alkyl, optionally substituted phenyl and —C(O)$R^z$ (where $R^z$ is hydrogen, alkyl, haloalkyl, amino, mono-alkylamino, di-alkylamino, hydroxy, alkoxy or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl and the like.

"Cycloalkyl-alkyl" means a radical —$R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl and the like. The prefix indicating the number of carbon atoms (e.g., $C_4$-$C_{10}$) refers to the total number of carbon atoms from both the cycloalkyl portion and the alkyl portion.

"Haloalkyl" refers to an alkyl group which is substituted with one or more same or different halo atoms, e.g., —$CH_2Cl$, —$CH_2F$, —$CH_2Br$, —$CFClBr$, —$CH_2CH_2Cl$, —$CH_2CH_2F$, —$CF_3$, —$CH_2CF_3$, —$CH_2CCl_3$ and the like and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Haloalkoxy" refers to an alkoxy group which is substituted with one or more same or different halo atoms, e.g., —$CH_3OCHCl$, —$CH_3OCHF$, —$CH_3OCHBr$, —$CH_3OCHCH_2Cl$, —$CH_3CH_2OCHF$, —$CH_3OCHCF_3$ and the like.

"Heteroalkyl" means an alkyl radical as defined herein with one, two or three substituents independently selected from the group consisting of cyano, —$OR^w$, —$NR^xR^y$ and —$S(O)_nR^z$ (where n is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, araalkyl, alkoxycarbonyl, aryloxycarbonyl, carboxamido or mono- or di-alkylcarbamoyl. $R^x$ is hydrogen, alkyl, cycloalkyl, cycloalkyl-alkyl, aryl or araalkyl. Ry is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, araalkyl, amino, mono-alkylamino, di-alkylamino or hydroxyalkyl. Representative examples include, for example, 2-hydroxyethyl, 2,3-dihydroxypropyl, 2-methoxyethyl, benzyloxymethyl, 2-cyanoethyl and 2-methylsulfonyl-ethyl. For each of the above, $R^w$, $R^x$, $R^y$ and $R^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^w$, —$NR^xR^y$ or —$S(O)_nR^z$ portions.

"Heteroaryl" means a monovalent monocyclic or bicyclic radical of 5 to 12 ring atoms having at least one aromatic ring containing one, two or three ring heteroatoms selected from N, O or S, the remaining ring atoms being C, with the understanding that the attachment point of the heteroaryl radical will be on an aromatic ring. The heteroaryl ring is optionally substituted independently with one to four substituents, preferably one or two substituents, selected from the group consisting of alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl and R is hydrogen, alkyl, cycloalkyl, cycloalkyl-alkyl, phenyl or phenylalkyl) and —(CR'R")n-CONR$^x$R$^y$ (where n is an integer from 0 to 5, R' and R" are independently hydrogen or alkyl and $R^x$ and $R^y$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl and the derivatives thereof.

"Heterocyclyl" or "cycloheteroalkyl" means a saturated or unsaturated non-aromatic cyclic radical of 3 to 8 ring atoms in which one to four ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two or three substituents selected from alkyl, aryl, arylalkyl, heteroaryl, heteroarylalkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl and R is hydrogen, alkyl, cycloalkyl, cycloalkyl-alkyl, phenyl or phenylalkyl) or —(CR'R")$^n$—CONR$^x$R$^y$ (where n is an integer from 0 to 5, R' and R" are independently hydrogen or alkyl, $R^x$ and $R^y$ are, independently of each other, hydrogen, alkyl, cycloalkyl, cycloalkylalkyl, phenyl or phenylalkyl). More specifically the term heterocyclyl includes, but is not limited to, pyridyl, tetrahydropyranyl, piperidino, N-methylpiperidin-3-yl, piperazino, N-methylpyrrolidin-3-yl, 3-pyrrolidino, 2-pyrrolidon-1-yl, furyl, quinolyl, morpholino, thienyl, benzothienyl, thiomorpholino, thiomorpholino-1-oxide, thiomorpholino-1, 1-dioxide, pyrrolidinyl and the derivatives thereof. The prefix indicating the number of carbon atoms (e.g., $C_3$-$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —$R^xR^y$ where $R^x$ is an alkylene group and $R^y$ is a heterocyclyl group as defined herein, e.g., tetrahydropyran-2-ylmethyl, 4-(4-substituted-phenyl)piperazin-1-ylmethyl, 3-piperidinylethyl and the like.

The terms "optional" or "optionally" as used throughout the specification means that the subsequently described event or circumstance may but need not occur and that the description includes instances where the event or circumstance occurs and instances in which it does not. For example, "heterocyclo group optionally mono- or di-substituted with an alkyl group means that the alkyl may but need not be present and the description includes situations where the heterocyclo group is mono- or disubstituted with an alkyl group and situations where the heterocyclo group is not substituted with the alkyl group.

"Optionally substituted" means a ring which is optionally substituted independently with substituents.

For each of the definitions above, the term "di-alkylamino" refers to an amino moiety bearing two alkyl groups that can be the same or different.

As used herein, the term "carboxylic acid equivalent" refers to those moieties that are used as equivalents for a carboxylic acid moiety. Such groups are generally known to one of skill in the art (see, for example, The Practice of Medicinal Chemistry; Wermuth, C. G., ed., Academic Press, New York, 1996, page 203). Suitable isosteres or equivalents include—$C(O)NHSO_2R$ wherein R can be alkyl, haloalkyl, heteroalkyl, araalkyl, aryl, heteroaryl, heterocyclyl, alkoxy, haloalkoxy, aryloxy, alkylamino, haloalkylamino, dialkylamino, dihaloalkylamino, arylamino, diarylamino, araalkylamino, diaraalkylamino or other groups to provide an overall acidic character to the moiety; sulfonic acids; sulfinic acids; phosphonic acids; phosphinic acids; activated sulfonamides (e.g., —$SO_2NHX$ wherein X is an electron withdrawing group relative to an alkyl group, such as an acyl group or aryl group; activated carboxamides (e.g., —$C(O)NHCN$); hydroxamic acids (—$C(O)NHOH$); acidic heterocycles or substituted heterocycles (e.g., tetrazoles, triazoles, hydroxypyrazoles, hydroxyoxazoles, hydroxythiadiazoles); and acidic alcohols (e.g., —$C(CF_3)_2OH$ or —$CH(CF_3)OH$). The term "carboxylic acid equivalent" also refers to those moieties that may be converted into a carboxylic acid moiety in vivo. Such groups are generally known to one of skill in the art. While it is recognized that these groups initially may be non-acidic, suitable in vivo equivalents include aldehydes (CHO) and alcohols $CH_2OH$ and esters $CH_2OR$ wherein R can be alkyl, alkenyl, cycloalkyl, haloalkyl, heteroalkyl, araalkyl, aryl, heteroaryl, heterocyclyl, arylalkyl, arylalkenyl, alkoxy, haloalkoxy, aryloxy, alkylamino, haloalkylamino, dialkylamino, dihaloalkylamino, arylamino, diarylamino, araalkylamino, diaraalkylamino or other groups that are cleaved under physiological conditions to provide a hydroxyl group that can be oxidized in vivo to provide a carboxylic acid.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992).

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound either is replaced by a metal ion, e.g., an alkali metal ion, an alkaline earth ion or an aluminum ion; or coordinates with an organic base such as ethanolamine, diethanolamine, triethanolamine, trimethylamine, N-methylglucamine and the like.

"Prodrugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino or sulfhydryl group in a compound of Formula (I) is bonded to any group that may be cleaved in vivo to regenerate the free hydroxyl, amino or sulfhydryl group, respectively. Examples of prodrugs include, but are not limited to esters (e.g., acetate, formate and benzoate derivatives), amides/imides, carbamates (e.g., N,N-dimethylaminocarbonyl) of hydroxy functional groups in compounds of Formula (I) and the like.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991) and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable and includes a carrier or excipient that is acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms or (3) relieving the disease, i.e., causing regression of the disease or its clinical symptoms.

The term "therapeutically effective amount" means the amount of the subject compound that will elicit the biological or medical response of a tissue, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "patient" means all mammals, including humans. Examples of patients include, but are not limited to, humans, cows, dogs, cats, goats, sheep, pigs and rabbits.

The term "mammal" includes, without limitation, humans, domestic animals (e.g., dogs or cats), farm animals (cows, horses or pigs), monkeys, rabbits, mice and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M. *J. Basic & Clin. Phys. & Pharm.* (1998) 9: 387-406 and Flier, J. *Ann Rev. Med.* (1983) 34: 145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and skeletal muscle and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles and higher circulating levels of plasminogen activator inhibitor-1), has been referred to as "Syndrome X" (see, e.g., Reaven, G. M. *Physiol. Rev.* (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans, S. et al. *Diabet. Med.* (1996) (9 Suppl 6): S90-5 and Bell, G. et al., *Annu. Rev. Physiol.* (1996) 58: 171-86; genetic defects in insulin action; diseases of the exocrine pancreas (e.g., hemochromatosis, pancreatitis and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie and CMV); as well as other genetic syndromes.

The guidelines for diagnosis for Type 2 diabetes, impaired glucose tolerance and gestational diabetes have been outlined by the American Diabetes Association (see, e.g., The Expert Committee on the Diagnosis and Classification of Diabetes Mellitus, Diabetes Care, (1999) Vol 2 (Suppl 1): S5-19).

The term "hyperinsulinemia" refers to the presence of an abnormally elevated level of insulin in the blood. Similarly, the term "hyperuricemia" refers to the presence of an abnormally elevated level of uric acid in the blood. The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain s and two β chain s, respectively). Each subunit is formed by association of one globin protein and one heme molecule which is an iron-protoporphyrin complex. The major class of hemoglobin found in normal adult hemolysate is adult hemoglobin (referred to as "HbA"; also referred to $HbA_0$ for distinguishing it from glycated hemoglobin, which is referred to as "$HbA_1$," described infra) having $\alpha_2\beta_2$ subunits. Trace components such as $HbA_2$ ($\alpha_2\beta_2$) can also be found in normal adult hemolysate.

Among classes of adult hemoglobin HbAs, there is a glycated hemoglobin (referred to as "$HbA_1$," or "glycosylated hemoglobin"), which may be further fractionated into $HbA_{1a1}$, $HbA_{1a2}$, $HbA_{1b}$ and $HbA_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "HbA$_{1c}$,", "GHb", "hemoglobin-glycosylated", "diabetic control index" and "glycohemoglobin"; hereinafter referred to as "hemoglobin A$_{1c}$") refers to a stable product of the nonenzymatic glycosylation of the β-chain of hemoglobin by plasma glucose. Hemoglobin A$_{1c}$ comprises the main portion of glycated hemoglobins in the blood. The ratio of glycosylated hemoglobin is proportional to blood glucose level. Therefore, hemoglobin A$_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin HbA$_{1c}$ can be a good index for carbohydrate metabolism control. Accordingly, blood glucose levels of the last two months can be estimated on the basis of the ratio of HbA$_{1c}$ to total hemoglobin Hb. The analysis of the hemoglobin A$_{1c}$ in blood is used as a measurement enabling long-term control of blood glucose level (see, e.g., Jain, S. et al., *Diabetes* (1989) 38: 1539-1543; Peters A. et al., *JAMA* (1996) 276: 1246-1252).

The term "symptom" of diabetes, includes, but is not limited to, polyuria, polydipsia and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous ); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M. et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels. Similarly, the term "antiuricemic" refers to the lowering of excessive uric acid concentrations in blood to desired levels.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "triglyceride(s)" ("TGs"), as used herein, incorporates its common usage. TGs consist of three fatty acid molecules esterified to a glycerol molecule and serve to store fatty acids which are used by muscle cells for energy production/expenditure or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver or transformed into intermediate density lipoprotein ("IDL"). IDL, is in turn, either taken up by the liver or is further modified to form the low density lipoprotein ("LDL"). LDL is either taken up and broken down by the liver or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following:

(1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;

(2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 kg/m2 for men and 27.3 kg/m2 for women (BMI equals weight (kg)/height (m2). Obesity is linked to a variety of medical conditions including diabetes and hyperlipidemia. Obesity is also a known risk factor for the development of Type 2 diabetes (See, e.g., Barrett-Conner, E. *Epidemol. Rev.* (1989) 11: 172-181;and Knowler, et al. *Am. J. Clin. Nutr.* (1991)53:1543-1551).

General

The present invention derives from the discovery that compounds of Formula (I) are useful in treating or controlling a number of diseases associated with glucose metabolism, lipid metabolism and insulin secretion. More particularly, the compounds of the invention are useful in treating Type 2 diabetes, hyperinsulinemia, hyperlipidemia, hyperuricemia, hypercholesteremia, atherosclerosis, one or more risk factors for cardiovascular disease, Syndrome X, hypertriglyceridemia, hyperglycemia, obesity, eating disorders and suppressing appetite. Without intending to be bound by theory, it is considered that the compounds of Formula (I) operate via modulation of receptor interactions associated with one or more isoforms of PPAR. As a result, the compounds have utility in treating a variety of diseases states or conditions associated with PPAR.

Compounds

In one aspect, the present invention provides compounds having the formula:

$$Z-K-Ar^1-L-Ar^2-R \quad (I)$$

wherein $Ar^1$ represents a monocyclic or bicyclic aromatic ring selected from the group consisting of benzene, naphthylene, imidazole, benzimidazole, pyrrole, indole, indazole, thiophene, benzothiophene, furan, benzofuran and benzodioxole.

$Ar^2$ represents 6-membered monocyclic aromatic ring selected from the group consisting of benzene, pyridine, pyrazine, pyrimidine, pyridazine and triazine.

Returning to Formula (I), $Ar^1$ and $Ar^2$ may have substituents on their respective rings, wherein each substituted present can be the same or different from any other substituent. More particularly, $Ar^1$ may have from 0 to 2 $R^2$ or $R^3$ substituents, more preferably from 0 to 1 $R^2$ or $R^3$ substituents. Each $R^2$ or $R^3$ substituent is independently selected from the group consisting of halogen, $(C_1-C_8)$alkyl, halo$(C_1-C_8)$alkyl, $-OR^7$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^7$, $-CO_2R^7$, $-NR^7R^{24}$, $-NO_2$, $-CN$, $-S(O)_{r1}R^7$, $-X^1OR^7$, $-X^1COR^7$, $-X^1CO_2R^7$, $-X^1NR^7R^{24}$, $-X^1NO_2$, $-X^1CN$ and $-X^1S(O)_{r1}R^7$.

$Ar^2$ may have from 0 to 2 $R^4$ substituents, more preferably from 0 to 1 $R^4$ substituent $R^4$ substituents are independently selected from the group consisting of halogen, $(C_1-C_8)$alkyl, halo$(C_1-C_8)$alkyl, $-OR^7$, $(C_2-C_8)$alkenyl, $(C_2-C_8)$alkynyl, $(C_3-C_7)$cycloalkyl, $(C_3-C_7)$cycloalkyl$(C_1-C_4)$alkyl, aryl$(C_1-C_4)$alkyl, aryl$(C_2-C_8)$alkenyl, aryl$(C_2-C_8)$alkynyl, heterocyclyl, heterocyclyl$(C_1-C_4)$alkyl, $-COR^7$, $-CO_2R^7$, $-NR^7R^2$, $-NO_2$, $-CN$, $-S(O)_{r1}R^7$, $-X^2OR^7$, $-X^2COR^7$, $-XCO_2R^7$, $-X^2NR^7R^{24}$, $-X^2NO_2$, $-X^2CN$, $-X^2S(O)_{r1}R^7$;

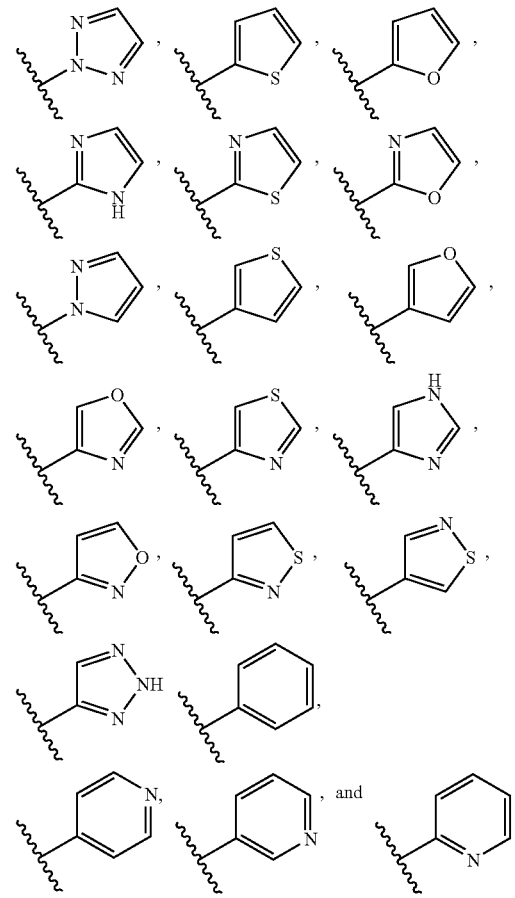

each ring of which is optionally substituted with from one to two substituents independently selected from the group consisting of halo and $(C_1-C_8)$alkyl; and the wavy line indicates the point of attachment to $Ar^2$.

K represents a linking group having from one to seven main chain atoms and having the formula $-Y^1_{m1}Y^2_{m2}Y^3_{m3}-$ wherein K can be attached to any available ring member of $Ar^1$; and each $Y^1$, $Y^2$ and $Y^3$ is a member independently selected from the group consisting of $-(CR^5R^6)_p-$, $-C=O-$, $-C=ONR^7-$, $-C=NOR^7-$, —NR$^7$C=O—, —NR$^7$—, —O—, —S(O)$_{r2}$—, —NR$^7$SO$_2$— and —SO$_2$NR$^7$—.

L represents a linking group joining Ar$^1$ and Ar$^2$ and having from one to seven main chain atoms represented by the formula —Y$^4_{m4}$Y$^5_{m5}$Y$^6_{m6}$— wherein L can be attached to any available ring member of Ar$^1$ and to any available ring member of Ar$^2$ and each Y$^4$, Y$^5$ and Y$^6$ is a member independently selected from the group consisting of —(CR$^5$R$^6$)$_p$—, —C=O—, —C=ONR$^7$—, —C=NOR$^7$—, —NR$^7$C=O—, —NR$^7$—, —O—, —S(O)$_{r2}$—, —NR$^7$SO$_2$— and —SO$_2$NR$^7$—.

Z represents a carboxylic acid equivalent and is selected from the group consisting of CH$_2$OR$^8$, CO$_2$R$^8$, CN, tetrazol-5-yl, CONHSO$_2$R$^7$ and CHO.

R$^1$ represents a member independently selected from the group consisting of:

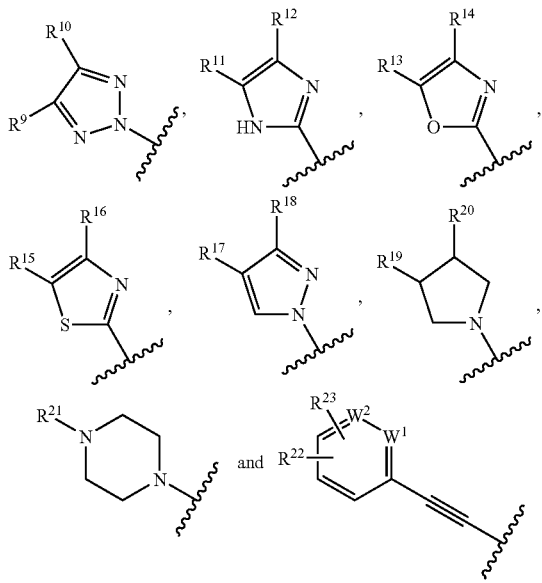

wherein the wavy line indicates the point of attachment to the rest of the molecule.

Each R$^5$ and R$^6$ is a member independently selected from the group consisting of H, halogen, (C$_1$-C$_8$)alkyl, halo(C$_1$-C$_8$)alkyl, —OR$^7$, aryl, heteroaryl and aryl(C$_1$-C$_4$)alkyl or optionally, if both are present on the same atom, may be joined together to form a three- to eight-membered ring or if present on adjacent carbon atoms are combined to form a double bond or triple bond between the atoms to which they are attached.

Each R$^7$ and R$^{24}$ is a member independently selected from the group consisting of H, (C$_1$-C$_8$)alkyl, halo(C$_1$-C$_8$)alkyl, —X$^3$OR$^{25}$, —CO, aryl, aryl(C$_1$-C$_4$)alkyl and heteroaryl or optionally, if both are present on the same substituent, may be joined together to form a three- to eight-membered ring. R$^{25}$ is a member selected from the group consisting of H, (C$_1$-C$_8$) alkyl, halo(C$_1$-C$_8$)alkyl, aryl, aryl(C$_1$-C$_4$)alkyl and heteroaryl.

Each R$^8$ is a member independently selected from the group consisting of H, (C$_1$-C$_8$)alkyl, halo(C$_1$-C$_8$)alkyl, —X$^4$OR$^7$, —X$^4$NR$^7$R$^{24}$, (C$_2$-C$_8$)alkenyl, (C$_3$-C$_7$)cycloalkyl, heterocyclyl, heteroaryl, aryl, aryl(C$_1$-C$_4$)alkyl and aryl(C$_2$-C$_8$)alkenyl.

Each R$^9$ or R$^{10}$ is independently selected from the group consisting of H, (C$_1$-C$_8$)alkyl, halo and (C$_1$-C$_8$)haloalkyl or is joined together with the triazole ring to form a triazolopyridine, benzotriazole or tetrahydrobenzotriazole ring optionally substituted with from one to two substituents independently selected from the group consisting of —OR$^7$, CO$_2$R$^7$, —NR$^7$R$^{24}$, —CN, —S(O)$_{r1}$R$^7$, halo, (C$_1$-C$_8$)alkyl and (C$_1$-C$_8$)haloalkyl.

Each R$^{11}$ or R$^{12}$ is independently selected from the group consisting of H, (C$_1$-C$_8$)alkyl, halo and (C$_1$-C$_8$)haloalkyl or is joined together with the imidazole ring to form a benzimidazolyl ring, optionally substituted with from one to two substituents independently selected from the group consisting of —OR$^7$, CO$_2$R$^7$, —NR$^7$R$^{24}$, —CN, —S(O)$_{r1}$R$^7$, halo, (C$_1$-C$_8$)alkyl and (C$_1$-C$_8$)haloalkyl.

Each R$^{13}$ or R$^{14}$ is independently selected from the group consisting of H, (C$_1$-C$_8$)alkyl, halo and (C$_1$-C$_8$)haloalkyl or is joined together with the oxazole ring to form a benzoxazolyl ring, optionally substituted with from one to two substituents independently selected from the group consisting of —OR$^7$, CO$_2$R$^7$, —NR$^7$R$^{24}$, —CN, —S(O)$_{r1}$R$^7$ halo, (C$_1$-C$_8$)alkyl and (C$_1$-C$_8$)haloalkyl.

Each R$^{15}$ or R$^{16}$ is independently selected from the group consisting of H, (C$_1$-C$_8$)alkyl, halo and (C$_1$-C$_8$)haloalkyl or is joined together with the thiazole ring to form a benzothiazoyl ring, optionally substituted with from one to two substituents independently selected from the group consisting of —OR$^7$, CO$_2$R$^7$, —NR$^7$R$^{24}$, —CN, —S(O)$_{r1}$R$^7$, halo, (C$_1$-C$_8$)alkyl and (C$_1$-C$_8$)haloalkyl.

Each R$^{17}$ or R$^{18}$ is independently selected from the group consisting of H, (C$_1$-C$_8$)alkyl, halo and (C$_1$-C$_8$)haloalkyl or is joined together with the pyrazole ring to form a indazoyl ring, optionally substituted with from one to two substituents independently selected from the group consisting of —OR$^7$, CO$_2$R$^7$, —NR$^7$R$^{24}$, —CN, —S(O)$_{r1}$R$^7$, halo, (C$_1$-C$_8$)alkyl and (C$_1$-C$_8$)haloalkyl.

Each R$^{19}$ or R$^{20}$ is independently selected from the group consisting of H, (C$_1$-C$_8$)alkyl, halo and (C$_1$-C$_8$)haloalkyl or is joined together with the pyrrolidine ring to form a dihydroisoindole ring, optionally substituted with from one to two substituents independently selected from the group consisting of —OR$^7$, CO$_2$R$^7$, —NR$^7$R$^{24}$, —CN, —S(O)$_{r1}$R$^7$, halo, (C$_1$-C$_8$)alkyl and (C$_1$-C$_8$)haloalkyl.

R$^{21}$ is CH$_3$, phenyl or pyridyl, wherein the phenyl and pyridyl substituents are, optionally substituted with from one to two substituents independently selected from the group consisting of —OR$^7$, halo, (C$_1$-C$_8$)alkyl and (C$_1$-C$_8$)haloalkyl.

Each of R$^{22}$ or R$^{23}$ is independently selected from the group consisting of H, (C$_1$-C$_8$)alkyl, —OR$^7$, halo and (C$_1$-C$_8$)haloalkyl.

Each W$^1$ or W$^2$ is independently N or CR$^{22}$.

Each X$^1$, X$^2$, X$^3$ and X$^4$ is a member independently selected from the group consisting of (C$_1$-C$_4$)alkyl, (C$_2$-C$_4$)alkenyl and (C$_2$-C$_4$)alkynyl.

The subscripts m1, m2, m3, m4, m5 and m6 are each integers of from 0 to 1; the subscripts r1 and r2 are integers of from 0 to 2; and the subscript p is an integer of from 1 to 4.

In addition to compounds having formula (I) above, the present invention further includes all salts thereof and particularly, pharmaceutically acceptable salts thereof. Still further, the invention includes compounds that are single isomers of the above formula (e.g., single enantiomers of compounds having a single chiral center), as well as solvate, hydrate and prodrug forms thereof.

A number of other groups of embodiments are preferred and are set forth below.

In a first group of embodiments, Z is CO$_2$R$^8$ and R$^8$ is preferably H.

In another group of embodiments, $Y^1$, $Y^2$, $Y^3$, $Y^4$, $Y^5$ and $Y^6$ is a member independently selected from the group consisting of —$(CR^5R^6)_p$—, —C=O—, —$NR^7$—, —O— and —S—; $R^7$ is H; each $R^5$ and $R^6$ is a member independently selected from the group consisting of H, $(C_1$-$C_8)$alkyl and halo$(C_1$-$C_8)$alkyl or optionally, if both are present on the same substituent, may be joined together to form a three- to eight-membered ring. In one aspect of this embodiment, preferably m1 is 0, $Y^2$ is —$(CR^5R^6)_p$— and $Y^3$ is —O—. In another aspect of this embodiment, preferably at least one of m1, m2 or m3 is 0. In yet another aspect of this embodiment, preferably K is a member selected from the group consisting of: —$CH_2$—, —$CH_2O$—, —$CH(CH_3)O$—, —$C(CH_3)_2O$—, —$CH(CH_3)$— and —$C(CH_3)_2$—. In a further aspect of this embodiment, preferably $Y^4$ is —$CR^5R^6$—, —$NR^7$—, —O— or —S—, $Y^5$ is —$CR^5R^6$— and $Y^6$ is —O— or —S—. In another aspect of this embodiment, preferably L is a member selected from the group consisting of: —$O(CH_2)_3O$—, —$O(CH_2)_2O$—, —$S(CH_2)_3O$—, —$S(CH_2)_2O$—, —NH$(CH_2)_3O$—, —$S(CH_2)_3S$—, —$O(CH_2)_3S$—, —$O(CH_2)_4$—, —$HCO(CH_2)_2O$—, —$(CH_2)_4$—, —$CH_2)_4O$—, —$(CH_2)_5$— and —$OCH_2(CH_3)_2CH_2O$—.

With regard to groups $R^5$ and $R^6$ each is independently H, $CH_3$ or joined together to form a three- to six-membered ring selected from the group consisting of cyclopropyl, cyclobutyl, cyclopentyl and cyclohexyl. Compounds, wherein both $R^5$ and $R^6$ are H are further preferred.

In another group of embodiments, $Ar^1$ is selected from the group consisting of:

(i) an indole ring, optionally substituted with a $R^2$ substituent, a $R^3$ substituent or a combination thereof;

(ii) an indazole ring, optionally substituted with a $R^2$ substituent, a $R^3$ substituent or a combination thereof;

(iii) a benzofuran ring, optionally substituted with a $R^2$ substituent, a $R^3$ substituent or a combination thereof; and (iv) a benzothiophene ring, optionally substituted with a $R^2$ substituent, a $R^3$ substituent or a combination thereof; wherein each $R^2$ or $R^3$ is independently selected from the group consisting of halogen, $(C_1$-$C_8)$alkyl, halo$(C_1$-$C_8)$alkyl and —$OR^7$. Within this embodiment, $Ar^1$ is preferably (i) an indole ring, optionally substituted with a $R^2$ substituent, a $R^3$ substituent or a combination thereof; or (ii) an indazole ring, optionally substituted with a $R^2$ substituent, a $R^3$ substituent or a combination thereof.

Within this embodiment, $Ar^1$ is preferably substituted with from one to three $R^7$ substituents independently selected from the group consisting of halogen, $(C_1$-$C_4)$haloalkyl, heterocyclyl, heterocyclyl$(C_1$-$C_4)$alkyl and —$OR^2$. Further preferred within this embodiment is where $Ar^1$ is

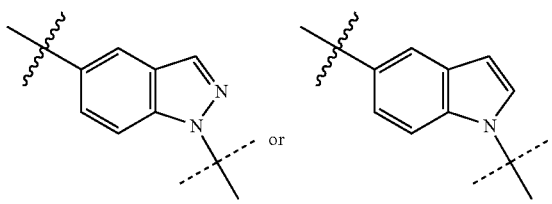 or optionally substituted with a $R^2$ substituent, a $R^3$ substituent or a combination thereof; wherein each $R^2$ or $R^3$ is independently selected from the group consisting of halogen, $(C_1$-$C_8)$ alkyl, halo$(C_1$-$C_8)$alkyl and —$OR^7$; and the dashed line indicates the point of attachment to K and the wavy line indicates the point of attachment to L. In one embodiment $Ar^1$ is preferably

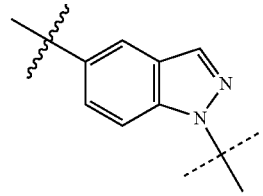

optionally substituted with a $R^2$ substituent, a $R^3$ substituent or a combination thereof; wherein each $R^2$ or $R^3$ is independently selected from the group consisting of halogen, $(C_1$-$C_8)$ alkyl, halo$(C_1$-$C_8)$alkyl and —$OR^7$; and the dashed line indicates the point of attachment to K and the wavy line indicates the point of attachment to L. Within this embodiment the compound

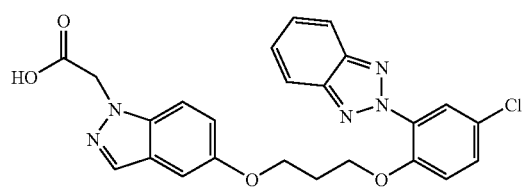

is preferred.

In another embodiment, $Ar^1$ is preferably

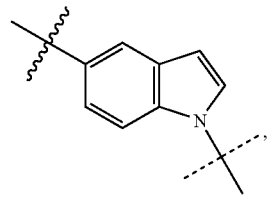

optionally substituted with a $R^2$ substituent, a $R^3$ substituent or a combination thereof, wherein each $R^2$ or $R^3$ is independently selected from the group consisting of halogen, $(C_1$-$C_8)$ alkyl, halo$(C_1$-$C_8)$alkyl and —$OR^7$; and the dashed line indicates the point of attachment to K and the wavy line indicates the point of attachment to L. Within this embodiment the compounds

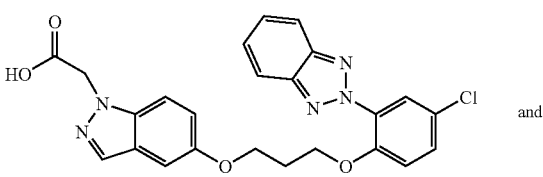 and

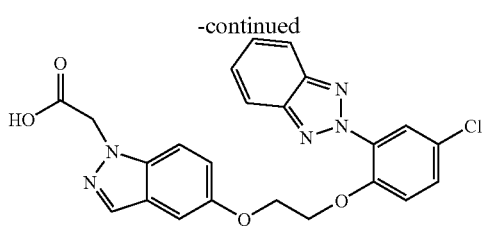

are preferred.

In other embodiments Ar$^1$ is preferably

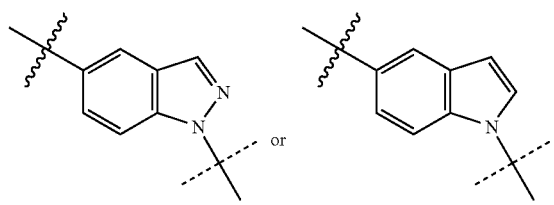

optionally substituted with a R$^2$ substituent, a R$^3$ substituent or a combination thereof; wherein each R$^2$ or R$^3$ is independently selected from the group consisting of halogen, (C$_1$-C$_8$) alkyl, halo(C$_1$-C$_8$)alkyl and —OR$^7$; and the dashed line indicates the point of attachment to L and the wavy line indicates the point of attachment to K. In one embodiment Ar$^1$ is preferably

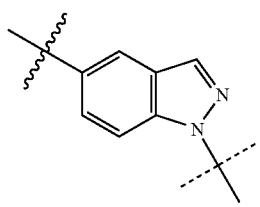

optionally substituted with a R$^2$ substituent, a R$^3$ substituent or a combination thereof; wherein each R$^2$ or R$^3$ is independently selected from the group consisting of halogen, (C$_1$-C$_8$) alkyl, halo(C$_1$-C$_8$)alkyl and —OR$^7$; and the dashed line indicates the point of attachment to L and the wavy line indicates the point of attachment to K. In another embodiment Ar$^1$ is preferably

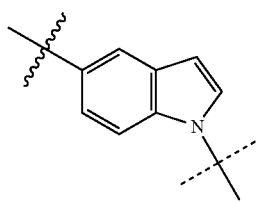

optionally substituted with a R$^2$ substituent, a R$^3$ substituent or a combination thereof; wherein each R$^2$ or R$^3$ is independently selected from the group consisting of halogen, (C$_1$-C$_8$) alkyl, halo(C$_1$-C$_8$)alkyl and —OR$^7$; and the dashed line indicates the point of attachment to L and the wavy line indicates the point of attachment to K.

In another group of embodiments, Ar$^1$ is more preferably benzene, optionally substituted with a R$^2$ substituent, a R$^3$ substituent or a combination thereof; wherein each R$^2$ or R$^3$ is independently selected from the group consisting of halogen, (C$_1$-C$_8$)alkyl, halo(C$_1$-C$_8$)alkyl and —OR$^7$.

R$^1$ is preferably a member selected from the group consisting of:

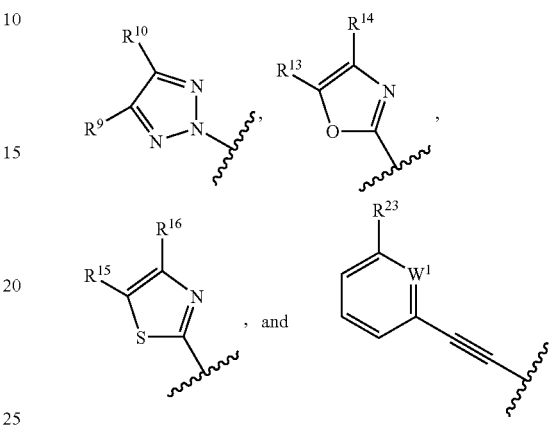

wherein the wavy line indicates the point of attachment to the rest of the molecule; each R$^9$ or R$^{10}$ is independently CH$_3$ or halo or is joined together with the triazole ring to form a triazolopyridine, benzotriazole or tetrahydrobenzotriazole ring optionally substituted with from one to two substituents independently selected from the group consisting of halo and (C$_1$-C$_8$)alkyl; each R$^{13}$ or R$^{14}$ is independently CH$_3$ halo or is joined together with the oxazole ring to form a benzoxazolyl ring, optionally substituted with from one to two (C$_1$-C$_8$)alkyl or halo; R$^{23}$ is halo or (C$_1$-C$_8$)alkoxy; and W$^1$ is N or CR$^{22}$. Each is equally preferred.

In one embodiment, Ar$^2$ is selected from the group consisting of: (i) benzene, optionally substituted with from one to two R$^4$ substituents as defined above. One preferred embodiment is when Ar$^2$ is pyridine. Within these embodiments, Ar$^2$ has the formula:

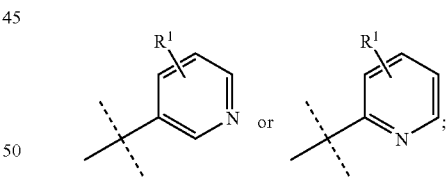

each of which is optionally substituted with from one to two R$^4$ substituents as defined above, and wherein the dashed line indicates the point of attachment to L.

Even further preferred are those embodiments in which Ar$^2$ has the formula:

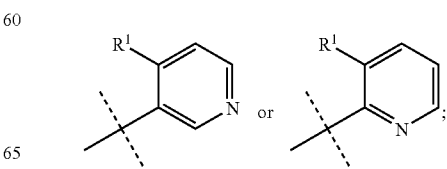

each of which is optionally substituted with from one to two $R^4$ substituents, and wherein the dashed line indicates the point of attachment to L.

In most preferred embodiments, $Ar^2$ is benzene and especially preferred are embodiments when L and K include their preferred embodiments above. Within these embodiments, $Ar^2$ is preferably has the formula:

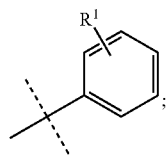

and more preferably:

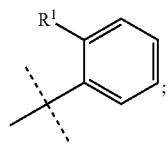

wherein the dashed line indicates the point of attachment to L.

In one preferred embodiment the compounds of the invention have having the formula:

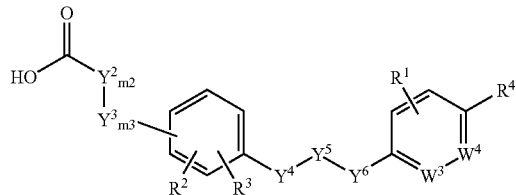

wherein $Y^2$ is —$CR^5R^6$—;

$Y^3$ is —S—, —O—, —NH— or —$CHR^6$—;

$Y^4$ is a member selected from the group consisting of —NHCO—, —NH—, —O—, —S— and —$CH_2$—, $Y^5$ is —$CH_2$—; —$CH_2CR^5R^6$— or —$CH_2CH_2CH_2$—

$Y^6$ is —S—, —O— or —$CH_2$—;

$R^1$ is a member independently selected from the group consisting of:

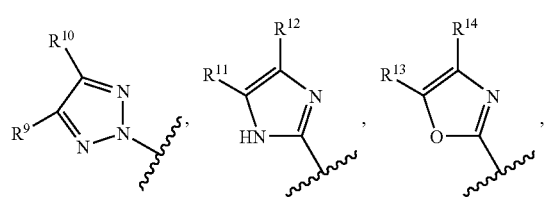

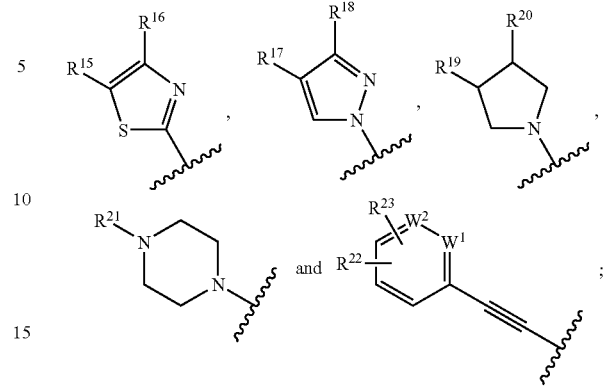

$R^2$ is H, $(C_1-C_8)$alkyl, $(C_1-C_8)$alkoxy, halo or $(C_1-C_8)$haloalkyl;

$R^3$ is a member independently selected from the group consisting of H, halogen and $(C_1-C_8)$alkyl;

$R^4$ is a member selected from the group consisting of —H, -halo, $(C_1-C_8)$alkyl, -halo$(C_1-C_8)$alkyl and $(C_1-C_8)$alkoxy or is a member of the group consisting of:

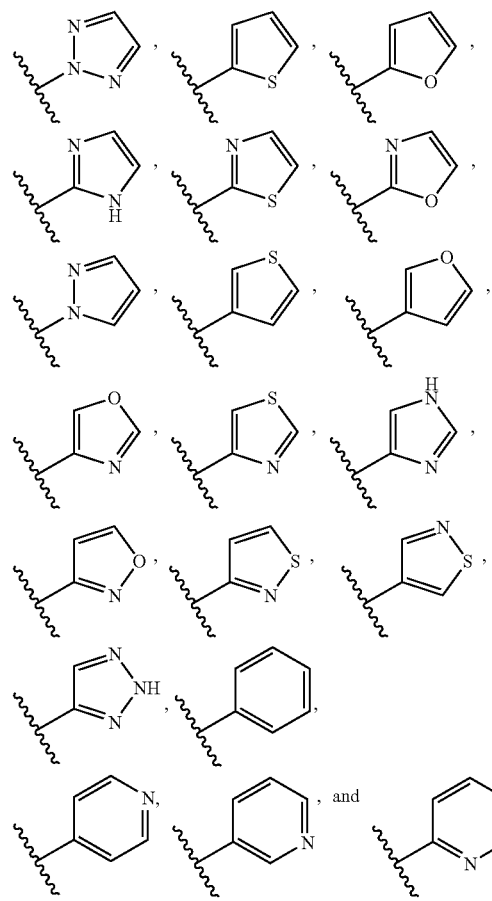

each ring of which is optionally substituted with from one to two substituents independently selected from the group consisting of halo and $(C_1-C_8)$alkyl;

each $R^5$ and $R^6$ is independently selected from the group consisting of H, $(C_1-C_8)$alkyl, $(C_1-C_8)$alkoxy and $(C_1-C_8)$haloalkyl or optionally, if both are present on the same substituent, may be joined together to form a three- to eight-membered ring;

each $R^9$ or $R^{10}$ is independently selected from the group consisting of H, $(C_1-C_8)$alkyl, halo and $(C_1-C_8)$haloalkyl or is joined together with the triazole ring to form a triazolopyridine, benzotriazole or tetrahydrobenzotriazole ring optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{11}$ or $R^{12}$ is independently selected from the group consisting of H, $(C_1-C_8)$alkyl, halo and $(C_1-C_8)$haloalkyl or is joined together with the imidazole ring to form a benzimidazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{13}$ or $R^{14}$ is independently selected from the group consisting of H, $(C_1-C_8)$alkyl, halo and $(C_1-C_8)$haloalkyl or is joined together with the oxazole ring to form a benzoxazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{15}$ or $R^{16}$ is independently selected from the group consisting of H, $(C_1-C_8)$alkyl, halo and $(C_1-C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{17}$ or $R^{18}$ is independently selected from the group consisting of H, $(C_1-C_8)$alkyl, halo and $(C_1-C_8)$haloalkyl or is joined together with the pyrazole ring to form a indazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{19}$ or $R^{20}$ is independently selected from the group consisting of H, $(C_1-C_8)$alkyl, halo and $(C_1-C_8)$haloalkyl or is joined together with the pyrrolidine ring to form a dihydroisoindole ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

$R^{21}$ is $CH_3$, phenyl or pyridyl, wherein the phenyl and pyridyl substituents are, optionally substituted with from one to two substituents independently selected from the group consisting of —$OR^7$, halo, $(C_1-C_8)$alkyl and $(C_1-C_8)$haloalkyl;

each of $R^{22}$ or $R^{23}$ is independently selected from the group consisting of H, $(C_1-C_8)$alkyl, —$OR^7$, halo and $(C_1-C_8)$haloalkyl;

$R^{25}$ is a member selected from the group consisting of H, $(C_1-C_8)$alkyl, halo$(C_1-C_8)$alkyl, aryl, aryl$(C_1-C_4)$alkyl and heteroaryl;

each $W^1$, $W^2$, $W^3$ or $W^4$ is independently N or $CR^{22}$;

the subscripts m2 and m3 are independently an integer of from 0 to 1;

the subscript p is an integer of from 1 to 4;

the wavy line indicates the point of attachment to the rest of the molecule; and pharmaceutically acceptable salts, solvates, hydrates and prodrugs thereof.

In one preferred embodiment the compounds of the invention have the formula:

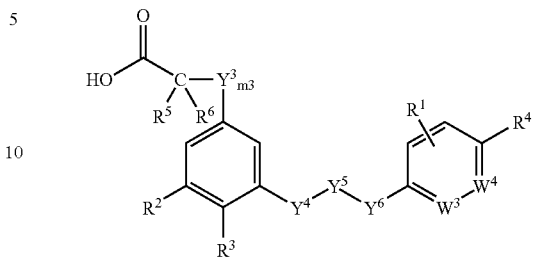

wherein
$Y^3$ is —S—, —O—, —NH—, —$CHR^6$—;
$Y^4$ is a member selected from the group consisting of —NHCO—, —NH—, —O—, —S— and —$CH_2$—,
$Y^5$ is —$CH_2$—; —$CH_2CR^5R^6$— or —$CH_2CH_2CH_2$—
$Y^6$ is —S—, —O— or —$CH_2$—;
$R^1$ is a member independently selected from the group consisting of:

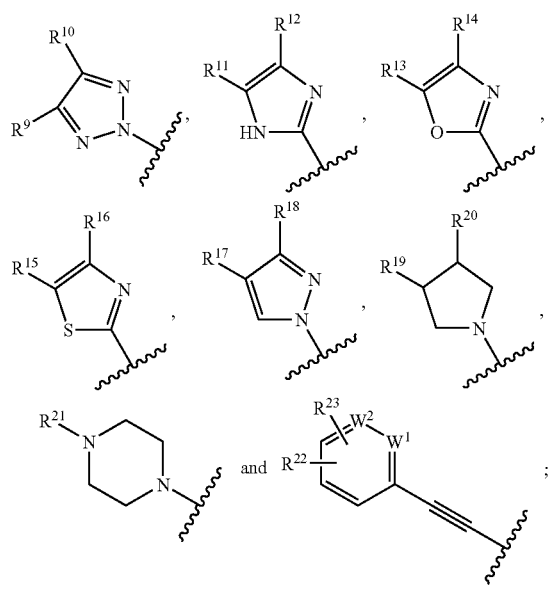

$R^2$ is H, $(C_1-C_8)$alkyl, $(C_1-C_8)$alkoxy, halo or $(C_1-C_8)$haloalkyl;
$R^3$ is a member independently selected from the group consisting of H, halogen and $(C_1-C_8)$alkyl;
$R^4$ is a member selected from the group consisting of H, -halo, $(C_1-C_8)$alkyl, halo$(C_1-C_8)$alkyl, $(C_1-C_8)$alkoxy,

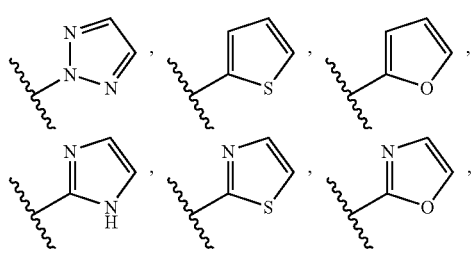

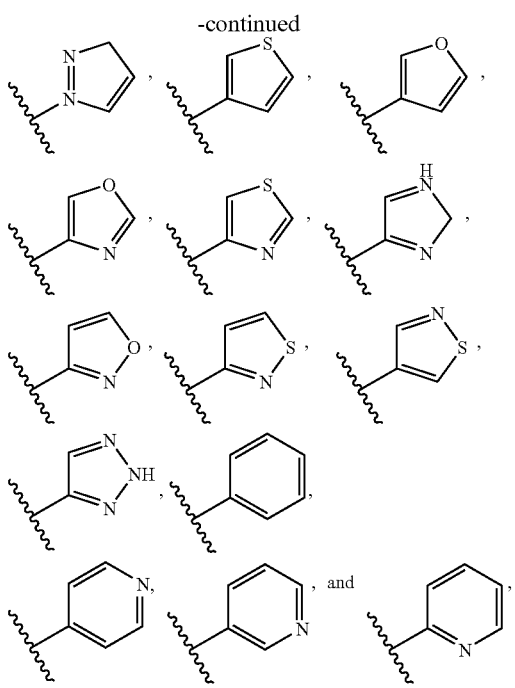

each ring of which is optionally substituted with from one to two substituents independently selected from the group consisting of halo and $(C_1-C_8)$alkyl;

each $R^5$ and $R^6$ is independently selected from the group consisting of H, $(C_1-C_8)$alkyl, $(C_1-C_8)$alkoxy and $(C_1-C_8)$haloalkyl or optionally, if both are present on the same substituent, may be joined together to form a three- to eight-membered ring;

each $R^9$ or $R^{10}$ is independently selected from the group consisting of H, $(C_1-C_8)$alkyl, halo and $(C_1-C_8)$haloalkyl or is joined together with the triazole ring to form a triazolopyridine, benzotriazole or tetrahydrobenzotriazole ring optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{11}$ or $R^{12}$ is independently selected from the group consisting of H, $(C_1-C_8)$alkyl, halo and $(C_1-C_8)$haloalkyl or is joined together with the imidazole ring to form a benzimidazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{13}$ or $R^{14}$ is independently selected from the group consisting of H, $(C_1-C_8)$alkyl, halo and $(C_1-C_8)$haloalkyl or is joined together with the oxazole ring to form a benzoxazolyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{15}$ or $R^{16}$ is independently selected from the group consisting of H, $(C_1-C_8)$alkyl, halo and $(C_1-C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{17}$ or $R^{18}$ is independently selected from the group consisting of H, $(C_1-C_8)$alkyl, halo and $(C_1-C_8)$haloalkyl or is joined together with the pyrazole ring to form a indazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

each $R^{19}$ or $R_{20}$ is independently selected from the group consisting of H, $(C_1-C_8)$alkyl, halo and $(C_1-C_8)$haloalkyl or is joined together with the pyrrolidine ring to form a dihydroisoindole ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl;

$R^{21}$ is $CH_3$, phenyl or pyridyl, wherein the phenyl and pyridyl substituents are, optionally substituted with from one to two substituents independently selected from the group consisting of —$OR^7$, halo, $(C_1-C_8)$alkyl and $(C_1-C_8)$haloalkyl;

each of $R^{22}$ or $R^{23}$ is independently selected from the group consisting of H, $(C_1-C_8)$alkyl, —$OR^7$, halo or $(C_1-C_8)$haloalkyl;

$R^{25}$ is a member selected from the group consisting of H, $(C_1-C_8)$alkyl, halo$(C_1-C_8)$alkyl, aryl, aryl$(C_1-C_4)$alkyl and heteroaryl;

each $W^1$, $W^2$, $W^3$ or $W^4$ is independently N or $CR^{22}$;

the subscript m3 is an integer of from 0 to 1;

the subscript p is an integer of from 1 to 4;

the wavy line indicates the point of attachment to the rest of the molecule; and pharmaceutically acceptable salts, solvates, hydrates and prodrugs thereof.

Within this embodiment, the compound

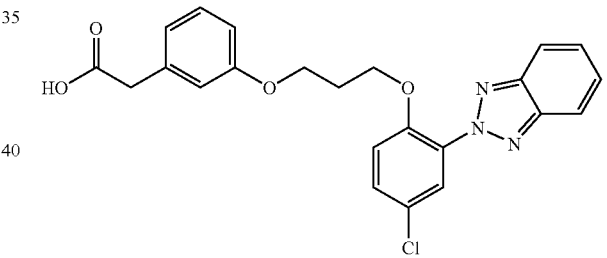

is preferred.

In one preferred embodiment the compounds of the invention have the formula:

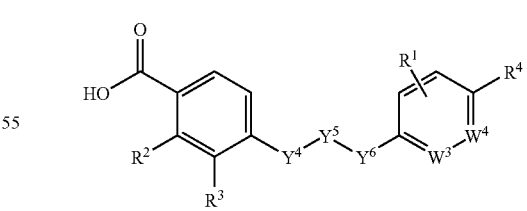

wherein $Y^4$ is a member selected from the group consisting of —NHCO—, —NH—, —O—, —S— and —$CH_2$—, $Y^5$ is —$CH_2$—; —$CH_2CR^5R^6$— or —$CH_2CH_2CH_2$—

$Y^6$ is —S—, —O— or —$CH_2$—;

$R^1$ is a member independently selected from the group consisting of:

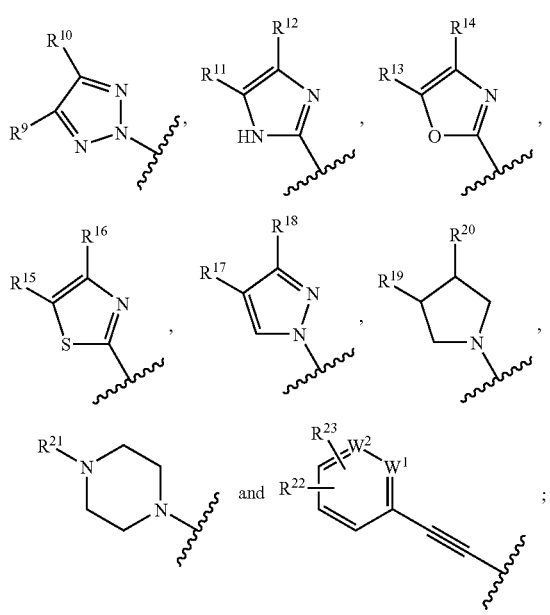

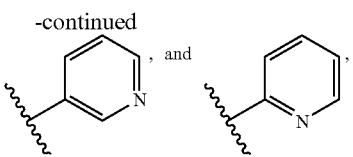

each ring of which is optionally substituted with from one to two substituents independently selected from the group consisting of halo and $(C_1\text{-}C_8)$alkyl;

each $R^5$ and $R^6$ is independently selected from the group consisting of H, $(C_1\text{-}C_8)$alkyl, $(C_1\text{-}C_8)$alkoxy and $(C_1\text{-}C_8)$haloalkyl or optionally, if both are present on the same substituent, may be joined together to form a three- to eight-membered ring;

each $R^9$ or $R^{10}$ is independently selected from the group consisting of H, $(C_1\text{-}C_8)$alkyl, halo and $(C_1\text{-}C_8)$haloalkyl or is joined together with the triazole ring to form a triazolopyridine, benzotriazole or tetrahydrobenzotriazole ring optionally substituted with from one to two substituents independently selected from the group consisting of —$OR^7$, —$CO_2R^7$, —$NR^7R^{24}$, —CN, —$S(O)_{r1}R^7$, halo, $(C_1\text{-}C_8)$alkyl and $(C_1\text{-}C_8)$haloalkyl;

each $R^{11}$ or $R^{12}$ is independently selected from the group consisting of H, $(C_1\text{-}C_8)$alkyl, halo and $(C_1\text{-}C_8)$haloalkyl or is joined together with the imidazole ring to form a benzimidazolyl ring, optionally substituted with from one to two substituents independently selected from the group consisting of —$OR^7$, —$CO_2R^7$, —$NR^7R^{24}$, —CN, —$S(O)^{r1}R^7$, halo, $(C_1\text{-}C_8)$alkyl and $(C_1\text{-}C_8)$haloalkyl;

each $R^{13}$ or $R^{14}$ is independently selected from the group consisting of H, $(C_1\text{-}C_8)$alkyl, halo and $(C_1\text{-}C_8)$haloalkyl or is joined together with the oxazole ring to form a benzoxazolyl ring, optionally substituted with from one to two substituents independently selected from the group consisting of —$OR^7$, —$CO_2R^7$, —$NR^7R^{24}$, —CN, —$S(O)^{r1}R^7$, halo, $(C_1\text{-}C_8)$alkyl and $(C_1\text{-}C_8)$haloalkyl;

each $R^{15}$ or $R^{16}$ is independently selected from the group consisting of H, $(C_1\text{-}C_8)$alkyl, halo and $(C_1\text{-}C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, $S(O)_{r1}R^7$ halo, $(C_1\text{-}C_8)$alkyl and $(C_1\text{-}C_8)$haloalkyl;

each $R^{17}$ or $R^{18}$ is independently selected from the group consisting of H, $(C_1\text{-}C_8)$alkyl, halo and $(C_1\text{-}C_8)$haloalkyl or is joined together with the pyrazole ring to form a indazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1\text{-}C_8)$alkyl and $(C_1\text{-}C_8)$haloalkyl;

each $R^{19}$ or $R^{20}$ is independently selected from the group consisting of H, $(C_1\text{-}C_8)$alkyl, halo and $(C_1\text{-}C_8)$haloalkyl or is joined together with the pyrrolidine ring to form a dihydroisoindole ring, optionally substituted with from one to two substituents independently selected from the group consisting of —$OR^7$, —$CO_2R^7$, —$NR^7R^{24}$, —CN, —$S(O)_{r1}R^7$, halo, $(C_1\text{-}C_8)$alkyl and $(C_1\text{-}C_8)$haloalkyl;

$R^{21}$ is $CH_3$, phenyl or pyridyl, wherein the phenyl and pyridyl substituents are, optionally substituted with from one to two substituents independently selected from the group consisting of —$OR^7$, halo, $(C_1\text{-}C_8)$alkyl and $(C_1\text{-}C_8)$haloalkyl;

$R^2$ is H, $(C_1\text{-}C_8)$alkyl, $(C_1\text{-}C_8)$alkoxy, halo or $(C_1\text{-}C_8)$haloalkyl;

$R^3$ is a member independently selected from the group consisting of H, halogen and $(C_1\text{-}C_8)$alkyl;

$R^4$ is a member selected from the group consisting of —H, halo, $(C_1\text{-}C_8)$alkyl, halo$(C_1\text{-}C_8)$alkyl, $(C_1\text{-}C_8)$alkoxy,

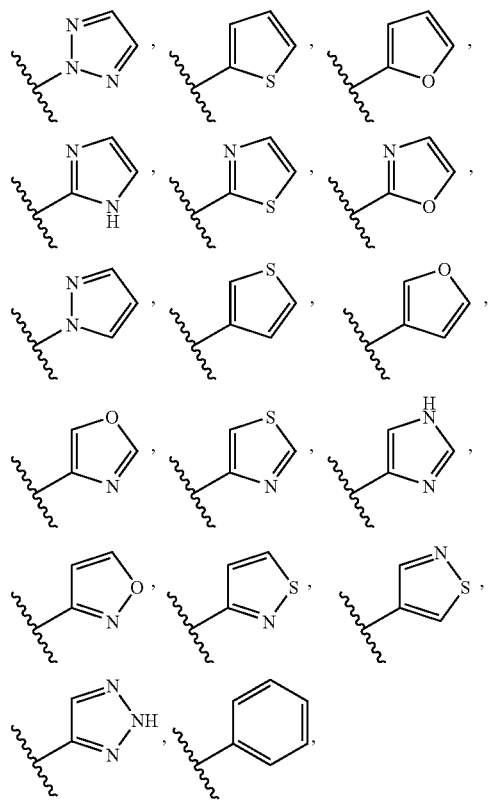

each of $R^{22}$ or $R^{23}$ is independently selected from the group consisting of H, $(C_1$-$C_8)$alkyl, —$OR^7$, halo and $(C_1$-$C_8)$haloalkyl;

$R^{25}$ is a member selected from the group consisting of H, $(C_1$-$C_8)$alkyl, halo$(C_1$-$C_8)$alkyl, aryl, aryl$(C_1$-$C_4)$alkyl and heteroaryl;

each $W^1$, $W^2$, $W^3$ or $W^4$ is independently N or $CR^{22}$;

the subscript m3 is an integer of from 0 to 1;

the subscript p is an integer of from 1 to 4;

the wavy line indicates the point of attachment to the rest of the molecule; and pharmaceutically acceptable salts, solvates, hydrates and prodrugs thereof.

Within this embodiment, the compound

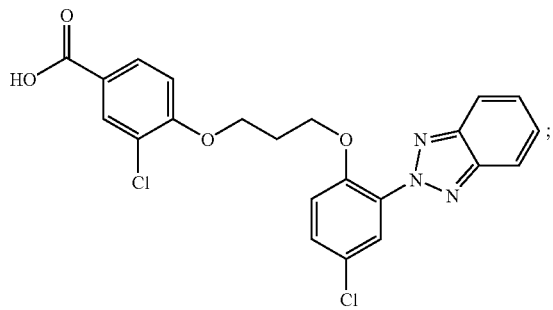

is preferred.

In one preferred embodiment the compounds of the invention have the formula:

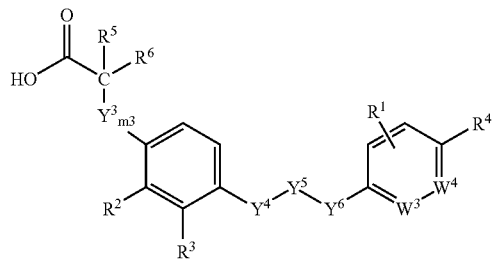

wherein $Y^3$ is —S—, —O—, —NH—, —$CHR^6$—;

$Y^4$ is a member selected from the group consisting of —NHCO—, —NH—, —O—, —S— and —$CH_2$—, $Y^5$ is —$CH_2$—; —$CH_2CR^5R^6$— or —$CH_2CH_2CH_2$—

$Y^6$ is —S—, —O— or —$CH_2$—;

$R^1$ is a member independently selected from the group consisting of:

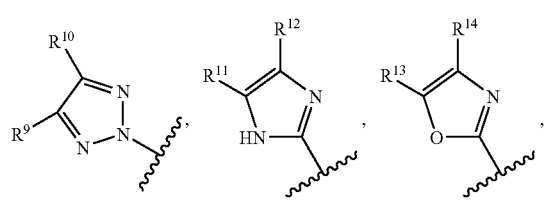

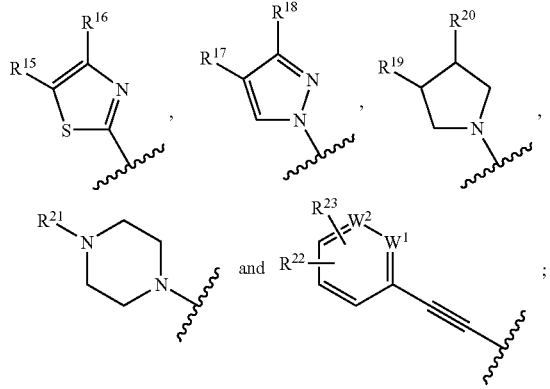

wherein the wavy line indicates the point of attachment to the rest of the molecule;

$R^2$ is H, $(C_1$-$C_8)$alkyl, $(C_1$-$C_8)$alkoxy, halo or $(C_1$-$C_8)$haloalkyl;

$R^3$ is a member independently selected from the group consisting of H, halogen and $(C_1$-$C_8)$alkyl;

$R^4$ is a member selected from the group consisting of -halo, $(C_1$-$C_8)$alkyl, -halo$(C_1$-$C_8)$alkyl, $(C_1$-$C_8)$alkoxy,

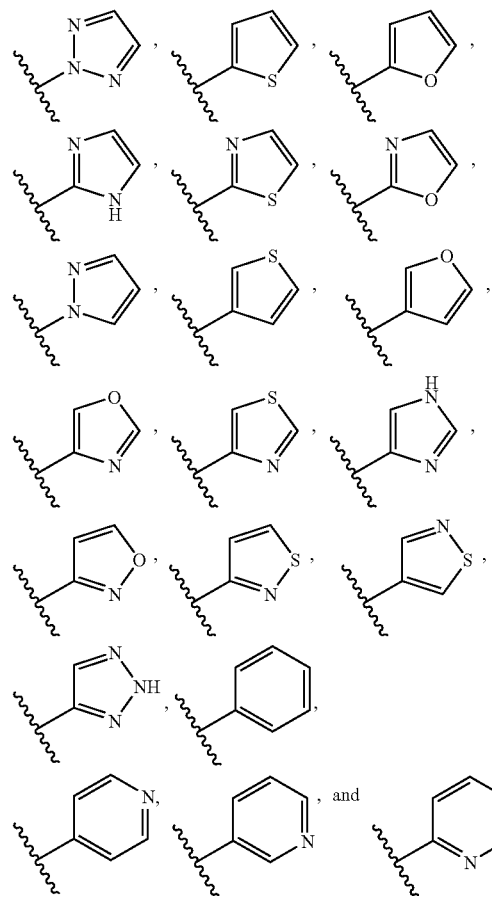

wherein the wavy line indicates the point of attachment to $Ar^2$; each ring of which is optionally substituted with from one to two substituents independently selected from the group consisting of halo and (C₁-C₈)alkyl;

each R⁵ and R⁶ is independently selected from the group consisting of H, (C₁-C₈)alkyl, (C₁-C₈)alkoxy and (C₁-C₈) haloalkyl or optionally, if both are present on the same substituent, may be joined together to form a three- to eight-membered ring;

each R⁹ or R¹⁰ is independently selected from the group consisting of H, (C₁-C₈)alkyl, halo and (C₁-C₈)haloalkyl or is joined together with the triazole ring to form a triazolopyridine, benzotriazole or tetrahydrobenzotriazole ring optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹¹ or R¹² is independently selected from the group consisting of H, (C₁-C₈)alkyl, halo and (C₁-C₈)haloalkyl or is joined together with the imidazole ring to form a benzimidazolyl ring, optionally substituted with from one to two substituents independently selected from the group consisting of —OR⁷, —CO₂R⁷, —NR⁷R²⁴, —CN, S(O)$_{r1}$R⁷, halo, (C₁-C₈)alkyl and (C₁-C₈)haloalkyl;

each R¹³ or R¹⁴ is independently selected from the group consisting of H, (C₁-C₈)alkyl, halo and (C₁-C₈)haloalkyl or is joined together with the oxazole ring to form a benzoxazolyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁵ or R¹⁶ is independently selected from the group consisting of H, (C₁-C₈)alkyl, halo and (C₁-C₈)haloalkyl or is joined together with the thiazole ring to form a benzothiazoyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁷ or R¹⁸ is independently selected from the group consisting of H, (C₁-C₈)alkyl, halo and (C₁-C₈)haloalkyl or is joined together with the pyrazole ring to form a indazoyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁹ or R₂₀ is independently selected from the group consisting of H, (C₁-C₈)alkyl, halo and (C₁-C₈)haloalkyl or is joined together with the pyrrolidine ring to form a dihydroisoindole ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

R²¹ is CH₃, phenyl or pyridyl, wherein the phenyl and pyridyl substituents are, optionally substituted with from one to two substituents independently selected from the group consisting of —OR⁷, halo, (C₁-C₈)alkyl and (C₁-C₈)haloalkyl;

each of R²² or R²³ is independently selected from the group consisting of H, (C₁-C₈)alkyl, halo or (C₁-C₈)haloalkyl;

R²⁵ is a member selected from the group consisting of H, (C₁-C₈)alkyl, halo(C₁-C₈)alkyl, aryl, aryl(C₁-C₄)alkyl and heteroaryl;

each W¹, W², W³ or W⁴ is independently N or CR²²; and the subscript m3 is an integer of from 0 to 1.

R¹ is preferably a member selected from the group consisting of:

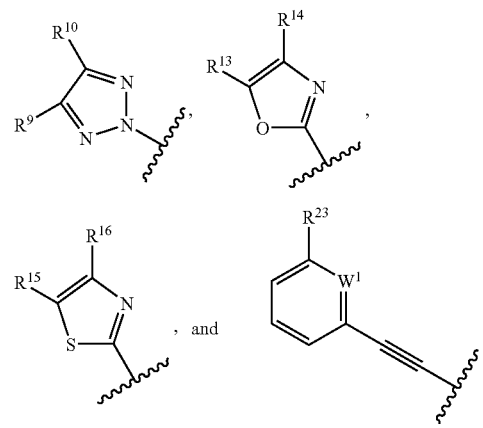

wherein the wavy line indicates the point of attachment to the rest of the molecule; each R⁹ or R¹⁰ is independently CH₃ or halo or is joined together with the triazole ring to form a triazolopyridine, benzotriazole or tetrahydrobenzotriazole ring optionally substituted with from one to two substituents independently selected from the group consisting of halo and (C₁-C₈)alkyl; each R¹³ or R¹⁴ is independently CH₃, halo or is joined together with the oxazole ring to form a benzoxazolyl ring, optionally substituted with from one to two (C₁-C₈)alkyl or halo substituents; each R¹⁵ or R¹⁶ is independently H, (C₁-C₈)alkyl, halo or (C₁-C₈)haloalkyl or is joined together with the thiazole ring to form a benzothiazoyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl; R²³ is halo or (C₁-C₈)alkoxy; W¹ is N or CR²²; and m3 is an integer of from 0 to 1. Each is equally preferred.

Within the embodiment compounds having the formula:

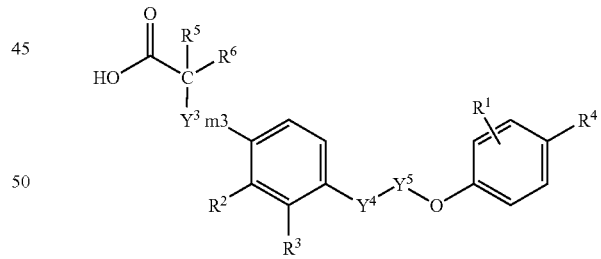

are preferred and compounds wherein R¹ is a member selected from the group consisting of:

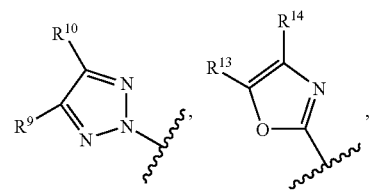

-continued

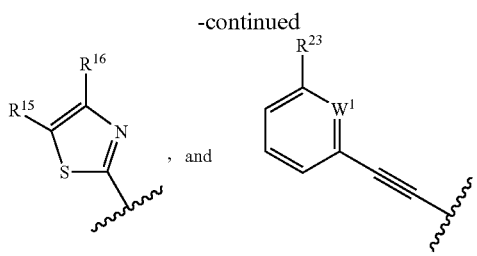

, and wherein the wavy line indicates the point of attachment to the rest of the molecule; each $R^9$ or $R^{10}$ is independently $CH_3$ or halo or is joined together with the triazole ring to form a triazolopyridine, benzotriazole or tetrahydrobenzotriazole ring optionally substituted with from one to two substituents independently selected from the group consisting of halo and $(C_1-C_8)$alkyl; each $R^{13}$ or $R^{14}$ is independently $CH_3$, halo or is joined together with the oxazole ring to form a benzoxazolyl ring, optionally substituted with from one to two $(C_1-C_8)$alkyl or halo substituents; each $R^{15}$ or $R^{16}$ is independently H, $(C_1-C_8)$alkyl, halo or $(C_1-C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, —$S(O)^{r1}R^7$, halo, $(C_1-C_8)$alkyl and $(C_1-C_8)$haloalkyl; $R^{23}$ is halo or $(C_1-C_8)$alkoxy; $W^1$ is N or $CR^{22}$ and m3 is an integer of form 0 to 1 is more preferred. Each of these $R^1$ substitutents are equally preferred.

When $R^1$ has the formula:

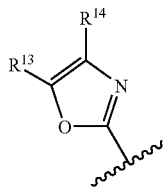

the compounds:

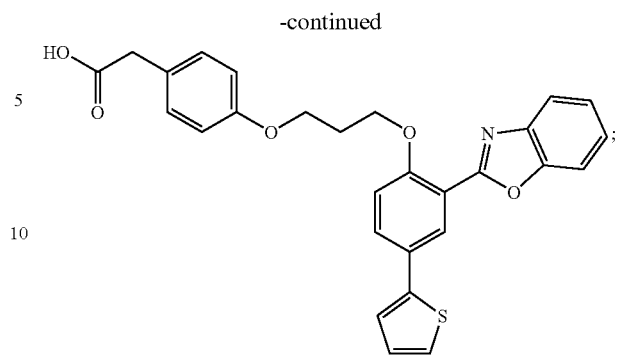

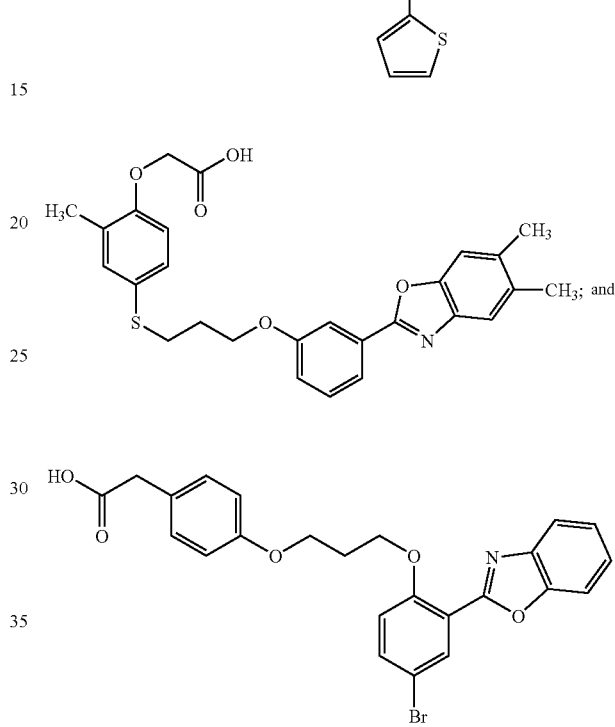

are especially preferred.

When $R^1$ has the formula:

the compounds:

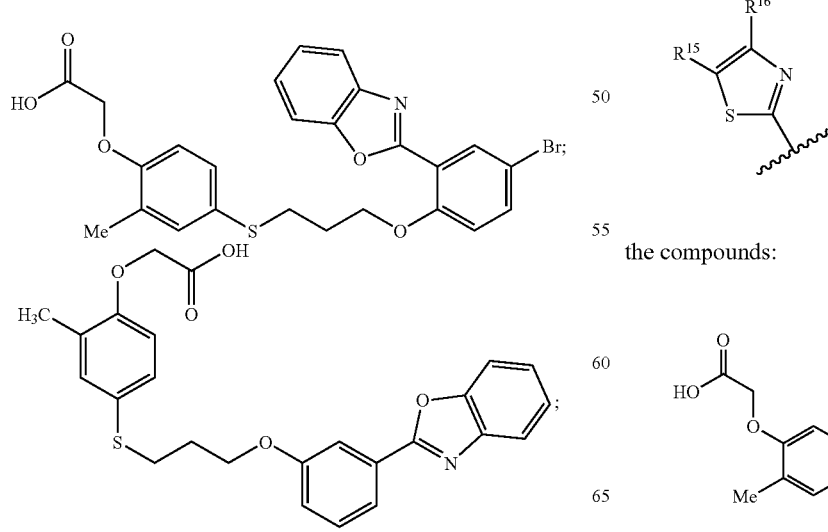

-continued

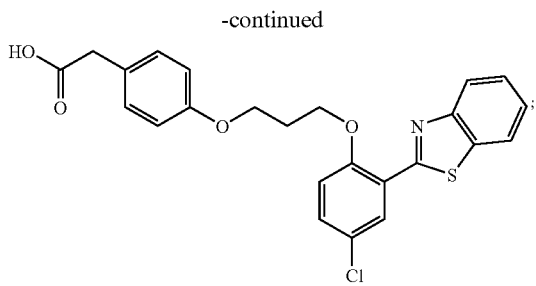

are especially preferred.

When R¹ has the formula:

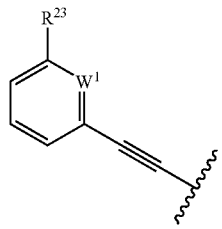

the compounds:

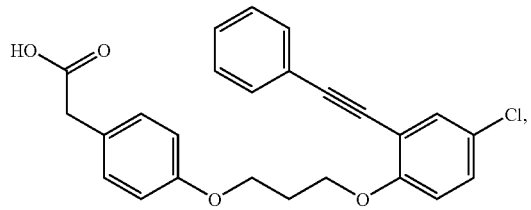

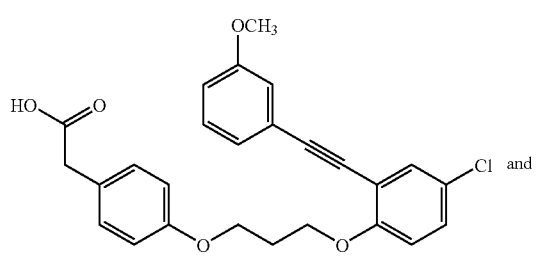

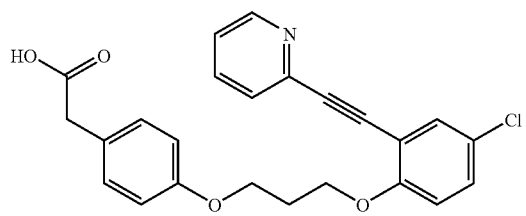

are especially preferred.

When R¹ has the formula:

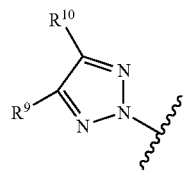

compounds having the formula:

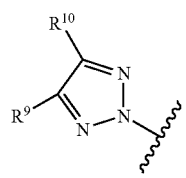

is preferred.

In another embodiment, when R¹ has the formula:

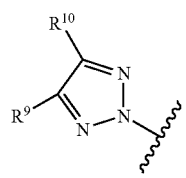

compounds having the formula:

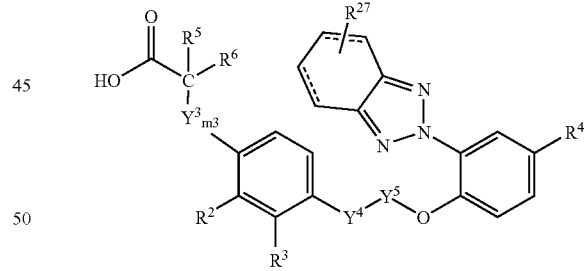

wherein
Y³ is —O— or —CR⁵R⁶—,
Y⁴ is a member selected from the group consisting of —O—, —S— and —CH₂—;
Y⁵ is —CH₂CH₂— or —CH₂CH₂CH₂—;
R² is independently H, ($C_1$-$C_8$)alkyl or halo;
R³ is a member independently selected from the group consisting of H, halogen, ($C_1$-$C_8$)alkyl and ($C_1$-$C_8$)alkoxy;
R⁴ is a member selected from the group consisting of H, halo, ($C_1$-$C_8$)alkyl, ($C_1$-$C_8$)alkoxy and 2-thiophenyl;
each R⁵ or R⁶ is independently H, ($C_1$-$C_8$)alkyl or ($C_1$-$C_8$)alkoxy,
R²⁷ is ($C_1$-$C_8$)alkyl or halo;

W³ is N, C or CH;
m3 is an integer of from 0 to 1; and
pharmaceutically acceptable salts, solvates, hydrates and prodrugs thereof are preferred.

In another embodiment, when R¹ has the formula:

[structure of triazole with R⁹, R¹⁰]

compounds having the formula:

[structure]

$Y^3$ is —O— or —CR⁵R⁶—,
$Y^4$ is a member selected from the group consisting of —O—, —S— and —CH₂—;
$Y^5$ is —CH₂CH₂— or —CH₂CH₂CH₂—;
$R^2$ is independently H, (C₁-C₈)alkyl or halo;
$R^3$ is a member independently selected from the group consisting of H, halogen and (C₁-C₈)alkyl;
$R^4$ is a member selected from the group consisting of H, halo, (C₁-C₈)alkyl, (C₁-C₈)alkoxy and 2-thiophenyl;
each $R^5$ and $R^6$ is independently H or (C₁-C₈)alkyl;
$R^{27}$ is (C₁-C₈)alkyl or halo;
$W^3$ is N, C or CH; and
m3 is an integer of from 0 to 1 are preferred
Within these embodiments, the compounds

[structure with Cl]

[structure with two Cl]

[structure with F]

[structure]

are preferred.

In other embodiments, compounds having the formula:

[structure]

wherein
$Y^3$ is —O— or —CHR⁶—,
each $R^5$ or $R^6$ is independently H, (C₁-C₈)alkyl or (C₁-C₈)alkoxy;
$R^4$ is a member selected from the group consisting of H, halo, (C₁-C₈)alkyl, (C₁-C₈)alkoxy and 2-thiophenyl;
$R^{27}$ is (C₁-C₈)alkyl or halo;
$W^3$ is N, C or CH;
m3 is an integer of from 0 to 1; and
pharmaceutically acceptable salts, solvates, hydrates and prodrugs thereof; are especially preferred.

Within this embodiment, compounds having the formula:

[structure]

wherein
$Y^3$ is —O— or —CHR⁶—,
each $R^5$ or $R^6$ is independently H or (C₁-C₈)alkyl,
$R^4$ is a member selected from the group consisting of H, halo, (C₁-C₈)alkyl, (C₁-C₈)alkoxy and 2-thiophenyl;

$R^{27}$ is $(C_1-C_8)$alkyl or halo;
$W^3$ is N, C or CH; and
m3 is an integer of from 0 to 1; are especially preferred
Within these embodiment, the compounds:
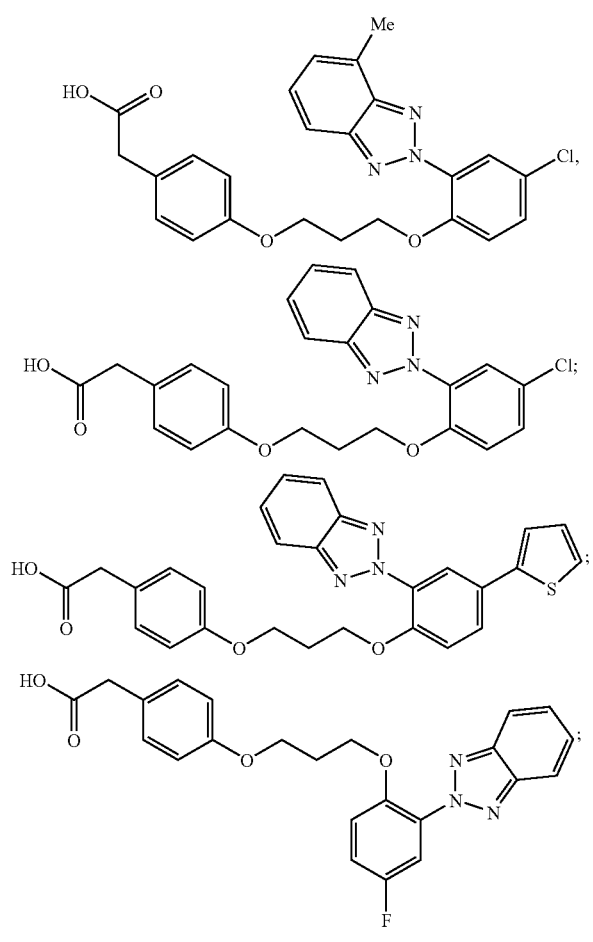
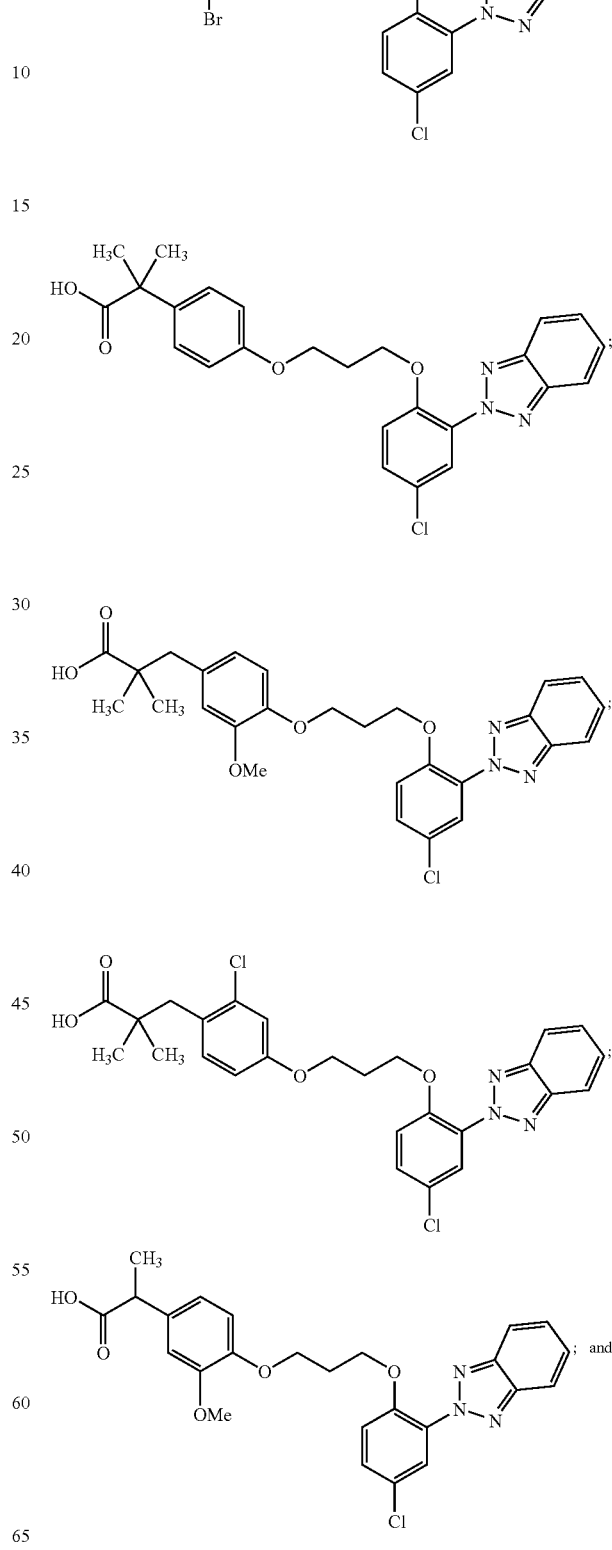

-continued

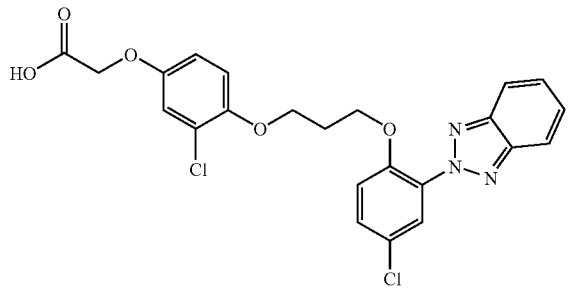

are especially preferred.

Figure 1B:
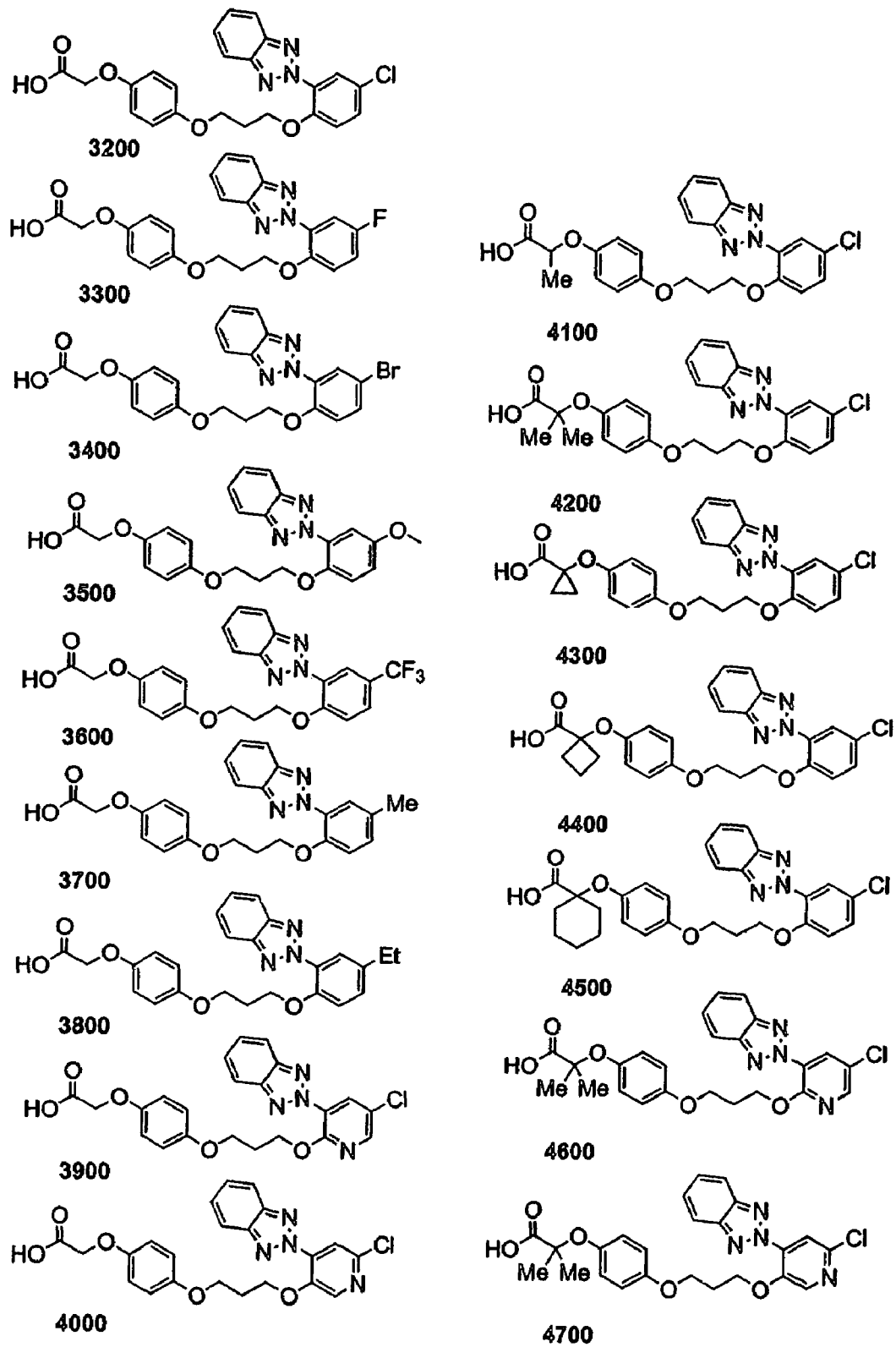
Figure 1C:
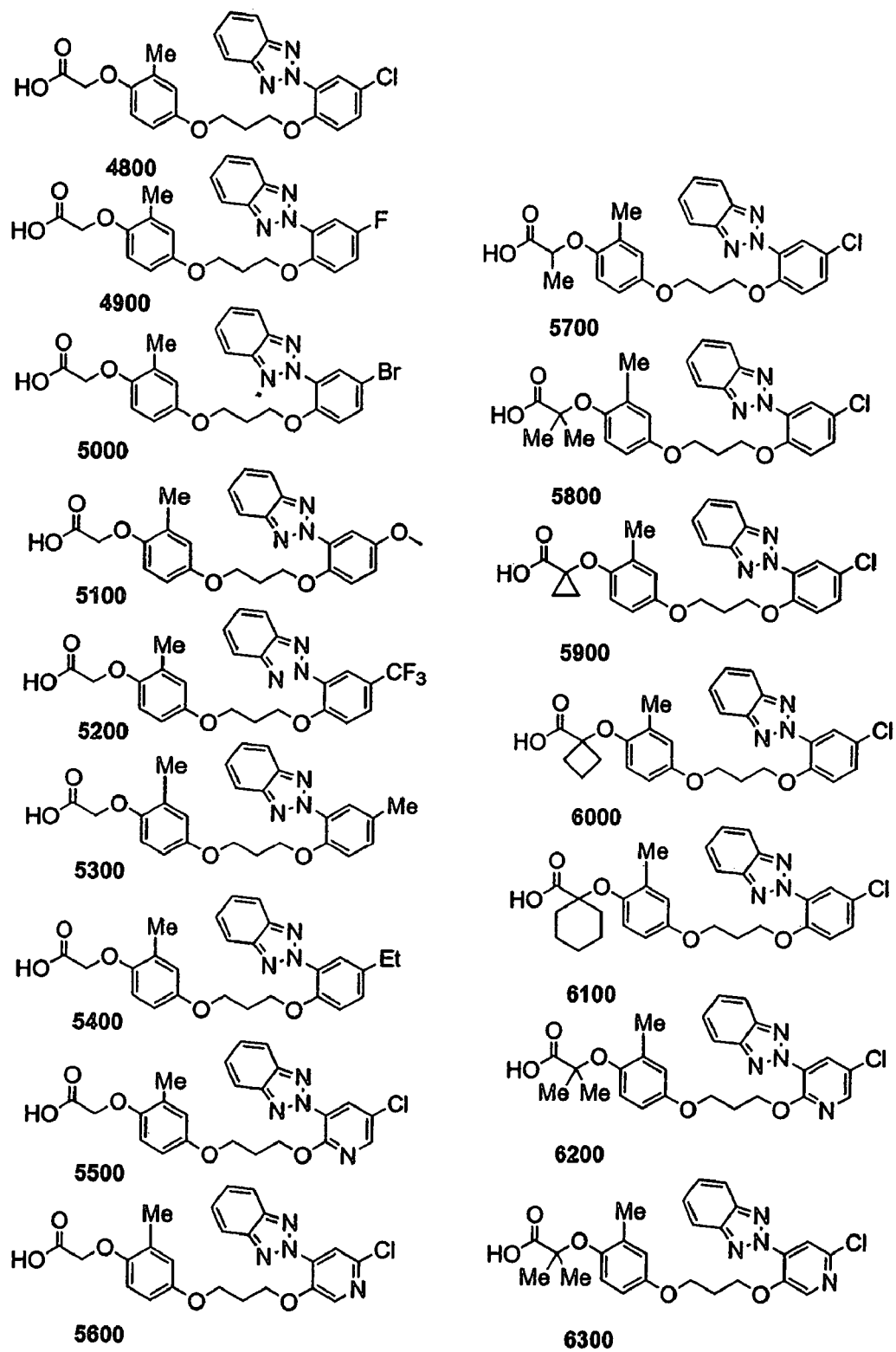
Figure 1D:
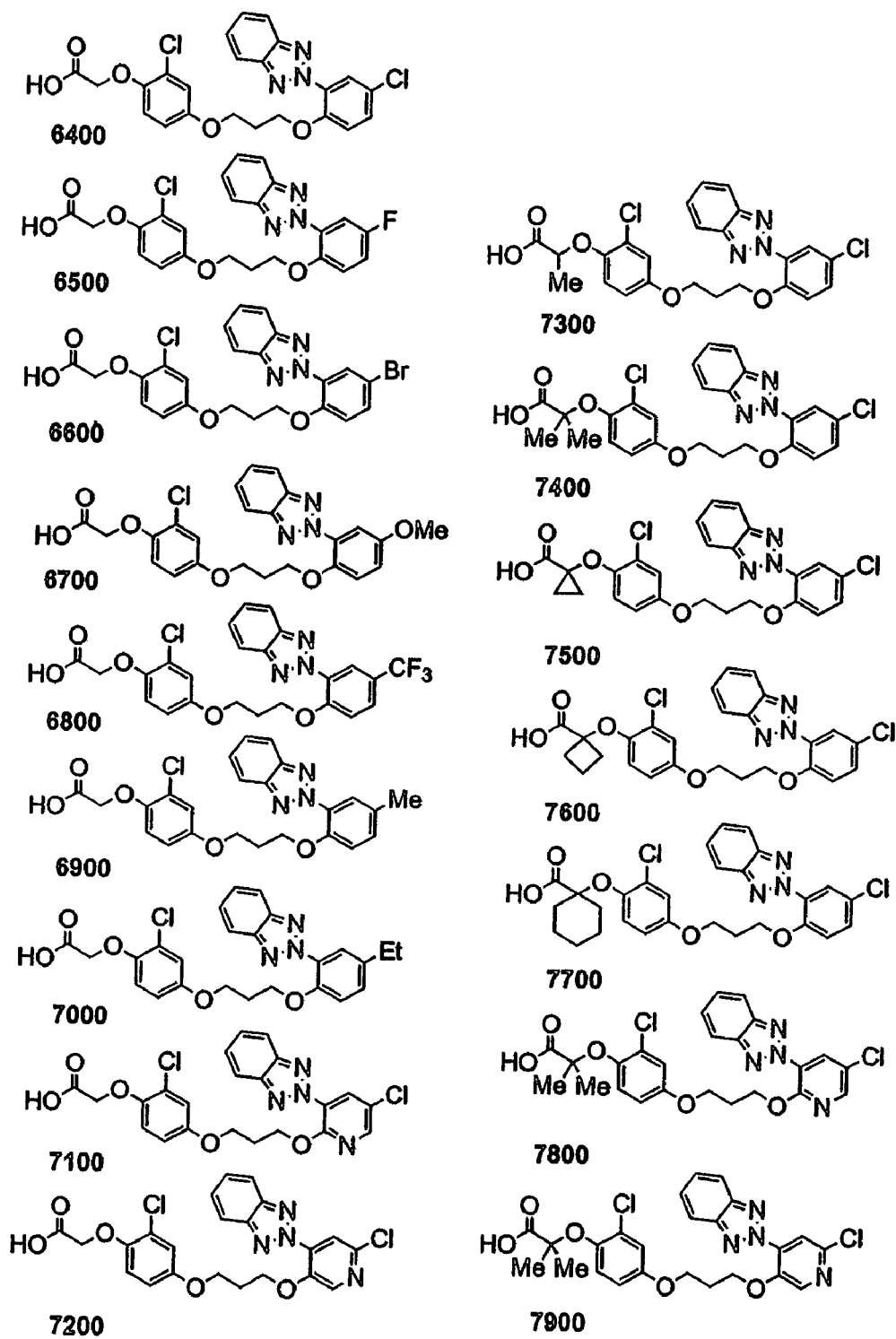
Figure 1E:
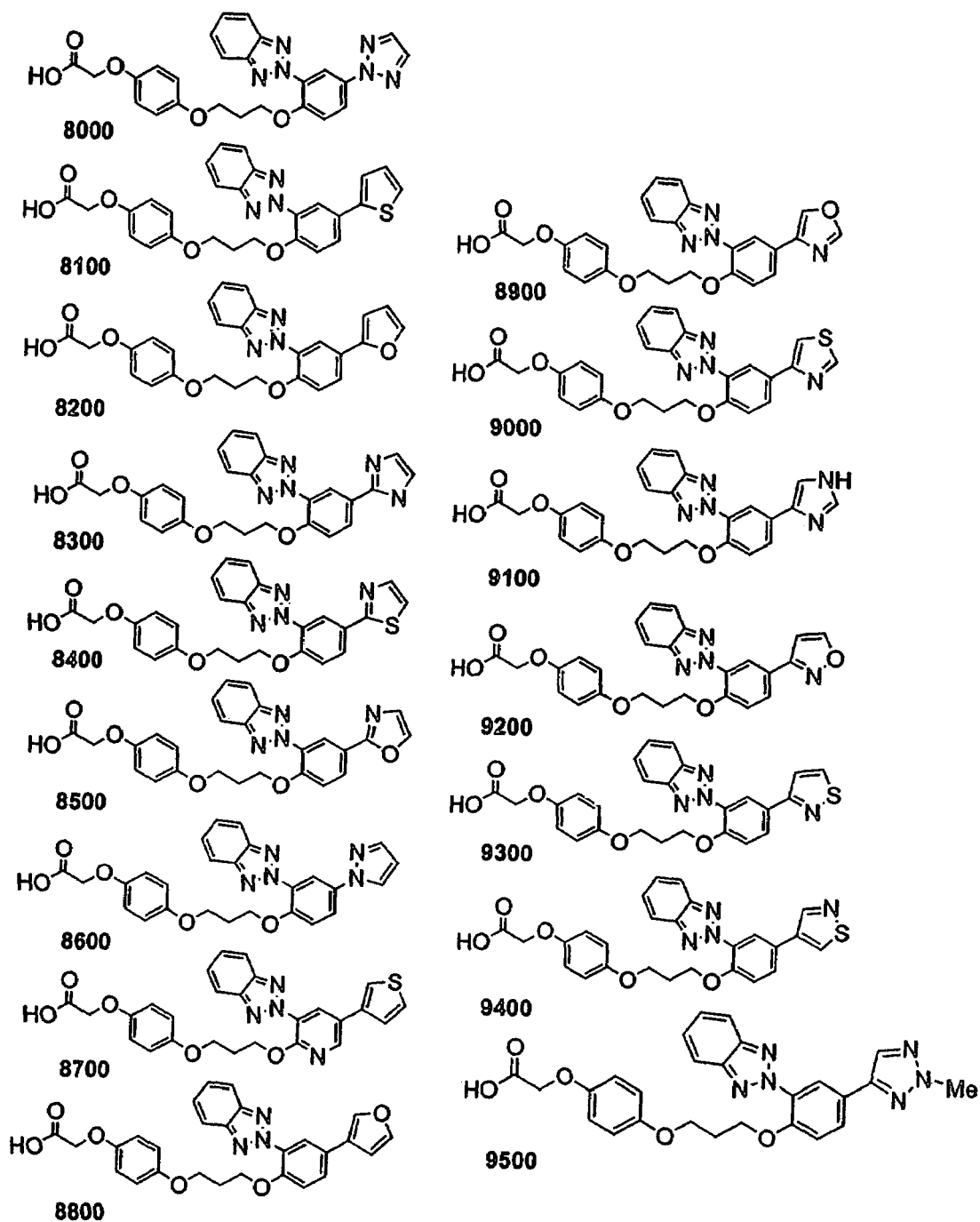
Figure 1F:
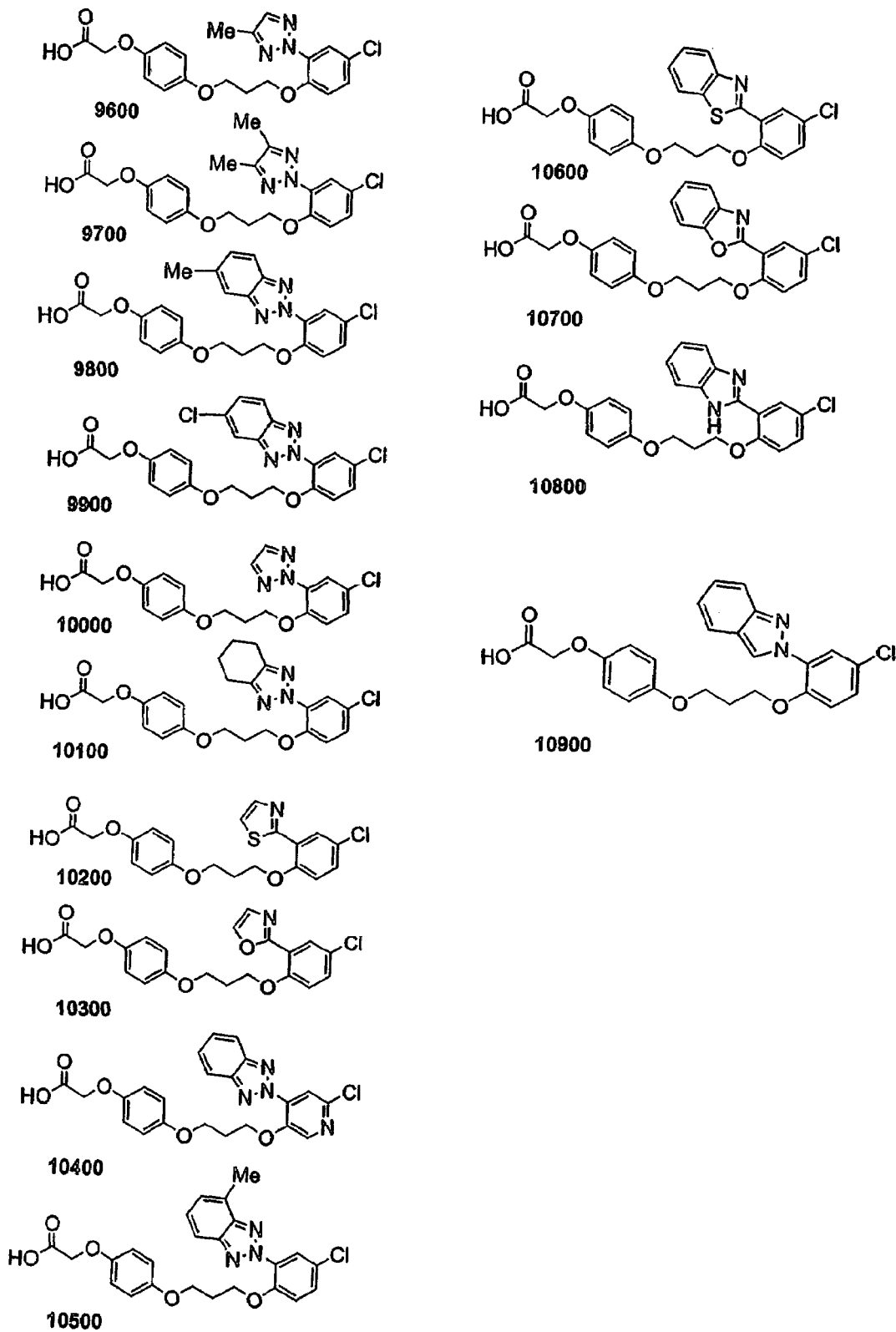
Figure 1G:
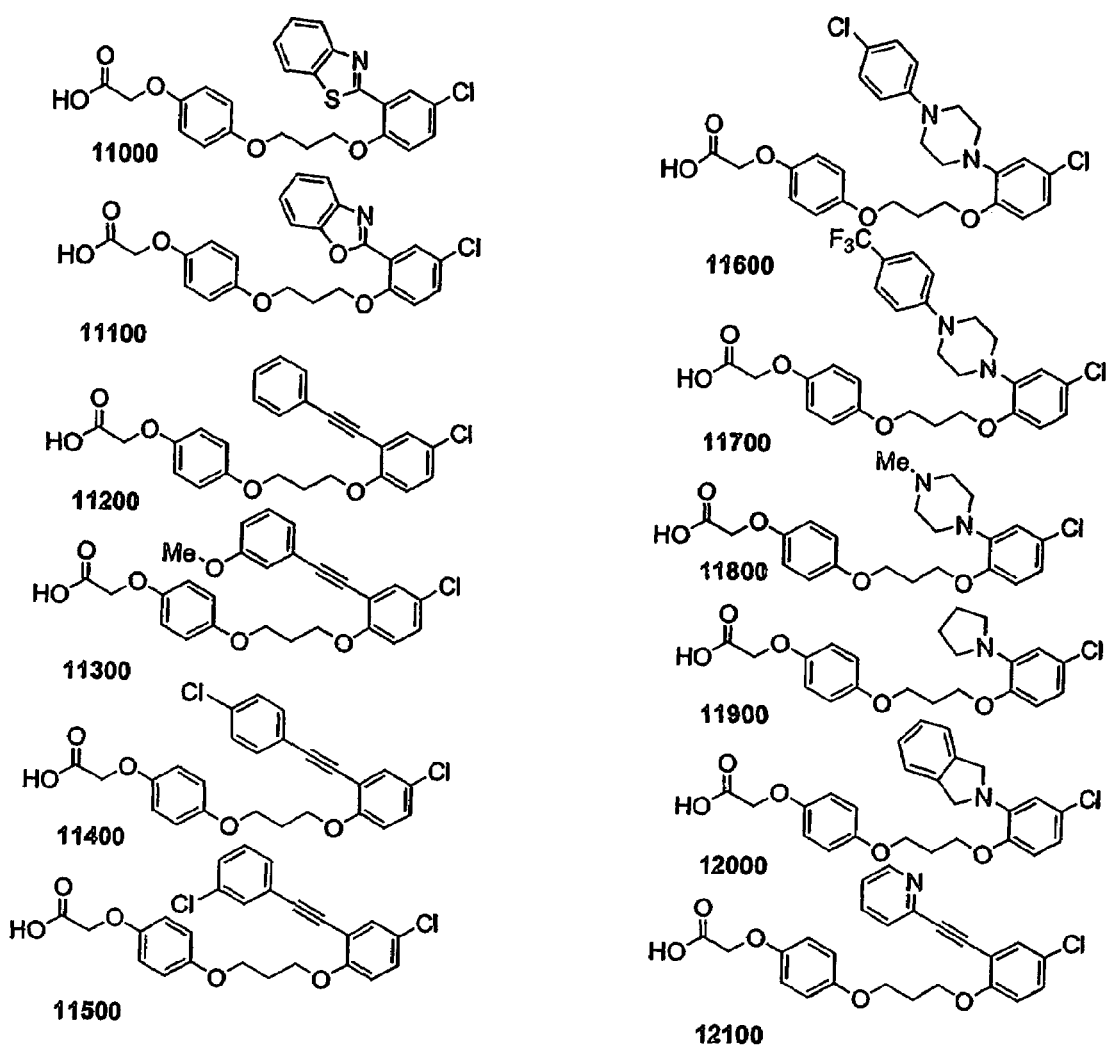
Figure 1H:
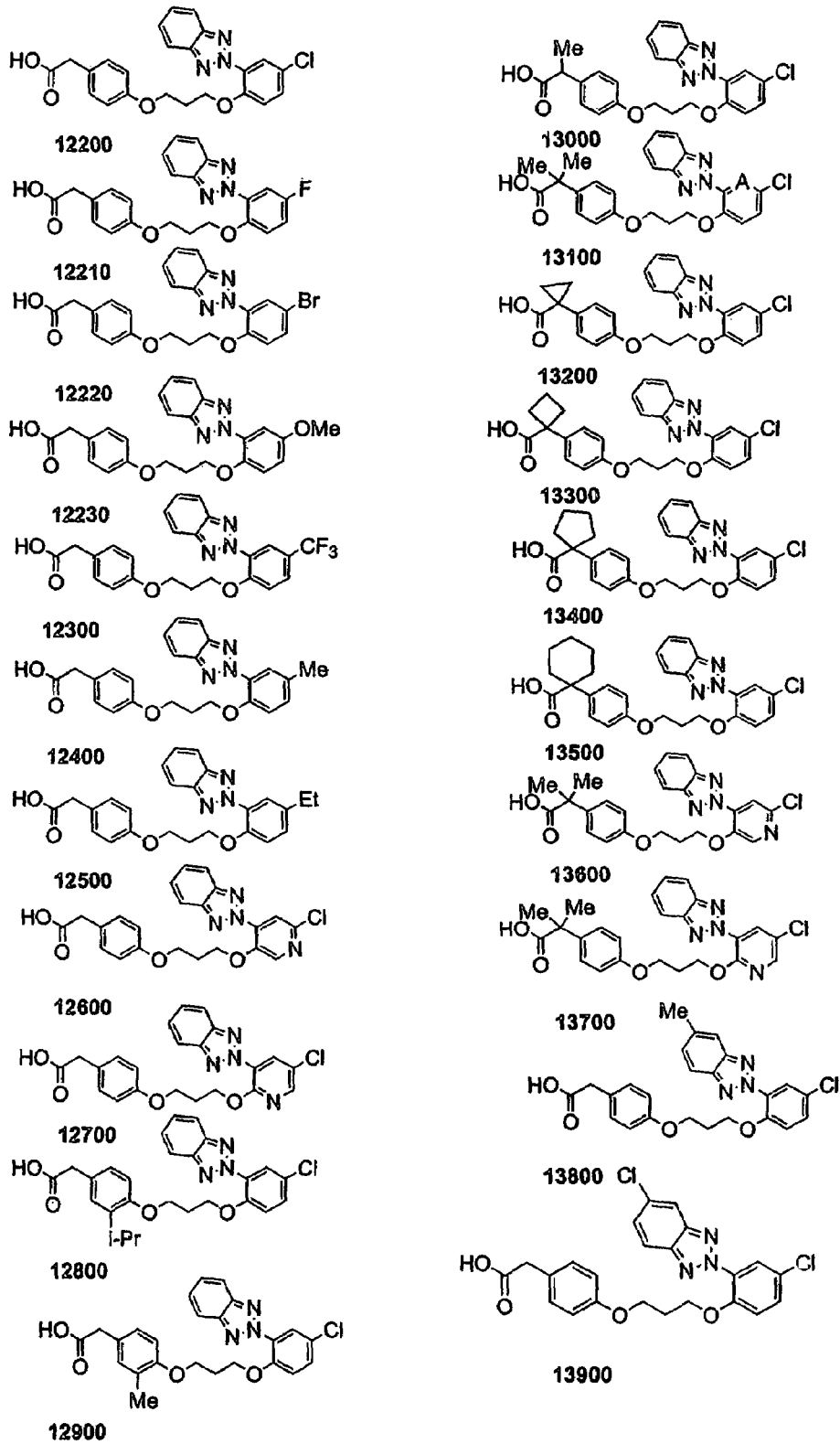
Figure 1I:
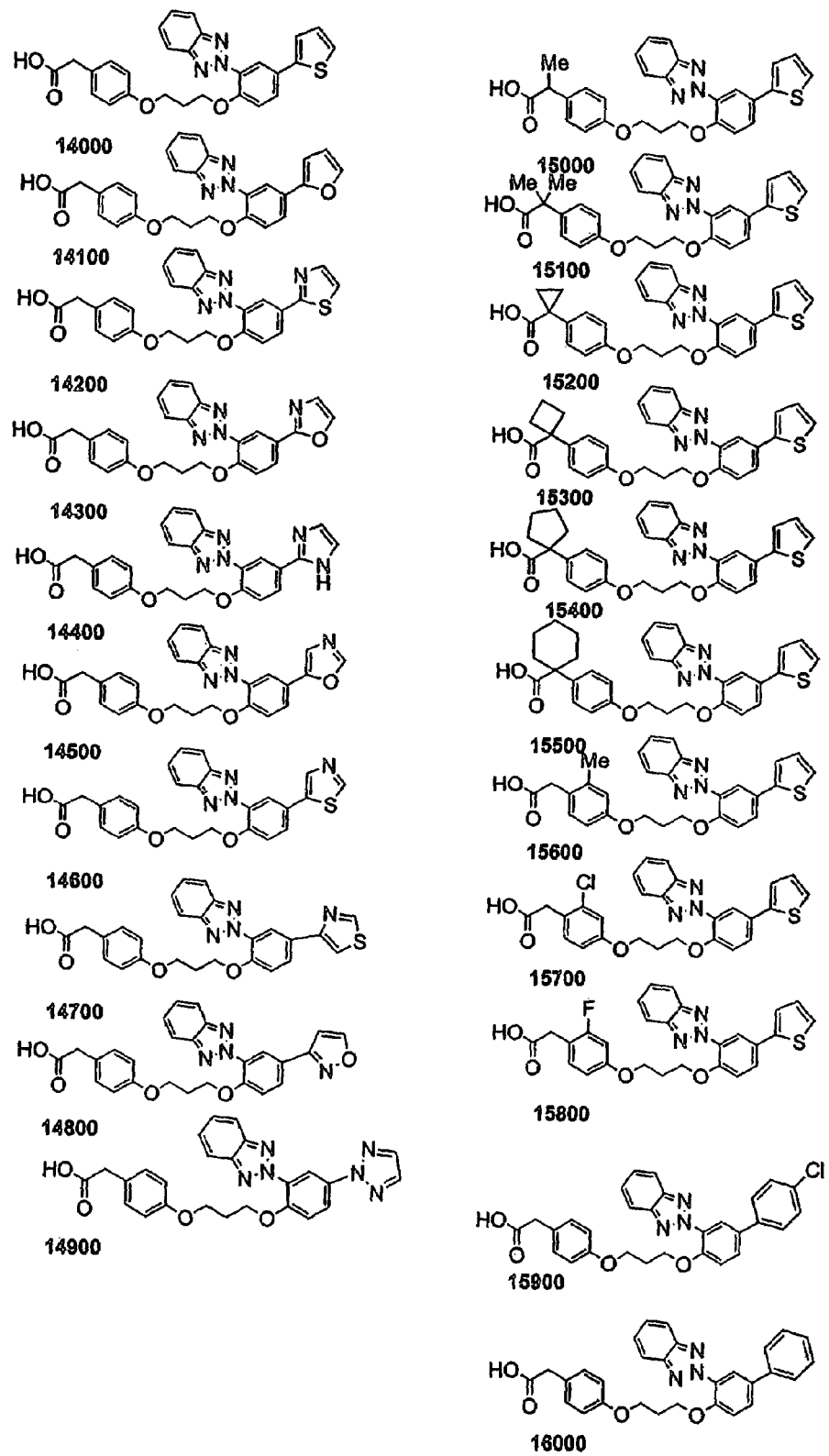
Figure 1J:
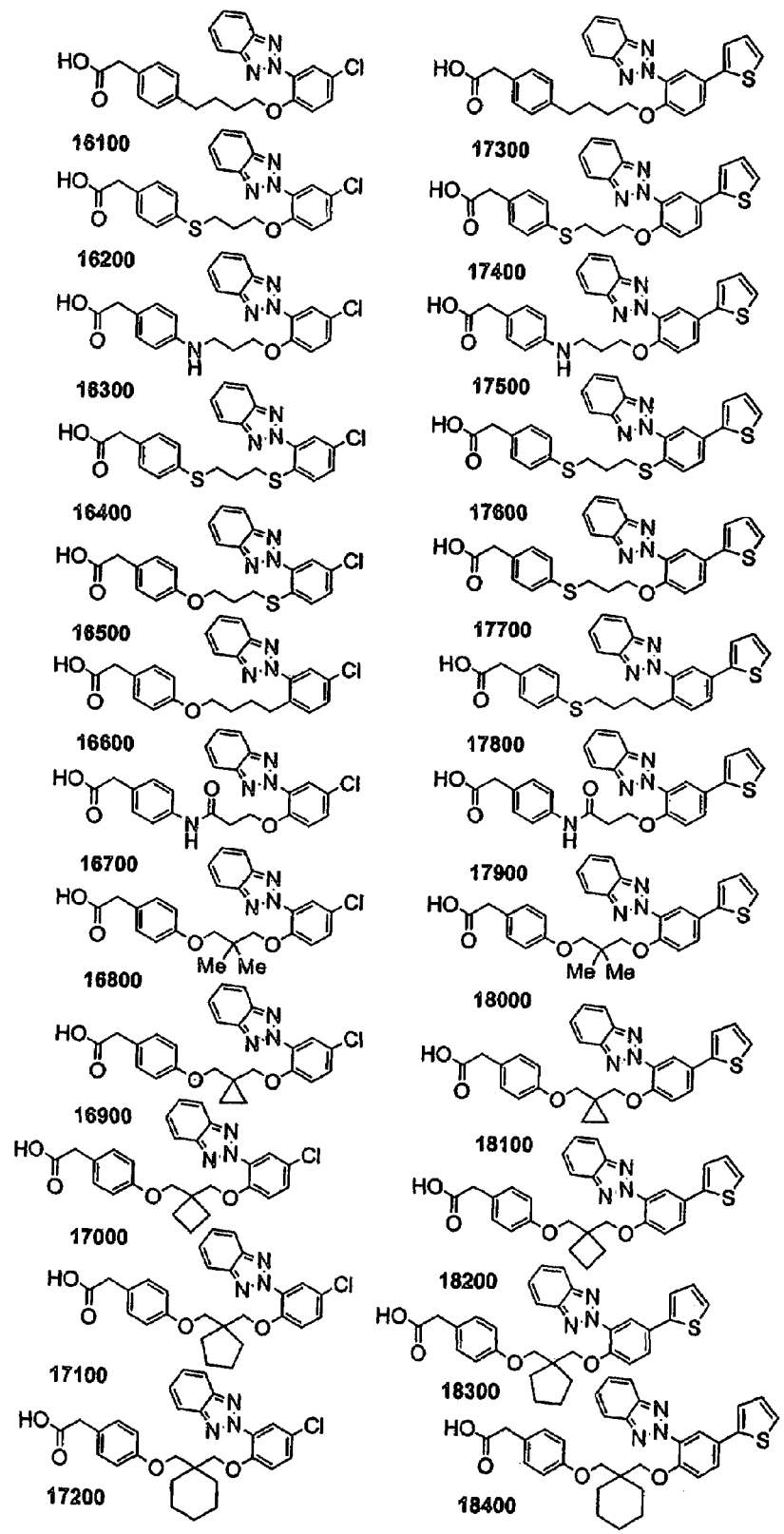
Figure 1K:
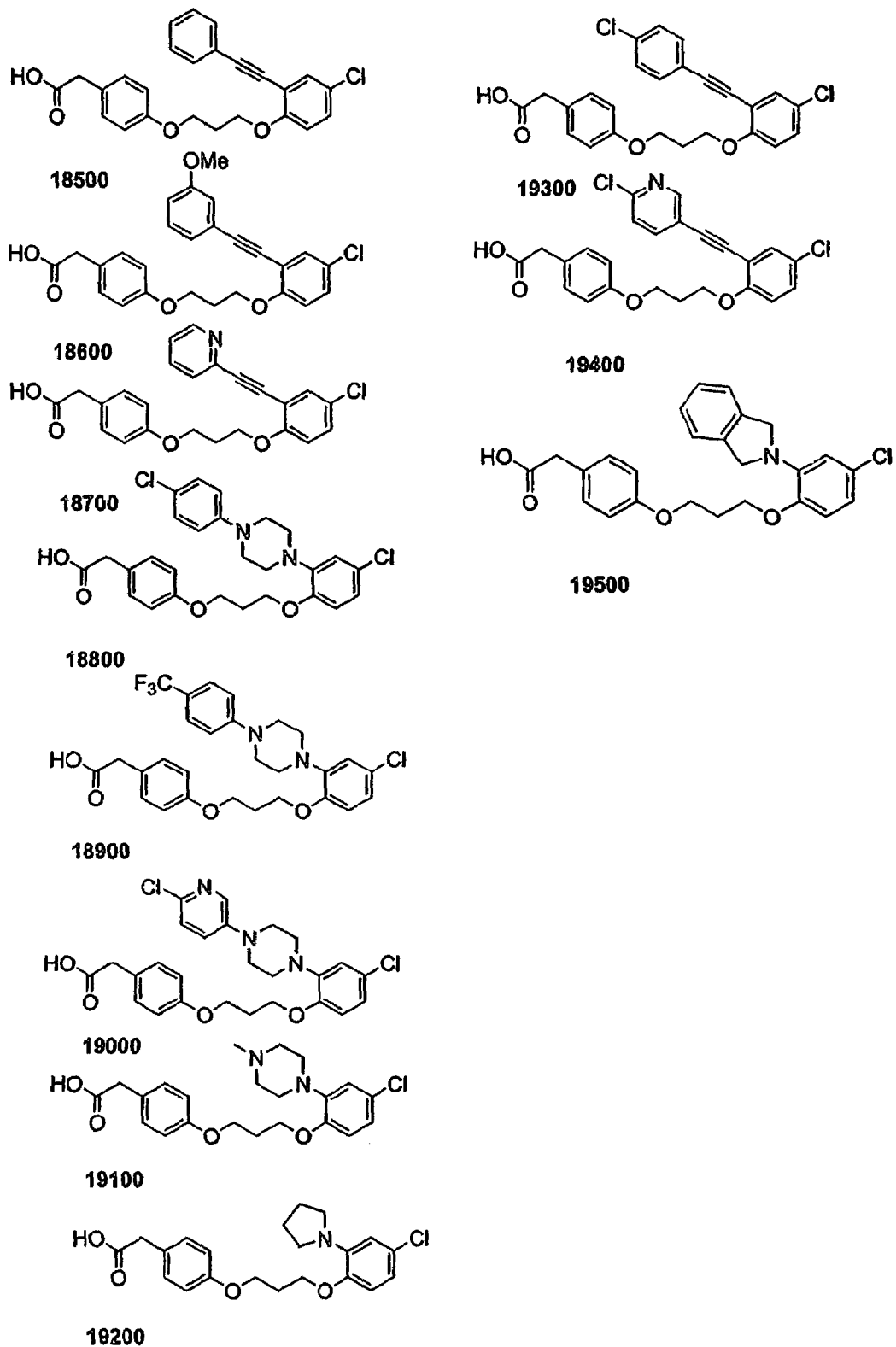
Figure 11:
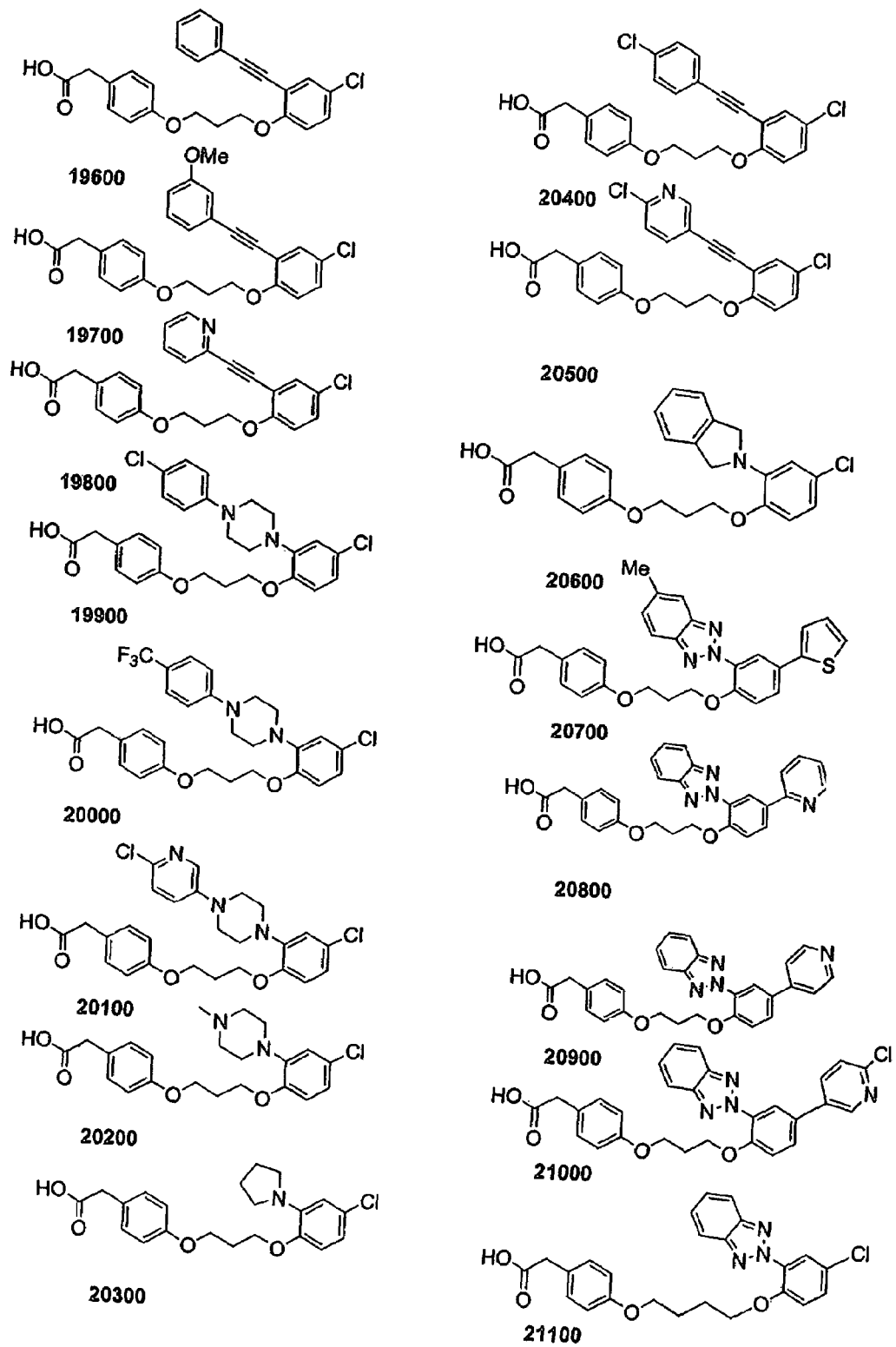

A variety of compounds have the desired activity. In particular, one group of preferred compounds are provided in FIG. 1.

Still other preferred groups of embodiments are provided in the Examples below. Examples of compounds of Formula 1 include:
{4-[3-(2-Benzotriazol-2-yl-4-chloro-phenoxy)-propylsulfanyl]-2-methyl-phenoxy}-acetic acid;
{4-[3-(2-Benzooxazol-2-yl-4-bromo-phenoxy)-propylsulfanyl]-2-methyl-phenoxy}-acetic acid;
{4-[2-(2-Benzotriazol-2-yl-4-chloro-phenoxy)-ethylsulfanyl]-2-methyl-phenoxy}-acetic acid;
{4-[3-(2-Benzotriazol-2-yl-4-chloro-phenoxy)-propoxy]-3-propyl-phenyl}-acetic acid;
{4-[3-(2-Benzotriazol-2-yl-4-chloro-phenoxy)-propoxy]-3-chloro-phenyl}-acetic acid;
{4-[2-(2-Benzotriazol-2-yl-4-chloro-phenoxy)-ethoxy]-phenyl}-acetic acid;
{4-[2-(2-Benzotriazol-2-yl-4-chloro-phenoxy)-ethoxy]-3-isopropyl-phenyl}-acetic acid;
(4-{3-[4-Chloro-2-(4,5,6,7-tetrahydro-benzotriazol-2-yl)-phenoxy]-propoxy}-phenyl)-acetic acid;
{4-[3-(4-Chloro-2-phenylethynyl-phenoxy)-propoxy]-phenyl}-acetic acid;
(4-{3-[4-Chloro-2-(3-methoxy-phenylethynyl)-phenoxy]-propoxy}-phenyl)-acetic acid;
{4-[3-(4-Chloro-2-pyridin-2-ylethynyl-phenoxy)-propoxy]-phenyl}-acetic acid;
(4-{3-[4-Chloro-2-(4-methyl-benzotriazol-2-yl)-phenoxy]-propoxy}-phenyl)-acetic acid;
{5-[3-(2-Benzotriazol-2-yl-4-chloro-phenoxy)-propoxy]-indazol-1-yl}-acetic acid;
{5-[3-(2-Benzotriazol-2-yl-4-chloro-phenoxy)-propoxy]-indol-1-yl}-acetic acid;
{5-[2-(2-Benzotriazol-2-yl-4-chloro-phenoxy)-ethoxy]-indol-1-yl }-acetic acid;
{5-[3-(3-Benzooxazol-2-yl-phenoxy)-propoxy]-indol-1-yl}-acetic acid;
{4-[3-(3-Benzooxazol-2-yl-phenoxy)-propylsulfanyl]-2-methyl-phenoxy}-acetic acid;
(4-{3-[3-(4,5-Dimethyl-oxazol-2-yl)-phenoxy]-propylsulfanyl}-2-methyl-phenoxy)-aceitc acid;
{1-[3-(2-Benzotriazol-2-yl-4-chloro-phenoxy)-propyl]-1H-indol-5-yloxy}-acetic acid;
4-[3-(2-Benzotriazol-2-yl-4-chloro-phenoxy)-propoxy]-3-chloro-benzoic acid;
{4-[3-(2-Benzotriazol-2-yl-4-chloro-phenoxy)-propoxy]-3-chloro-phenoxy}-acetic acid;
3-(3-Chloro-4-{3-[2-(4,5,6,7-tetrahydro-benzotriazol-2-yl)-phenoxy]-propoxy}-phenyl)-propionic acid;
3-(3-Chloro-4-{3-[4-chloro-2-(4,5,6,7-tetrahydro-benzotriazol-2-yl)-phenoxy]-propoxy}-phenyl)-propionic acid;
{4-[3-(2-Benzotriazol-2-yl-4-chloro-phenoxy)-propoxy]-phenoxy}-acetic acid;
{4-[3-(2-Benzotriazol-2-yl-4-thiophen-2-yl-phenoxy)-propoxy]-phenyl}-acetic acid;
[5-(2-Benzotriazol-2-yl-4-chloro-phenoxymethyl)-indol-1-yl]-acetic acid;
{4-[3-(2-Benzotriazol-2-yl-4-methoxy-phenoxy)-propoxy]-phenyl}-acetic acid;
(4-{3-[4-Chloro-2-(4-methyl-benzotriazol-2-yl)-phenoxy]-propoxy}-phenyl)-acetic acid ethyl ester;
{4-[3-(4-Chloro-2-phenylethynyl-phenoxy)-propoxy]-phenyl}-acetic acid ethyl ester;
(4-{3-[4-Chloro-2-(4,5,6,7-tetrahydro-benzotriazol-2-yl)-phenoxy]-propoxy}-phenyl)-acetic acid ethyl ester;
{4-[2-(2-Benzotriazol-2-yl-4-thiophen-2-yl-phenoxy)-ethoxy]-3-propyl-phenyl}-acetic acid ethyl ester;
{4-[3-(2-Benzotriazol-2-yl-4-chloro-phenoxy)-propoxy]-phenyl}-acetic acid methyl ester;
{4-[3-(2-Benzotriazol-2-yl-4-chloro-phenoxy)-propoxy]-phenyl}-acetic acid;
{4-[3-(2-Benzotriazol-2-yl-4-chloro-phenoxy)-propylsulfanyl]-2-methyl-phenoxy}-acetic acid ethyl ester;
{4-[3-(3-Benzooxazol-2-yl-phenoxy)-propylsulfanyl]-2-methyl-phenoxy}-acetic acid;
(4-{3-[3-(4,5-Dimethyl-oxazol-2-yl)-phenoxy]-propylsulfanyl}-2-methyl-acetic acid;
(4-{3-[4-Chloro-2-(4,5-dimethyl-[1,2,3]triazol-2-yl)-phenoxy]-phenoxy}-phenyl)-acetic acid;
{4-[3-(2-Benzooxazol-2-yl-4-bromo-phenoxy)-propoxy]-phenyl}-acetic acid;
{4-[3-(2-Benzotriazol-2-yl-4-fluoro-phenoxy)-propoxy]-phenyl}-acetic acid;
{4-[3-(2-Benzothiazol-2-yl-4-chloro-phenoxy)-propoxy]-phenyl}-acetic acid;
{4-[3-(2-Benzotriazol-2-yl-4-chloro-phenoxy)-propoxy]-3-methoxy-phenyl }-acetic acid;
{4-[3-(2-Benzotriazol-2-yl-4-chloro-phenoxy)-propoxy]-phenyl}-methoxy-acetic acid;
{4-[3-(2-Benzotriazol-2-yl-4-chloro-phenoxy)-propoxy]-3-Bromo-phenyl}-acetic acid;
{3-[3-(2-Benzotriazol-2-yl-4-chloro-phenoxy)-propoxy]-phenyl}-acetic acid;
2-{4-[3-(2-Benzotriazol-2-yl-4-chloro-phenoxy)-propoxy]-phenyl}-2-methyl-propionic acid;
2-{4-[3-(2-Benzotriazol-2-yl-4-chloro-phenoxy)-propoxy]-2-methyl-phenoxy}-2-methyl-propionic acid;
2-{4-[3-(2-Benzotriazol-2-yl-4-chloro-phenoxy)-propoxy]-2-chloro-phenoxy}-2-methyl-propionic acid;
2-{4-[3-(2-Benzotriazol-2-yl-4-chloro-phenoxy)-propoxy]-phenyl}-propionic acid;

{4-[3-(2-Benzooxazol-2-yl-4-thiophen-2-yl-phenoxy)-propoxy]-phenyl}-acetic acid;
(4-{3-[4-Fluoro-2-(4,5,6,7-tetrahydro-benzotriazol-2-yl)-phenoxy]-propoxy}-phenyl)-acetic acid;
(4-{3-[2-(4,5,6,7-Tetrahydro-benzotriazol-2-yl)-phenoxy]-propoxy}-phenyl)-acetic acid;
4-[3-(2-Benzotriazol-2-yl-4-chloro-phenoxy)-propoxy]-3-chloro-benzoic acid;
{4-[3-(2-Benzotriazol-2-yl-4-chloro-phenoxy)-propoxy]-3-chloro-phenoxy}-acetic acid;
3-(3-Chloro-4-{3-[2-(4,5,6,7-tetrahydro-benzotriazol-2-yl)-phenoxy]-propoxy}-phenyl)-propionic acid; and
3-(3-Chloro-4-{3-[4-chloro-2-(4,5,6,7-tetrahydro-benzotriazol-2-yl)-phenoxy]-propoxy}-phenyl)-propionic acid.
Particularly preferred compounds of the invention are: {4-[3-(2-Benzotriazol-2-yl-4-chloro-phenoxy)-propoxy]-phenyl}-acetic acid and {4-[3-(2-benzotriazol-2-yl-4-thiophen-2-yl-phenoxy)-propoxy]-phenyl}-acetic acid.

All the preferred and most preferred compounds listed above are selective hPPARδ agonists.

Preparations of Compounds of the Invention

The compounds of the present invention can be prepared in a number of ways familiar to one skilled in the art of organic synthesis. The compounds outlined herein can be synthesized using methods generally outlined in Scheme 1, along with methods typically utilized by a synthetic chemist and combinations or variations of those methods, which are generally known to one skilled in the art of synthetic chemistry. The synthetic route of compounds in the present invention is not limited to the methods outlined below. It is assumed one skilled in the art will be able to use the schemes outlined below to synthesized compounds claimed in this invention. Individual compounds may require manipulation of the condition in order to accommodate various functional groups. A variety of protecting groups generally known to one skilled in the art may be required. Purification, if necessary can be accomplished on a silica gel column eluted with the appropriate organic solvent. Also, reverse phase HPLC or recrystallization may be employed.

The compounds of formula (I) can be prepared using methods generally outlined in Scheme 1.

According to Scheme 1, electrophilic, aryl compounds of formula (I) (either commercially available or prepared according to known methods or methods outlined below in Scheme 3) are condensed with suitably substituted, nucleophilic aryl compounds ii generally in the presence of solvent and a non-nucleophilic base to provide target compound iii. Alternatively nucleophilic, aryl compounds of formula iv (either commercially available or prepared according to known methods or methods outlined below in Scheme 3) are condensed with suitably substituted, electrophilic aryl compounds v generally in the presence of solvent and a non-nucleophilic base to provide target compound iii. Examples of suitable non-nucleophilic bases include, but are not limited to, potassium carbonate, cesium bicarbonate, sodium hydride and the like.

The general synthesis schemes below are provided to illustrate the preparation of compounds of Formula (I) in which Z is a carboxylic acid or ester. For example, as shown in Scheme 2 aryl compounds vi (prepared as described below) are condensed with a substituted haloalkylether vii in the presence of cesium carbonate to provide target compounds viii. Similarly, aryl compounds ix (prepared as described below) are condensed with a substituted phenol x in the presence of cesium carbonate to provide target compounds viii. Compounds viii where $R^1$ is halogen can be converted into the corresponding amino-substituted compounds xi (e.g. $NR^2$=tetrahydroisoindoyl or 4-arylpiperidine) or alkynyl compounds xiii by treatment with an appropriately substituted amine or alkyne respectively. Compounds viii where $R^1$ is a benzotriazole can be converted into the corresponding tetrahydrobenzotriazole compounds xii via hydrogenation. Treatment of the target esters viii, xi, xii and xiii (Z=$CO_2R$) with lithium hydroxide converts the esters to carboxylic acid compounds viii, xi, xii and xiii (Z=$CO_2H$).

Scheme 1

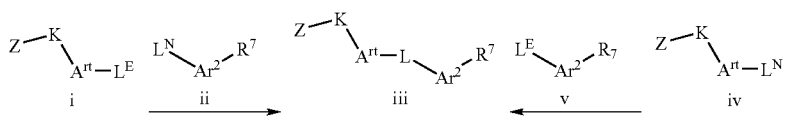

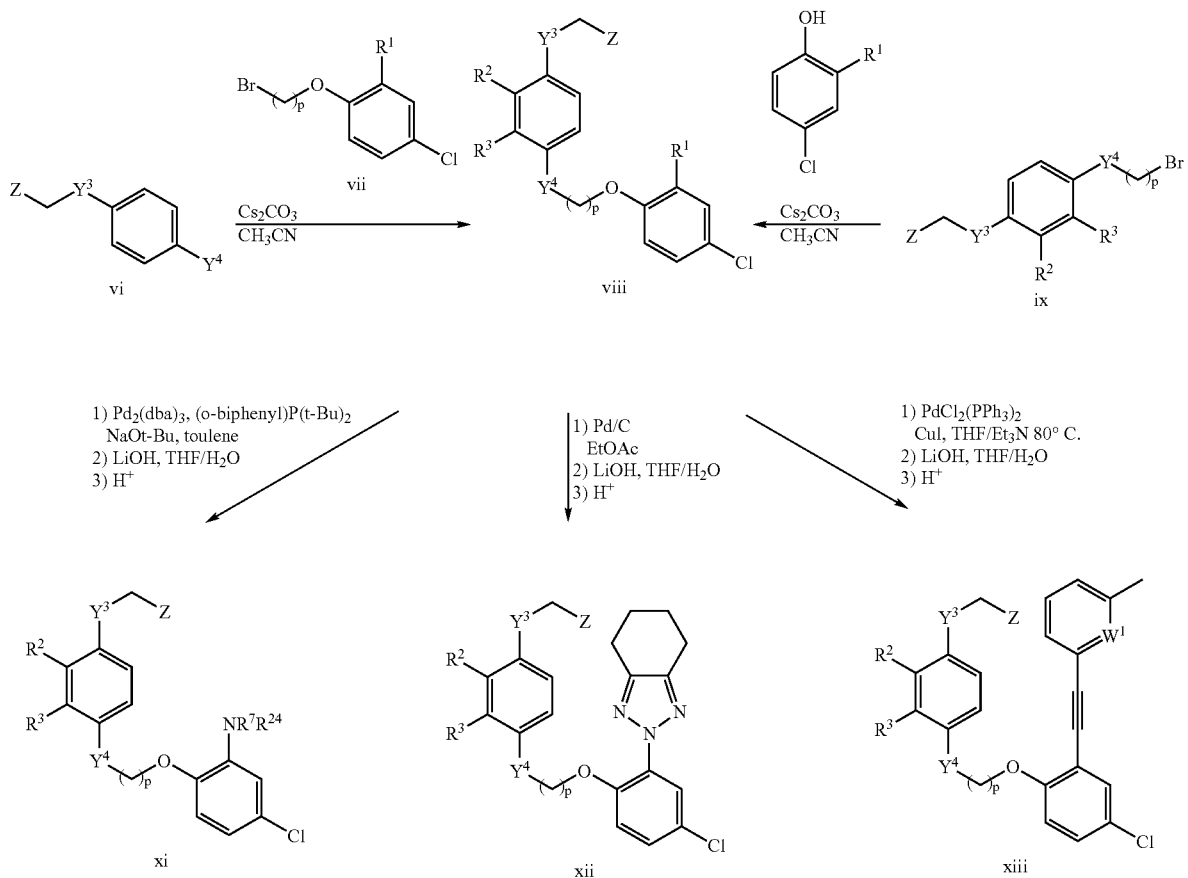

As shown in Scheme 3, compounds of formula (I) wherein $R^1$ is aryl can be 5 prepared by treating 4-chloro-aryl compound xiv with 2-thiophene boronic acid to provide aryl substituted compounds, xv.

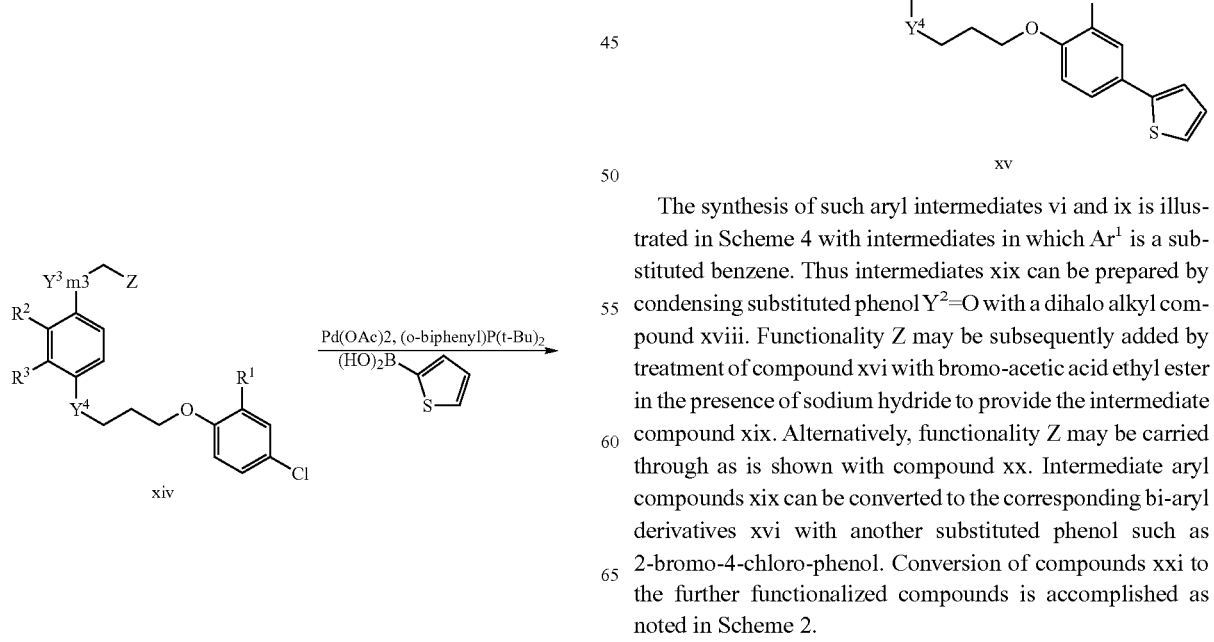

The synthesis of such aryl intermediates vi and ix is illustrated in Scheme 4 with intermediates in which $Ar^1$ is a substituted benzene. Thus intermediates xix can be prepared by condensing substituted phenol $Y^2$=O with a dihalo alkyl compound xviii. Functionality Z may be subsequently added by treatment of compound xvi with bromo-acetic acid ethyl ester in the presence of sodium hydride to provide the intermediate compound xix. Alternatively, functionality Z may be carried through as is shown with compound xx. Intermediate aryl compounds xix can be converted to the corresponding bi-aryl derivatives xvi with another substituted phenol such as 2-bromo-4-chloro-phenol. Conversion of compounds xxi to the further functionalized compounds is accomplished as noted in Scheme 2.

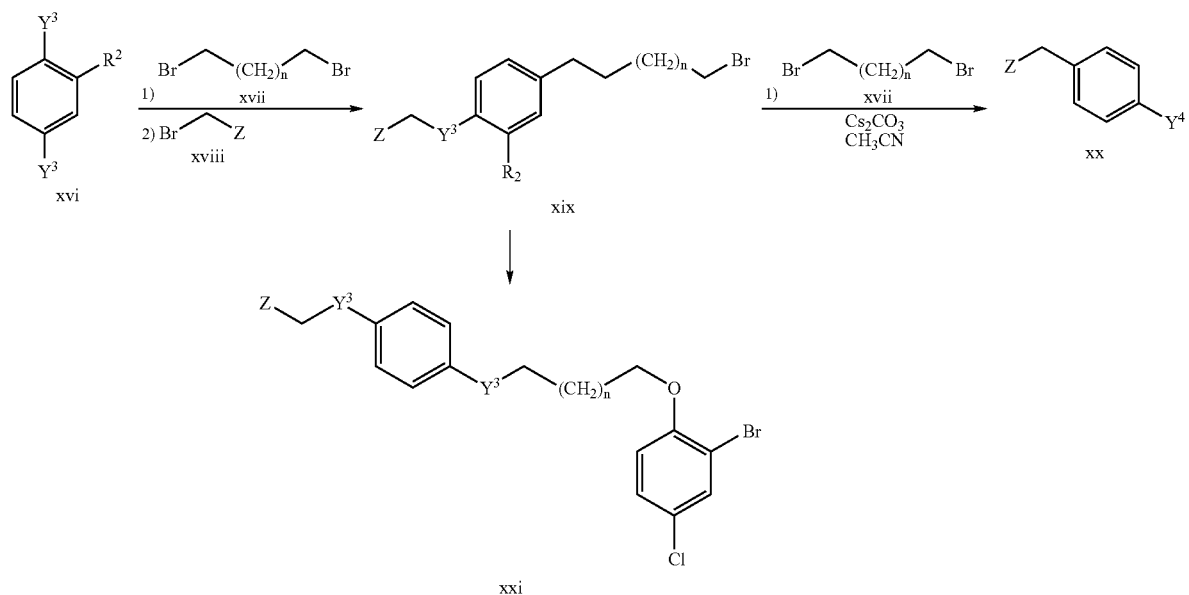
Alternatively as outlined in Scheme 5, compounds of formula xxii can be converted into intermediate xxiii by treatment with a dihaloalkyl compound to form haloalkylether derivative xxiii. This route is particularly useful to form intermediates of formula viii in Scheme 2 which have $Ar^2$ rings functionalized with different $R^1$ groups.
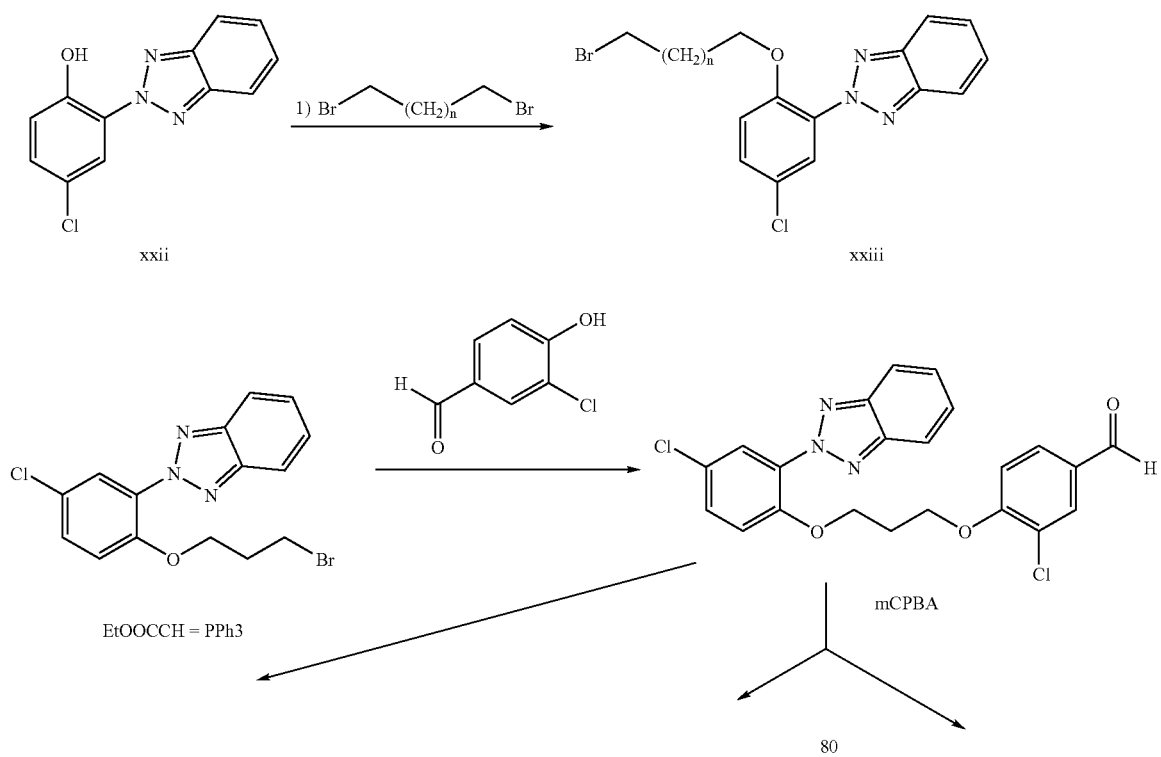

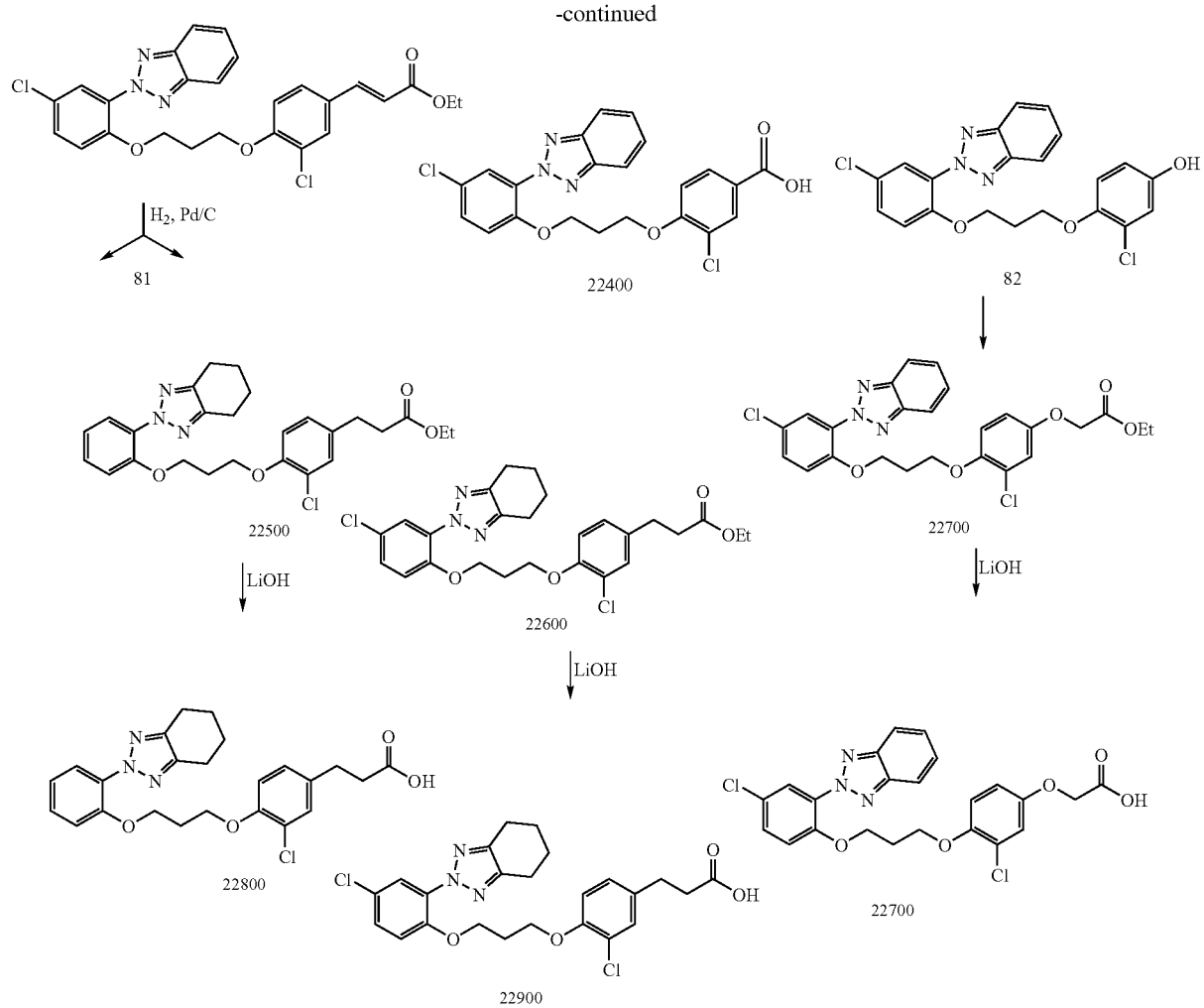

By using the methods outlined above, target compounds with linking groups of different lengths and functionality can be prepared. Thus, structural isomers, having the $Y^3$ attached at either the 2- or 3-position relative to the phenol hydroxyl group in compound x can be prepared from the corresponding 2- or 3-mercaptophenols.

Still further, the general schemes outlined in Schemes 1-5 can be used to prepare compounds of Formula (I) in which $Ar^2$ is another ring. To obtain these compounds, the phenols are replaced by the corresponding hydroxy-substituted ring.

Likewise, the general schemes outlined in Schemes 1-5 can be used to prepare compounds of Formula (I) in which L or K is an alternatively functionalized linking group. To obtain these compounds, mercapto phenols may be replaced with halo phenols or halothiophenols and the resulting halogenated aryl intermediates can be coupled with haloalkyl moieties to give alkyl linking groups.

Likewise, related compounds with different $Ar^1$ and $Ar^2$ rings and different lengths and substitution of linkers L and K can be prepared in a similar manner beginning with appropriately substituted aryl compounds many of which are available from commercial sources or can be prepared according to literature methods. More specific details are provided in the examples below. In each of Schemes 1-5, reaction conditions (e.g., amounts of reactants, solvents, temperatures and workup conditions) can be selected using the Examples below as a guide.

Preparation of Alcohols, Ethers, Nitrites, Amides/Imides and Aldehydes

The above general synthesis schemes are provided to illustrate the prepared of compounds of Formula (I) in which Z is a carboxylic acid or ester. Conversion of each of these groups into the corresponding alcohols, ethers, nitrites, amides/imides or aldehydes can be accomplished using methods generally known to one of skill in the art. Several methods for reduction (and oxidation) are provided below as illustrative of the processes used in preparing additional compounds of the invention.

Conversion of Carboxylic Acids into Alcohols, Ethers, Nitrites, Amide/Imides and Aldehydes.

The carboxylic acids of this invention can be converted into the corresponding alcohols, ethers, nitrites, amides/imides and aldehydes by a number of methods, including the routes A-D shown in Scheme 6. The method to be used in a given case depends on the nature of R and the substituents thereon. A variety of useful methods are described in Larock, COMPREHENSIVE ORGANIC TRANSFORMATIONS, VCH Publishers Inc, New York (1989). In particular, methods are described for converting acyl chlorides 32 to aldehydes 33 (p 620), esters 31 to aldehydes 33 (p 621), esters 31 to carbinols 35 (p 549), carboxylic acids 31 to carbinols 35 (p 548), esters 31 to amides/imides 34 (p 987) and esters 31 to nitrites 36(p 988).

In method A, Scheme 6, a carboxylic acid 31 is first converted into the corresponding acid chloride 32. This transformation is effected by reacting the acid 31 with oxalyl chloride, phosphorus pentachloride or, preferably, thionyl chloride. The reaction is conducted in an aprotic solvent such as dichloromethane, tetrahydrofuran or, preferably, 1,2-dichloroethane. The acid chloride 32 is then converted into the aldehyde 33 by chemical reduction, such as by the use of sodium borohydride in DMF at −70° C., as described in Tetrahedron Lett. 22:11 (1981) or, more preferably by hydrogenation using 5% palladium on barium sulfate as catalyst (see, for example, *J. Amer. Chem. Soc.*, 108:2608 (1986)). The reaction is conducted in an aprotic solvent such as toluene or, preferably, xylene. The aldehyde 33 is converted into the carbinol 35 by reduction, for example by reaction with 9 BBN, lithium aluminum tritertiarybutoxy hydride or more preferably sodium borohydride, (see, *J. Amer. Chem. Soc.* 71:122 (1949)). The reaction is conducted in a protic solvent such as ethanol or preferably, isopropanol.

Alternatively ester 31 can be converted directly into the aldehyde 3 by reduction, for example, by the use of sodium aluminum hydride or preferably, diisobutyl aluminum hydride (see e.g., *Synthesis*, 617 (1975)). The reaction is conducted in a non-polar solvent such as benzene or, preferably, toluene.

In method B, Scheme 6, ester 31 is converted into the amide/imide 34 by transesterification with hydroxypyridine and the corresponding amine (see, *J.C.S.C.* 89 (1969)). The reaction is conducted in an ethereal solvent such as dioxane or, preferably, tetrahydrofuran.

In method C, Scheme 6, ester 31 is converted into the carbinol 35 by reduction with lithium aluminum hydride or, preferably, with lithium borohydride (see, *J. Amer. Chem. Soc.*, 109:1186 (1987)). The reaction is conducted in an ethereal solvent such as dioxane or, preferably, tetrahydrofuran.

Alternatively, carboxylic acid 31 can be converted into the carbinol 35. This conversion is effected by reacting the carboxylic acid with a reducing agent such as lithium aluminum hydride or, preferably, with diborane, as described in ORGANIC SYNTHESES, 64:104 (1985). The reaction is conducted in an ethereal solvent such as dioxane or, preferably, tetrahydrofuran.

The carbinol 35 ($R^6$=H) can be converted into the ether 35 ($R^6$=$C_1$-$C_8$). This transformation is effected by an alkylation reaction, for example by reacting the carbinol 35 with an alkyl chloride ($C_1$-$C_8$)Cl. The reaction is conducted in an aprotic solvent such as dichloromethane or, preferably, tetrahydrofuran, in the presence of an organic base such as triethylamine or, preferably, pyridine.

In method D, Scheme 6, the ester 31 is converted into the nitrile 36. This conversion is effected by reacting the ester with a dehydrating agent such as dimethylaluminum nitride as described in *Tett. Lett.*, 4907 (1979).

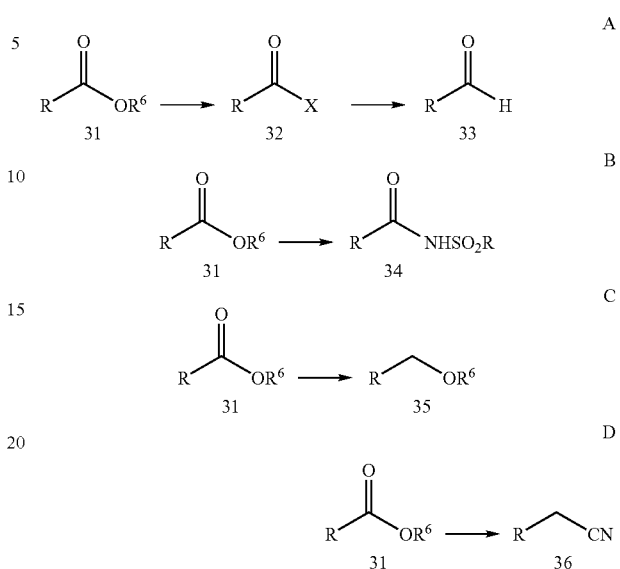

Scheme 6

Furthermore, the tetrazole derivatives may be conveniently prepared by a general process wherein a compound like 36 is coupled to an alcohol using the Mitsunobu protocol (*Synthesis* 1, (1981)).

Not all compounds of formula 1 may be compatible with some of the reaction conditions described in the Examples. Such restrictions are readily apparent to those skilled in the art of organic synthesis and alternative methods must then be used.

Isomeric Compounds

Certain of the compounds of the present invention possess one or more chiral centers and each center may exist in the R or S configuration. The present invention includes all diastereomeric, enantiomeric and epimeric forms as well as the appropriate mixtures thereof. For many compounds of the present invention, a single chiral center is present (at the carbon atom bearing $R^2$), resulting in racemic mixtures of enantiomers. As noted above, the present invention further includes compounds, compositions and methods wherein a single isomer (or single enantiomer) is provided or used. Methods of preparing chiral compounds are provided in the Examples. Alternatively, mixtures of enantiomers can be separated into their individual isomers via methods known in the art such as salt formation and crystallization with chiral bases, chiral chromatography (e.g., HPLC using commercially available columns for chiral resolution) and via methods such as simulated moving bed chromatography (see, for example, U.S. Pat. No. 5,518,625).

In certain preferred embodiments of the invention, the (−)-isomer of the compound of formula (I) is used, which is substantially free of its (+)-isomer. In this context, "substantially free" refers to a compound that is contaminated by less than about 20%, more preferably 10%, still more preferably 5%, even more preferably 2% and most preferably less than about 1% of the undesired isomer. In other preferred embodiments of the invention, the (+)-isomer of the compound of formula (I) is used, which is substantially free of its (−)-isomer.

Additionally, the compounds of the present invention may exist as geometric isomers. The present invention includes all cis, trans, syn, anti, entgegen (E) and zusammen (Z) isomers as well as the appropriate mixtures thereof.

In some situations, compounds may exist as tautomers. All tautomers are included within formula (I) and are provided by this invention.

Solvate Forms of the Compounds of the Invention

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention.

Prodrug Forms of the Compounds of the Invention

In some embodiments, the compounds of the invention are present in a prodrug form. In particular, the invention also provides, for example, compounds of Formula (I) in which $CO_2H$ is esterified to form $—CO_2R^6$, wherein $R^6$ is a member selected from the group consisting of H, $(C_1-C_8)$alkyl, halo $(C_1-C_8)$alkyl, $—X^4OR^2$, $—X^4NR^2R^3$, $(C_2-C_8)$alkenyl, $(C_3-C_7)$cycloalkyl, heterocyclyl, aryl$(C_1-C_4)$alkyl and aryl$(C_2-C_8)$alkenyl.

$R^2$ and $R^3$ are members independently selected from the group consisting of H, $(C_1-C_8)$alkyl, halo$(C_1-C_8)$alkyl, $—X^3OR^9$, aryl, aryl$(C_1-C_4)$alkyl and heteroaryl or optionally, if both are present on the same substituent, may be joined together to form a three- to eight-membered ring. Each $X^3$ and $X^4$ are members independently selected from the group consisting of $(C_1-C_4)$alkylene, $(C_2-C_4)$alkenylene and $(C_2-C_4)$alkynylene.

Esters of the compounds of the present invention may be prepared as described herein or according to conventional methods.

Pharmaceutical Compositions and Methods of Treating Diseases and Conditions

In accordance with the present invention, a therapeutically effective amount of a compound of Formula (I) can be used for the preparation of a pharmaceutical composition useful for treating diabetes, treating hyperlipidemia, treating hyperuricemia, treating obesity, lowering triglyceride levels, lowering cholesterol levels, raising the plasma level of high density lipoprotein and for treating, preventing or reducing the risk of developing atherosclerosis.

The compositions of the invention can include compounds of Formula (I), pharmaceutically acceptable salts thereof or a hydrolysable precursor thereof. In general, the compound is mixed with suitable carriers or excipient(s) in a therapeutically effective amount. By a "therapeutically effective dose", "therapeutically effective amount" or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of Type 2 diabetes.

The compounds of Formula (I) that are used in the methods of the present invention can be incorporated into a variety of formulations for therapeutic administration. More particularly, the compounds of Formula (I) can be formulated into pharmaceutical compositions by combination with appropriate, pharmaceutically acceptable carriers or diluents and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than ic manner, in a depot or sustained release formulation. In addition, the compounds can be administered in a liposome.

The compounds of Formula (I) can be formulated with common excipients, diluents or carriers and compressed into tablets or formulated as elixirs or solutions for convenient oral administration or administered by the intramuscular or intravenous routes. The compounds can be administered transdermally and can be formulated as sustained release dosage forms and the like. Compounds of Formula (I) can be administered alone, in combination with each other or they can be used in combination with other known compounds (see Combination Therapy below).

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution or physiological saline buffer. For transmucosal administration, penetrants appropriate to the barrier to be permeated are used in the formulation. Such penetrants are generally known in the art.

For oral administration, the compounds of Formula (I) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture and processing the mixture of granules, after adding suitable auxiliaries, if desired, to obtain tablets or dragee cores. Suitable excipients are, in particular, fillers such as sugars, including lactose, sucrose, mannitol or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose and/or polyvinylpyrrolidone (PVP). If desired, disintegrating agents can be added, such as the cross-linked polyvinyl pyrrolidone, agar or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol and/or titanium dioxide, lacquer solutions and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds can be dissolved or suspended in suitable liquids, such as fatty oils, liquid paraffin or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil or synthetic fatty acid esters, such as ethyl oleate or triglycerides or liposomes. Aqueous injection suspensions can contain substances which increase the viscosity of the suspension, such as sodium carboxymethyl cellulose, sorbitol or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins or as sparingly soluble derivatives, for example, as a sparingly soluble salt.

Alternatively, other delivery s for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics*, Ch. 1).

The amount of active compound that can be combined with a carrier material to produce a single dosage form will vary depending upon the disease treated, the mammalian species and the particular mode of administration. However, as a general guide, suitable unit doses for the compounds of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration and such therapy can extend for a number of weeks or months and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day or, multiple times per day or one time-release capsule or tablet taken once a day and containing a proportionally higher content of active ingredient. The time-release effect can be obtained by capsule materials that dissolve at different pH values, by capsules that release slowly by osmotic pressure or by any other known means of controlled release.

It can be necessary to use dosages outside these ranges in some cases as will be apparent to those skilled in the art. Further, it is noted that the clinician or treating physician will know how and when to interrupt, adjust or terminate therapy in conjunction with individual patient response.

Combination Therapy

As noted above, the compounds of the present invention will, in some instances, be used in combination with other therapeutic agents to bring about a desired effect. Selection of additional agents will, in large part, depend on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R. *J. Clin. Endocrinol. Metab.* (1999) 84: 1165-71; United Kingdom Prospective Diabetes Study Group: UKPDS 28, *Diabetes Care* (1998) 21: 87-92; Bardin, C. W.,(ed.), CURRENT THERAPY IN ENDOCRINOLOGY AND METABOLISM, 6th Edition (Mosby-Year Book, Inc., St. Louis, Mo. 1997); Chiasson, J. et al., *Ann. Intern. Med.* (1994) 121: 928-935; Coniff, R. et al., *Clin. Ther.* (1997) 19: 16-26; Coniff, R. et al., *Am. J. Med.* (1995) 98: 443-451; and Iwamoto, Y. et al., *Diabet. Med.* (1996) 13 365-370; Kwiterovich, P. *Am. J. Cardiol* (1998) 82(12A): 3U-17U). These studies indicate that diabetes and hyperlipidemia modulation can be further improved by the addition of a second agent to the therapeutic regimen. Combination therapy includes administration of a single pharmaceutical dosage formulation which contains a compound having the general structure of Formula (I) and one or more additional active agents, as well as administration of a compound of Formula (I) and each active agent in its own separate pharmaceutical dosage formulation. For example, a compound of Formula (I) and an HMG-CoA reductase inhibitor can be administered to the human subject together in a single oral dosage composition, such as a tablet or capsule or each agent can be administered in separate oral dosage formulations. Where separate dosage formulations are used, a compound of Formula (I) and one or more additional active agents can be administered at essentially the same time (i.e., concurrently) or at separately staggered times (i.e., sequentially). Combination therapy is understood to include all these regimens.

An example of combination therapy that modulates (prevents the onset of the symptoms or complications associated) atherosclerosis, wherein a compound of Formula (I) is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin and atorvastatin), an HMG-CoA synthase inhibitor, a squalene epoxidase inhibitor or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of Formula (I) can be administered in combination with more than one additional active agent, for example, a combination of a compound of Formula (I) with an HMG-CoA reductase inhibitor (e.g., lovastatin, simvastatin and pravastatin) and aspirin or a compound of Formula (I) with an HMG-CoA reductase inhibitor and a β blocker.

Another example of combination therapy can be seen in treating obesity or obesity-related disorders, wherein the compounds of Formula (I) can be effectively used in combination with, for example, phenylpropanolamine, phentermine, diethylpropion, mazindol; fenfluramine, dexfenfluramine, phentiramine, β-3 adrenoceptor agonist agents; sibutramine, gastrointestinal lipase inhibitors (such as orlistat) and leptins. Other agents used in treating obesity or obesity-related disorders wherein the compounds of Formula (I) can be effectively used in combination with, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications and disorders), wherein the compounds of Formula (I) can be effectively used in combination with, for example, sulfonylureas (such as chlorpropamide, tolbutamide, acetohexamide, tolazamide, glyburide, gliclazide, glynase, glimepiride and glipizide), biguanides (such as metformin), thiazolidinediones (such as ciglitazone, pioglitazone, troglitazone and rosiglitazone); dehydroepiandrosterone (also referred to as DHEA or its conjugated sulphate ester, DHEA-SO₄); antiglucocorticoids; TNFα inhibitors; α-glucosidase inhibitors (such as acarbose, miglitol and voglibose), pramlintide (a synthetic analog of the human hormone amylin), other insulin secretogogues (such as repaglinide, gliquidone and nateglinide), insulin, as well as the active agents discussed above for treating atherosclerosis.

A further example of combination therapy can be seen in modulating hyperlipidemia (treating hyperlipidemia and its related complications), wherein the compounds of Formula (I) can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E or vitamin C.

Additionally, an effective amount of a compound of Formula (I) and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate and gemfibrozil; vitamin B₆ and the pharmaceutically acceptable salts thereof, vitamin B₁₂; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, β-3 adrenergic receptor agonists; sulfonylureas, biguanides, α-glucosidase inhibitors, other insulin secretogogues and insulin can be used together for the preparation of a pharmaceutical composition useful for the above-described treatments.

Kits

In addition, the present invention provides for kits with unit doses of the compounds of Formula (I), either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia and hyperuricemia or for alleviating conditions dependent on PPAR. Preferred compounds and unit doses are those described herein above.

For the compositions, methods and kits provided above, one of skill in the art will understand that preferred compounds for use in each are those compounds that are preferred above and particularly those compounds provided in formula (I) in FIGS. 1A-1D. Still further preferred compounds for the compositions, methods and kits are those compounds provided in the Examples below.

EXAMPLES

Experimental Section

General Methods

Intermediates

Synthesis of Intermediate Compound 10

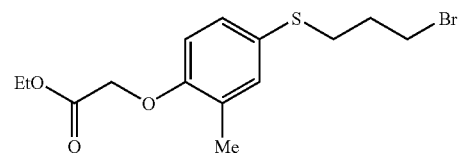

To a mixture of 1,3-dibromopropane (3 eq) and 4-mercapto-2-methyl-phenol (1 eq) in MeCN was added Cs₂CO₃ (1 eq), the mixture was stirred at room temperature for 4 hrs. Ethyl bromoacetate (1.2 eq) was added followed by addition of Cs₂CO₃ (1.2 eq), the mixture was stirred for another 4 hours. The mixture was filtrated through Celite and washed with ethyl acetate. The solvent was evaporated and the residue was purified by flash chromatography on silica gel to give the desired compound 10.

Synthesis of Intermediate Compound 20

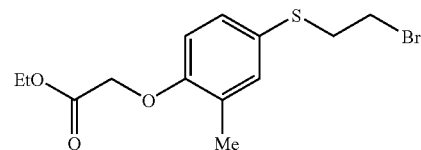

The same protocol as described for compound 10 was applied using 1,2-dibromoethane to give compound 20.

Synthesis of Intermediate Compound 30

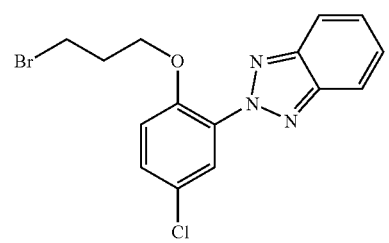

To a mixture of 1,3-dibromopropane (3 eq) and 4-chloro-2-benzotriazo-2-yl-phenol (1 eq) in MeCN was added Cs₂CO₃ (1 eq). The mixture was stirred at room temperature for 4 hrs. The mixture was filtrated through Celite and washed with ethyl acetate. The solvent was evaporated and the residue was purified by flash chromatography on silica gel to give desired compound 30.

Synthesis of Intermediate Compound 37

The same protocol as described for compound 10 was applied using 1-chloro-3-bromopropane to give compound 37.

Synthesis of Intermediate Compound 38

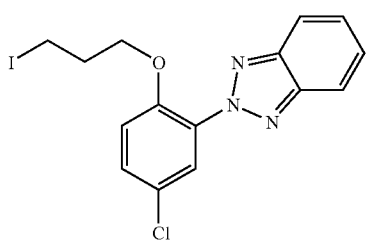

To a solution of Compound 37 in acetone was added NaI (3 eq.), the resulting mixture was refluxed over night. The reaction mixture was cooled to room temperature and diluted with water. The precipitate was filtered and washed with water. The solid was air dried to yield compound 38.

Synthesis of Intermediate Compound 40

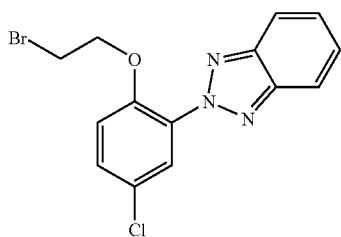

The same protocol as described for compound 30 was applied using 1,2-dibromoethane to give compound 40.

Synthesis of Intermediate Compound 50

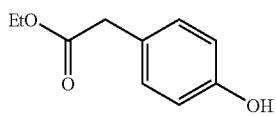

In a round-bottomed flask was placed 4-hydroxyphenyl acetic acid (10.0 g, 65.7 mmol), ethanol (120 ml) and conc. $H_2SO_4$ (1 ml). The mixture was heated at reflux for 1 hr and was then allowed to cool to room temperature. The mixture was carefully neutralized with aqueous $NaHCO_3$. Most of the ethanol was removed in vacuum. The aqueous phase was extracted with EtOAc, which was washed well with $H_2O$ and dried over $Na_2SO_4$. Evaporation of the solvent gave the desired compound as an oil (11.8 g, 100%). $^1H$ NMR (400 MHz, $CDCl_3$) δ 7.13 (d, 2H), 6.76 (d, 2H), 5.10 (s, 1H), 4.15 (q, 2H), 3.36 (s, 2H), 1.26 (t, 3H).

Synthesis of Compound 60

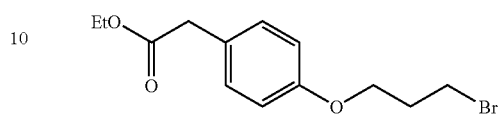

A mixture of (4-hydroxy-phenyl)-acetic acid ethyl ester (5.8 g, 32.2 mmol), 1,3-dibromopropane (16.3 ml, 5 eq.) and $Cs_2CO_3$ (12.6 g, 1.2 eq.) in $CH_3CN$ (100 ml) was stirred at room temperature overnight. The solid was filtered off and the filtrate was concentrated in vacuum. The crude product was purified on silica gel (Combiflash, 120 g cartridge, 5% to 25% EtOAc in hexanes in 20 min) to give 7.7 g (80%) of the desired compound as an oil. $^1H$ NMR (400 MHz, $CDCl_3$) δ 7.20 (d, 2H), 6.86 (d, 2H), 4.12 (q, 2H), 4.08 (t, 2H), 3.60 (t, 2H), 3.55 (s, 2H), 2.31 (m, 2H), 1.25 (t, 3H).

Synthesis of Compound 61

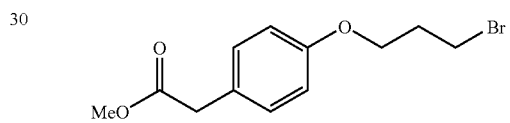

The same protocol as described for compound 60 was applied using (4-hydroxy-phenyl)-acetic acid methyl ester, 1,3-dibromopropane to yield compound 61.

Synthesis of Compound 70

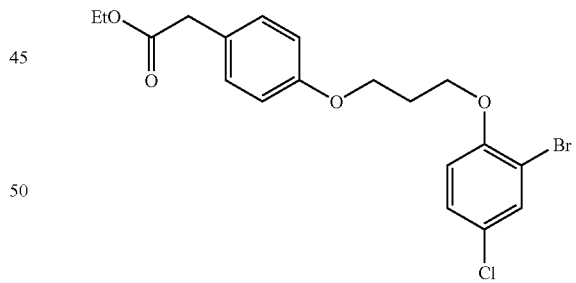

A mixture of [4-(3-bromo-propoxyl)-phenyl]-acetic acid ethyl ester (2.0 g, 6.64 mmol), 2-bromo-4-chloro-phenol (1.52 g, 1.1 eq.) and $Cs_2CO_3$ (2.6 g, 1.2 eq.) in $CH_3CN$ (30 ml) was heated to reflux for 1 hr. After cooling to room temperature, the solid was filtered off and the filtrate was concentrated in vacuum. The crude product was purified on silica gel (Combiflash, 120 g cartridge, 10% to 25% EtOAc in hexanes in 15 min) to give 2.64 g (96%) of the desired compound as a clear oil. $^1H$ NMR (400 MHz, $CDCl_3$) δ 7.52 (s, 1H), 7.21 (d, 1H), 7.18 (d, 2H), 6.88 (d, 2H), 6.83 (d, 1H), 4.19 (m, 4H), 4.13 (q, 2H), 3.56 (s, 2H), 2.29 (m, 2H), 1.24 (t, 3H).

Synthesis of Intermediate Compound 80

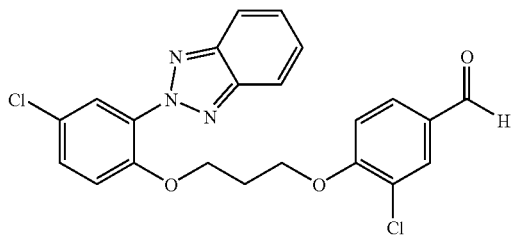

To a mixture of 3-chloro-4-hydroxy-benzaldehyde (1.57 g, 10 mmol) and compound 30 (3.67g, 10 mmol) in MeCN (40 mL) was added $Cs_2CO_3$ (3.91 g, 24 mmol). The mixture was stirred at room temperature for 4 hrs. The mixture was filtrated through Celite and washed with ethyl acetate. The solvent was evaporated and the residue was purified by flash chromatography on silica gel to give 3.5 g desired 80.

Synthesis of Intermediate Compound 81

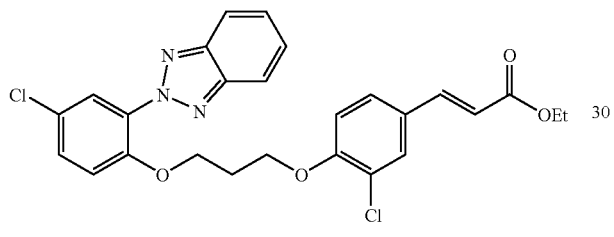

To a solution of compound 80 (0.88g, 2 mmol) in toluene (10 mL) was added (triphenylphosphanylidene)-acetic acid ethyl ester (0.84 g, 2.4 mmol). The mixture was refluxed for 3 hrs, cooled to room temperature and evaporated. The residue was purified by flash column on slica gel to give 0.6 g of compound 81.

Synthesis of Intermediate Compound 82

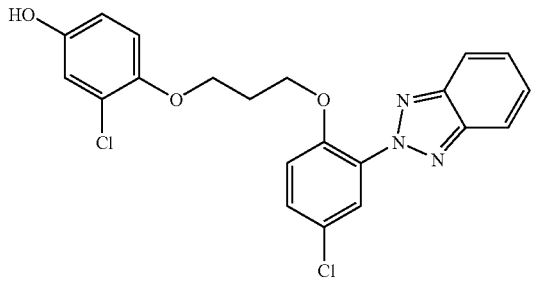

To compound 80 (2g, 4.5 mmol), in $CH_2Cl_2$ (30 mL) was added mCPBA (1.67 g, 70%, 6.75 mmol) at 0° C. The mixture was stirred over night at room temperature, quenched with aqueous $Na_2S_2O_3$, washed with $NaHCO_3$, brine and dried over $Na_2SO_4$. The volatile was evaporated. The residue was purified by flash chromatography on silica gel to give 0.65 g intermediate 82.

Example 1

{4-[3-(2-Benzotriazol-2-yl-4-chloro-phenoxy)-propylsulfanyl]-2-methyl-phenoxy}-acetic acid ethyl ester (Compound 90)

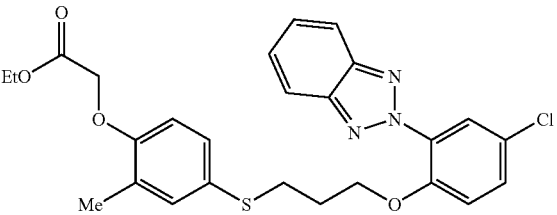

To a mixture of [4-(3-bromo-propylsulfanyl)-2-methyl-phenoxy]-acetic acid ethyl ester (139 mg, 0.4 mmol) and 2-benzotriazole-2-yl-4-chloro-phenol (108 mg, 0.44 mmol) in MeCN (3 mL) was added $Cs_2CO_3$ (156 mg, 0.48 mmol). The mixture was stirred at room temperature for 4 hrs. The mixture was filtrated through Celite and washed with ethyl acetate. The solvent was evaporated and the residue was purified by flash chromatography on silica gel to give 145 mg of the desired ester.

Example 2

{4-[3-(2-Benzotriazol-2-yl-4-chloro-phenoxy)-propylsulfanyl]-2-methyl-phenoxy}-acetic acid (Compound 100)

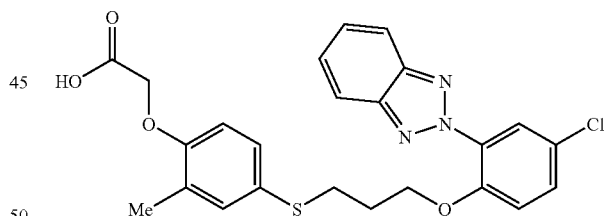

To a solution of the ester in THF (2 mL) was added aqueous LiOH (1.5 mL, 1.5 mmol). The mixture was stirred at room temperature for 1 hr, acidified with 1N HCl, extracted with EtOAc. The organic phase was washed with brine, dried and concentrated. The residue was recrystallized from hexanes and ethyl acetate to give 75 mg of compound 100 as a white solid. $^1$H NMR (400 MHz, $CDCl_3$) δ 9.4 (1H, br), 7.96~7.9 (2H, m), 7.71 (1H, d, J=2.4 Hz), 7.46~7.4 (2H, m), 7.39 (1H, d, J=2.4 Hz), 7.11 (1H, d, J=2 Hz), 7.01~6.99 (2H, m), 6.47 (1H, d, J=8.4 Hz), 4.61 (2H, s), 4.1 (2H, t, J=5.8 Hz), 2.88 (2H, t, J=7 Hz), 2.16 (3H, s), 1.96~1.89 (2H, m).

Example 3

{4-[3-(2-Benzothiazol-2-yl-4-chloro-phenoxy)-propylsulfanyl]-2-methyl-phenoxy}-acetic acid (Compound 200)

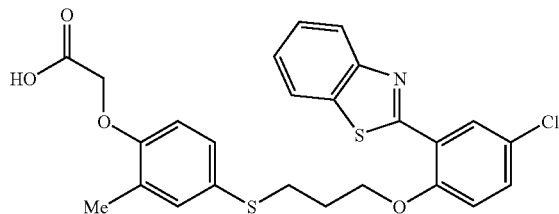

The same protocol as described for compound 100 was applied using compound 10 and 2-benzothiazol-2-yl-4-chloro-phenol to yield compound 200. $^1$H NMR (400 MHz, CDCl$_3$) δ 10.2 (1H, br), 8.45 (1H, d, J=2.4 Hz), 8.08 (1H, d, J=3.6 Hz), 7.89~7.86 (1H, m), 7.5~7.48 (1H, m), 7.39~7.37 (1H, m), 7.29 (1H, dd, J=8.8, 2.8 Hz), 7.21~7.2 (1H, m), 7.16 (1H, dd, J=8, 2.4 Hz) 6.83 (1H, d, J=9.2 Hz), 6.56 (1H, d, J=8.4 Hz), 4.62 (2H, s), 4.2 (2H, t, J=5.8 Hz), 3.15 (2H, t, J=6.8 Hz), 2.26~2.2 (2H, m), 2.17 (3H, s).

Example 4

{4-[3-(2-Benzooxazol-2-yl-4-bromo-phenoxy)-propylsulfanyl]-2-methyl-phenoxy}-acetic acid, (Compound 300)

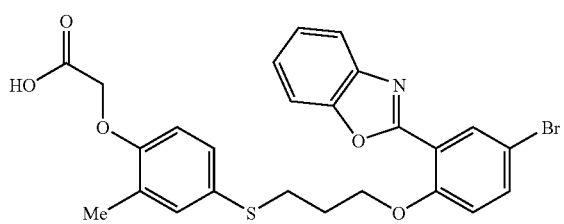

The same protocol as described for compound 100 was applied using compound 10 and 2-benzooxazol-2-yl-4-bromo-phenol to yield compound 300. $^1$H NMR (400 MHz, DMSO) δ 13(1H, br), 8.12 (1H, d, J=2.8 Hz), 7.77~7.73 (1H, m), 7.71 (1H, d, J=2.8 Hz), 7.65~7.62 (1H, m), 7.44~7.38 (2H, m), 7.21 (1H, d, J=8.8 Hz), 7.17~7.15 (1H, m), 7.12 (1H, dd, J=8, 2.6 Hz), 6.65 (1H, d, J=8.4 Hz), 4.62 (2H, s), 4.22 (2H, t, J=5.6 Hz), 3.17 (2H, t, J=7.2 Hz), 2.03~1.98 (2H, m), 2.03 (3H, s).

Example 5

{4-[2-(2-Benzotriazol-2-yl-4-chloro-phenoxy)-ethylsulfanyl]-2-methyl-phenoxy}-acetic acid (Compound 400)

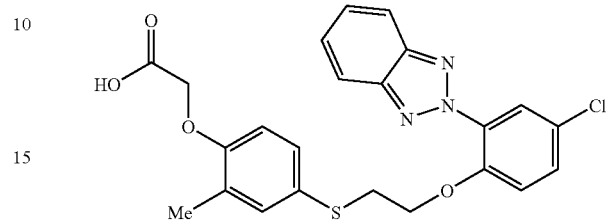

The same protocol as described for compound 100 was applied using of [4-(2-bromo-ethylsulfanyl)-2-methyl-phenoxy]-acetic acid ethyl ester and 2-benzotriazole-2-yl-4-chloro-phenol to yield compound 400. $^1$H NMR (400 MHz, CDCl$_3$) δ 9(1H, br), 7.96~7.92 (2H, m), 7.69 (1H, d, J=2.8 Hz), 7.46~7.4 (2H, m), 7.38 (1H, dd, J=9.2, 2.8 Hz), 7.16~7.15 (1H, m), 7.1 (1H, dd, J=8.4, 2.4 Hz), 6.97 (1H, d, J=8.8 Hz), 6.53 (1H, d, J=8.4 Hz), 4.61 (2H, s), 4.12 (2H, t, J=7 Hz), 3.04 (2H, t, J=7 Hz), 2.19 (3H, s).

Example 6

{4-[3-(2-Benzotriazol-2-yl-4-chloro-phenoxy)-propoxy]-phenyl}-acetic acid methyl ester (Compound 490)

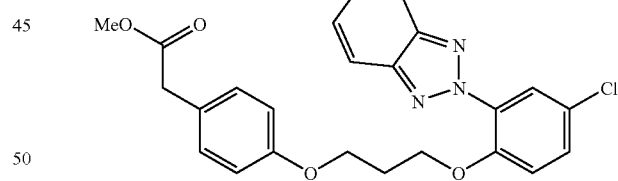

To a mixture of 4-hydroxy-phenyl-acetic acid methyl ester (100 mg, 0.6 mmol) and compound 30 (220 mg, 0.6 mmol) in MeCN (3 mL) was added Cs$_2$CO$_3$ (234 mg, 0.72 mmol). The mixture was stirred at room temperature for 4 hrs. The mixture was filtrated through Celite and washed with ethyl acetate. The solvent was evaporated and the residue was purified by flash chromatography on silica gel to give 210 mg desired ester 490.

Example 7

{4-[3-(2-Benzotriazol-2-yl-4-chloro-phenoxy)-propoxy]-phenyl}-acetic acid (Compound 500)

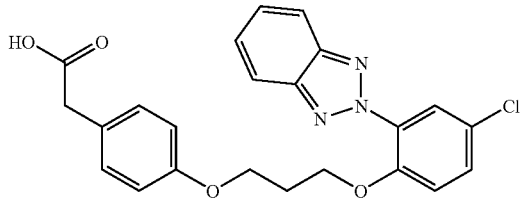

To a solution of the ester 490 in THF (2 mL) was added aqueous LiOH (1.8 mL, 1.8 mmol). The mixture was stirred at room temperature for 1 hr, acidified with 1N HCl and extracted with EtOAc. The organic phase was washed with brine, dried and concentrated. The residue was recrystallized from hexanes and ethyl acetate to give 110 mg of compound 500 as a white solid. $^1$H NMR (400 MHz, CDCl3) δ 7.92~7.88 (2H, m), 7.7 (1H, d, J=2.8 Hz), 7.43~7.38 (3H, m), 7.12~7.06 (3H, m), 6.75~6.0 (2H, m), 4.21 (2H, t, J=6.2 Hz), 3.96 (2H, t, J=6.2 Hz), 3.55 (2H, s), 2.15~2.09 (2H, m).

Example 8

{4-[3-(2-Benzotriazol-2-yl-4-chloro-phenoxy)-propoxy]-3-propyl-phenyl}-acetic acid (Compound 600)

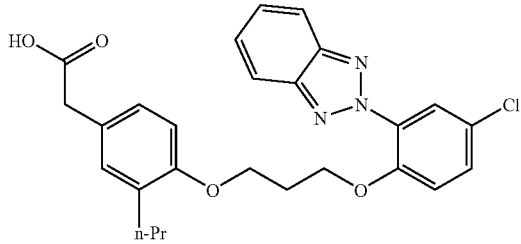

The same protocol as described for compound 500 was applied using 4-hydroxy-3-propyl-phenyl-acetic acid methyl and compound 30 to yield compound 600. $^1$H NMR (400 MHz, CDCl$_3$) δ 7.92~7.88 (2H, m), 7.71 (1H, d, J=2.8 Hz), 7.44~7.38 (3H, m), 7.09 (1H, d, J=8.8 Hz), 7(1H, d, J=2.4 Hz), 6.96 (1H, dd, J=8, 2.4 Hz), 6.62 (1H, d, J=8.8 Hz), 4.24 (2H, t, J=6.2 Hz), 3.95 (2H, t, J=6 Hz), 3.53 (2H, s), 2.49 (1H, t, J=7.6 Hz), 2.16~2.12 (2H, m), 1.56~1.46 (2H, m), 0.87 (3H, t, J=7.8 Hz).

Example 9

{4-[3-(2-Benzotriazol-2-yl-4-chloro-phenoxy)-propoxy]-3-chloro-phenyl}-acetic acid (Compound 700)

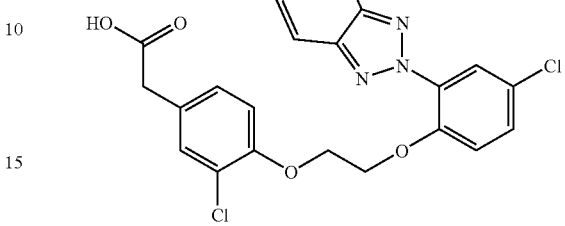

The same protocol as described for compound 500 was applied using 3-chloro-4-hydroxy-phenyl-acetic acid methyl and compound 30 to yield compound 700. $^1$H NMR (400 MHz, CDCl$_3$) δ 7.94~7.88 (2H, m), 7.7 (1H, d, J=2.8 Hz), 7.46~7.41 (3H, m), 7.25 (1H, d, J=2 Hz), 7.13 (1H, d, J=8.8 Hz), 6.98 (1H, dd, J=8.8, 2.4 Hz), 6.7 (1H, d, J=8.8 Hz), 4.28 (2H, t, J=6.4 Hz), 4.03 (2H, t, J=6 Hz), 3.53 (2H, s), 2.21~2.15 (2H, m).

Example 10

{4-[2-(2-Benzotriazol-2-yl-4-chloro-phenoxy)-ethoxy]-phenyl}-acetic acid (Compound 800)

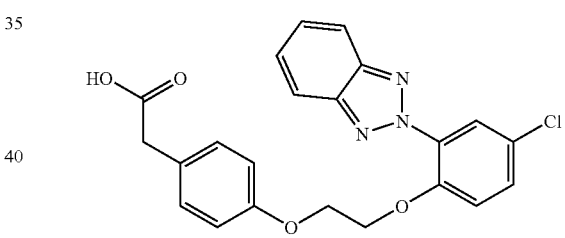

The same protocol as described for compound 500 was applied using 4-hydroxy-phenyl-acetic acid methyl and compound 40 to yield compound 800. $^1$H NMR (400 MHz, CDCl$_3$) δ 7.94~7.88 (2H, m), 7.73 (1H, d, J=2.4 Hz), 7.48~7.4 (3H, m), 7.19 (1H, d, J=9.2 Hz), 7.06~7.02 (2H, m), 6.76~6.72 (2H, m), 4.39 (2H, t, J=5Hz), 4.21 (2H, t, J=5 Hz), 3.53 (2H, s).

Example 11

{4-[2-(2-Benzotriazol-2-yl-4-chloro-phenoxy)-ethoxy]-3-propyl-phenyl}-acetic acid (Compound 900)

The same protocol as described for compound 500 was applied using 4-hydroxy-3-propyl-phenyl-acetic acid methyl and compound 30 to yield compound 900. $^1$H NMR (400 MHz, CDCl$_3$) δ $^1$H NMR (400 MHz, CDCl$_3$) δ 7.94~7.88 (2H, m), 7.72 (1H, d, J=2.8 Hz), 7.46~7.38 (3H, m), 7.17 (1H, d, J=9.2 Hz), 6.94 (1H, d, J=2.4 Hz), 6.86 (1H, dd, J=8.4, 2 Hz), 6.64 (1H, d, J=8 Hz), 4.38 (2H, t, J=5 Hz), 4.18 (2H, t, J=5 Hz), 3.49 (2H, 3), 2.37 (2H, t, J=7.6 Hz), 1.44~1.38 (2H, m), 0.77 (3H, t, J=7.4 Hz).

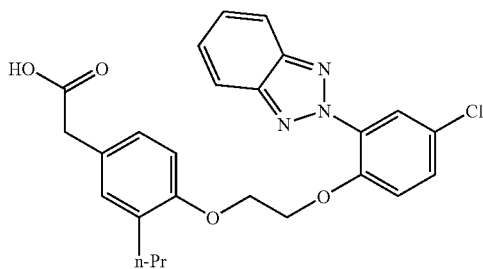

Example 12

{4-[3-(2-Benzotriazol-2-yl-4-chloro-phenoxy)-propoxy]-phenoxy}-acetic acid (Compound 1000)

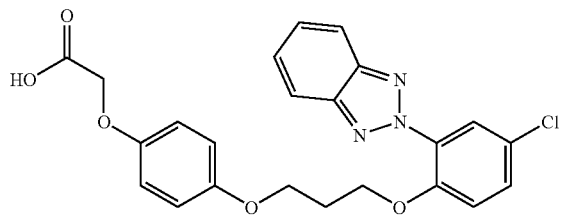

The same protocol as described for compound 10 was applied using (4-hydroxy-phenoxy)-acetic acid methyl and compound 30 to yield compound 1000. ¹H NMR (400 MHz, CDCl₃) δ 7.94~7.88 (2H, m), 7.71 (1H, d, J=2.8 Hz), 7.6~7.42 (3H, m), 7.11 (1H, d, J=9.2 Hz), 6.81~6.76 (2H, m), 6.74~6.69 (2H, m), 4.38 (2H, t, J=5 Hz), 4.6 (2H, s), 4.24 (2H, t, J=6 Hz), 3.94 (2H, t, J=6.2 Hz), 2.16~2.09 (2H, m).

Example 13

{4-[2-(2-Benzotriazol-2-yl-4-thiophen-2-yl-phenoxy)-propoxy]-phenyl}-acetic acid methyl ester (Compound 1090)

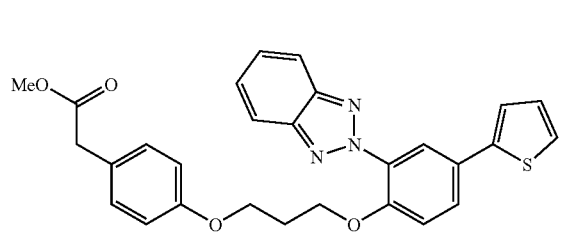

The mixture of compound 490 (451 mg, 1 mmol), palladium acetate (6.7 mg, 0.03 mmol), biphenyl-2-yl-di-tert-butyl-phosphine (18 mg, 0.06 mmol), potassium fluoride (174 mg, 3 mmol) and 2-thiopheneboronic acid (192 mg, 1.5 mmol) in anhydrous toluene (3 mL) was heated at 110° C. under N₂ for 48 hours. The mixture was filtered through a pad of Celite and washed with EtOAc. The organic phase was washed with aqueous NaHCO₃, brine, dried over NaSO₄ and evaporated. The residue was purified by chromatography on silica gel to yield 0.18 g desired ester.

Example 14

{4-[3-(2-Benzotriazol-2-yl-4-thiophen-2-yl-phenoxy)-propoxy]-phenyl}-acetic acid (Compound 1100)

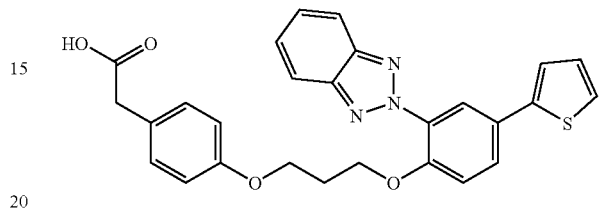

To a solution of the ester 1090 in THF (5 mL) was added aqueous LiOH (1 mL, 1 mmol). The mixture was stirred at room temperature for 1 hr, acidified with 1N HCl and extracted with EtOAc. The organic phase was washed with brine, dried and concentrated. The residue was purified by chromatography on silica gel to yield 0.13 g compound 1100. ¹H NMR (400 MHz, DMSO) δ 7.98~7.94 (3H, m), 7.86 (1H, dd, J=8.8, 2.4 Hz), 7.54~7.46 (4H, m), 7.44 (1H, d, J=8.8 Hz), 7.13~7.08 (3H, m), 6.76~6.7 (2H, m), 4.26 (2H, t, J=6 Hz), 3.93 (2H, t, J=6.4 Hz), 3.46 (2H, s), 2.94~1.96 (2H, m).

Example 15

(4-{3-[4-Chloro-2-(4,5,6,7-tetrahydro-benzotriazol-2-yl)-phenoxy]-propoxy}-phenyl)-acetic acid methyl ester (Compound 1190)

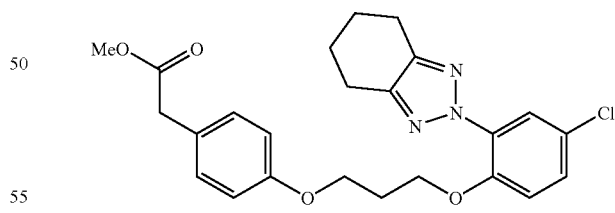

The mixture of 0.9 g compound 490, 100 mg 10% Pd/C in EtOAc (20 ml) was hydrogenated under H₂ for 3 hours. The mixture was filtered through a pad of Celite, washed with EtOAc, the solvent was evaporated and residue was purified by chromatography to afford 0.6 g desired ester.

Example 16

(4-{3-[4-Chloro-2-(4,5,6,7-tetrahydro-benzotriazol-2-yl)-phenoxy]-propoxy}-phenyl)-acetic acid (Compound 1200)

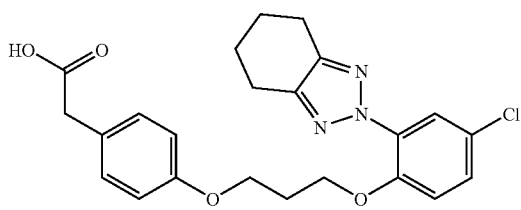

To a solution of the ester in THF (5 mL) was added aqueous LiOH (1 mL, 1 mmol). The mixture was stirred at room temperature for 1 hr, acidified with 1N HCl and extracted with EtOAc. The organic phase was washed with brine, dried and concentrated. The residue was purified by chromatography on silica gel to yield 0.13 g compound 1200. $^1$H NMR (400 MHz, CDCl$_3$) δ 7.53 (1H, d, J=2.8 Hz), 7.29 (1H, dd, J=8.8, 2.8 Hz), 7.18~7.14 (2H, m), 7(1H, d, J=8.8 Hz), 6.84~6.8 (2H, m), 4.19 (2H, t, J=6Hz), 4.06 (2H, t, J=6.2 Hz), 3.57 (2H, s), 2.77~2.73 (4H, m), 2.22~1.96 (2H, m), 1.87~1.83 (4H, m).

Example 17

{4-[3-(4-Chloro-2-phenylethynyl-phenoxy)-propoxy]-phenyl}-acetic acid ethyl ester (Compound 1290)

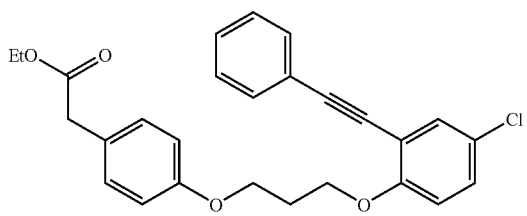

A mixture of compound 70 (350 mg, 0.85 mmol), phenyl acetylene (121 µl, 1.3 eq.), PdCl$_2$(PPh$_3$)$_2$ (60 mg) and CuI (33 mg) in a mixed solvent of Et$_3$N and THF (15 ml) in a capped pressured flask under nitrogen was heated at 80° C. overnight. After cooling, the solvent was removed in vacuo. The residue was purified on silica gel to give the desired compound.

Example 18

{4-[3-(4-Chloro-2-phenylethynyl-phenoxy)-propoxy]-phenyl}-acetic acid (Compound 1300)

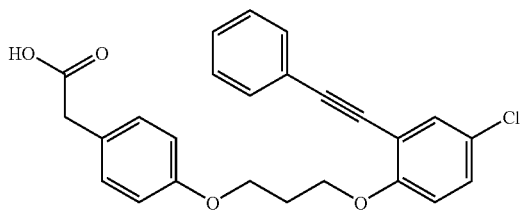

To a solution of the ester 1290 in THF (2 ml) was added aqueous LiOH (1.5 ml). The mixture was stirred at r.t. for 1 hr. Then it was acidified with 1N HCl and the mixture was extracted with EtOAc. The organic layer was washed with brine, dried over Na$_2$SO$_4$ and concentrated. The residue was purified on silica gel to give the title compound as a pale yellow solid. $^1$H NMR (400 MHz, CDCl$_3$) δ 7.52-7.45 (m, 3H), 7.33-7.31 (m, 3H), 7.24-7.13 (m, 3H), 6.89-6.82 (m, 3H), 4.21 (m, 4H), 3.55 (s, 2H), 2.29 (m, 2H).

Example 19

(4-{3-[4-Chloro-2-(3-methoxy-phenylethynyl)-phenoxy]-propoxy}-phenyl)-acetic acid (Compound 1400)

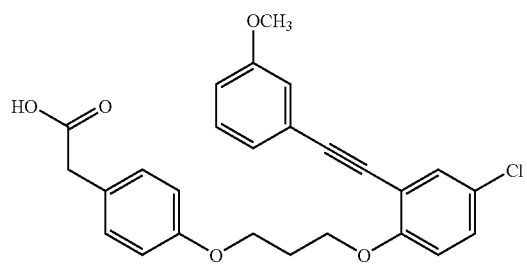

Using the same protocol as described for compound 1300, compound 1400 was synthesized via coupling with 1-ethynyl-3-methoxybenzene. $^1$H NMR (400 MHz, CDCl3) δ7.45 (s, 1H), 7.24-6.83 (m, 10H), 4.22 (m, 4H), 3.77 (s, 3H), 3.56 (s, 2H), 2.31 (m, 2H).

Example 20

{4-[3-(4-Chloro-2-pyridin-2-ylethynyl-phenoxy)-propoxy]-phenyl}-acetic acid (Compound 1500)

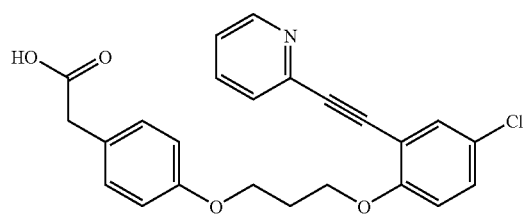

Using the same protocol as described for compound 1300, compound 1500 was synthesized via coupling with 2-ethynyl-pyridine. $^1$H NMR (400 MHz, CDCl$_3$) δ 8.58 (br, 1H), 7.64 (m, 1H), 7.51-7.45 (m, 2H), 7.28-7.24 (m, 2H), 7.16-7.13 (m, 2H), 6.88-6.85 (m, 3H), 4.23 (m, 4H), 3.53 (s, 2H), 2.32 (m, 2H).

Example 21

(4-{3-[4-Chloro-2-(4-methyl-benzotriazol-2-yl)-phenoxy]-propoxy}-phenyl)-acetic acid ethyl ester (Compound 1590)

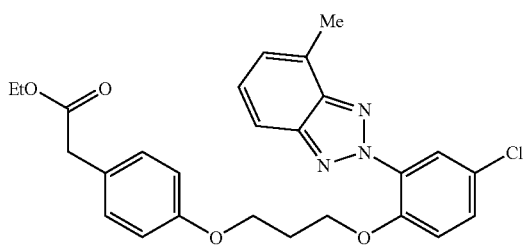

A mixture of 4-chloro-2-(4-methyl-benzotriazol-2-yl)-phenol (93 mg, 0.36 mmol), [4-(3-bromo-propoxyl)-phenyl]-acetic acid ethyl ester (130 mg, 1.2 eq.) and $Cs_2CO_3$ (140 mg, 1.2 eq.) in $CH_3CN$ (10 ml) was heated to reflux for 1 hr. After cooling to r.t., the solid was filtered off and the filtrate was concentrated in vacuo. The crude product was purified on silica gel to give the desired compound.

Example 22

(4-{3-[4-Chloro-2-(4-methyl-benzotriazol-2-yl)-phenoxy]-propoxy}-phenyl)-acetic acid (Compound 1600)

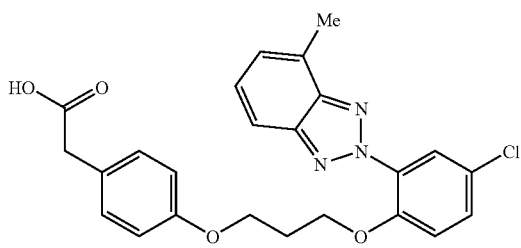

To a solution of the ester 1590 in THF (2 ml) was added aqueous LiOH (1.5 ml). The mixture was stirred at r.t. for 1 hr. Then it was acidified with 1N HCl and extracted with EtOAc. The organic layer was washed with brine, dried over $Na_2SO_4$ and concentrated. The residue was purified on silica gel to give the title compound as a white solid. $^1$H NMR (400 MHz, DMSO) δ 12.20 (br, 1H), 7.80 (d, 1H), 7.73 (d, 1H), 7.65 (dd, 1H), 7.43-7.23 (m, 2H), 7.24 (d, 1H), 7.06 (d, 2H), 6.70 (d, 2H), 4.22 (t, 2H), 3.92 (t, 2H), 3.44 (s, 2H), 2.55 (s, 3H), 1.98 (m, 2H).

Example 23

{5-[3-(2-Benzotriazol-2-yl-4-chloro-phenoxy)-propoxy]-indazol-1-yl}-acetic acid (Compound 1700)

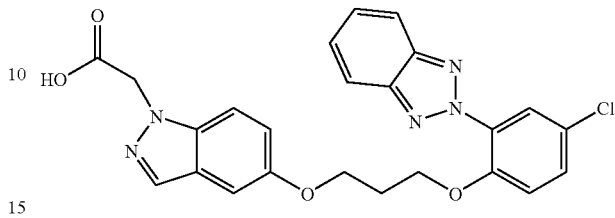

Compound 1700 was synthesized using the same protocol as described for compound 1600. $^1$H NMR (400 MHz, DMSO) δ7.93-7.90 (m, 3H), 7.82 (d, 1H), 7.66 (dd, 1H), 7.48-7.43 (m, 4H), 6.99 (d, 1H), 6.93 (dd, 1H), 5.19 (s, 2H), 4.26 (t, 2H), 3.94 (t, 2H), 2.00 (m, 2H).

Example 24

{5-[3-(2-Benzotriazol-2-yl-4-chloro-phenoxy)-propoxy]-indol-1-yl}-acetic acid (Compound 1800)

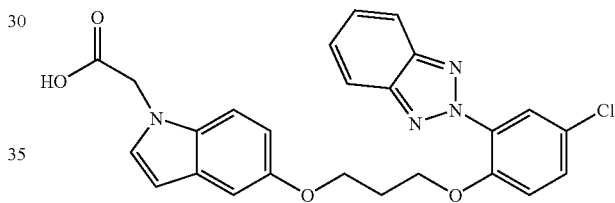

Compound 1800 was synthesized using the same protocol as described for compound 1700 starting with an indole compound. $^1$H NMR (400 MHz, DMSO) δ 7.93-7.90 (m, 3H), 7.82 (d, 1H), 7.66 (dd, 1H), 7.28-7.2 (m, 4H), 7.17 (d, 1H), 6.78 (dd, 1H), 5.19 (s, 2H), 4.3 (t, 2H), 3.9 (t, 2H), 2.00 (m, 2H).

Example 25

{5-[2-(2-Benzotriazol-2-yl-4-chloro-phenoxy)-ethoxy]-indol-1-yl}-acetic acid (Compound 1900)

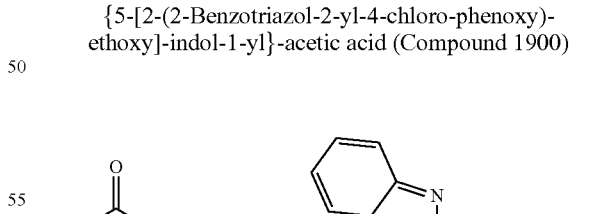

Compound 1900 was synthesized using the same protocol as described for compound 1700 starting with an indole compound. $^1$H NMR (400 MHz, DMSO) δ 7.97-7.90 (m, 3H), 7.81 (d, 1H), 7.7 (dd, 1H), 7.28-7.2 (m, 5H), 6.78 (dd, 1H), 5.19 (s, 2H), 4.3 (t, 2H), 4.1 (t, 2H).

Example 26

2-{4-[3-(2-Benzotriazol-2-yl-4-chloro-phenoxy)-propoxy]-2-methyl-phenoxy}-2-methyl-propionic acid (Compound 5800)

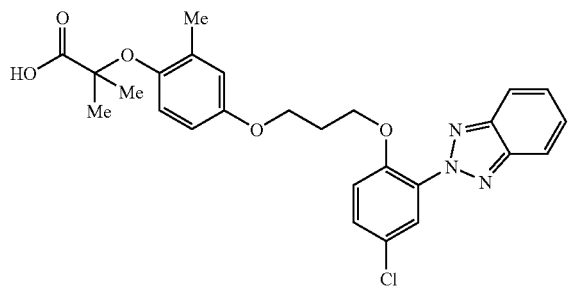

The same protocol as described for compound 500 was applied using 2-(4-Hydroxy-2-methyl-phenoxy)-2-methyl-propionic acid ethyl ester and compound 30 to yield compound 5800. $^1$H NMR (400 MHz, DMSO) δ 7.96~7.9 (2H, m), 7.81 (1H, d, J=2.8 Hz), 7.65 (1H, dd, J=9.2, 2.8 Hz), 7.52~7.46 (2H, m), 7.42 (1H, d, J=9.2 Hz), 6.62 (1H, d, J=9.2 Hz), 6.61 (1H, s), 6.44 (1H, d, J=8.8, 3.2 Hz), 4.21 (2H, t, J=6 Hz), 3.83 (2H, t, J=6.4 Hz), 2.07 (3H, s), 1.98~1.9 (2H, m), 1.41 (6H, s).

Example 27

2-{4-[3-(2-Benzotriazol-2-yl-4-chloro-phenoxy)-propoxy]-2-chloro-phenoxy}-2-methyl-propionic acid (Compound 7400)

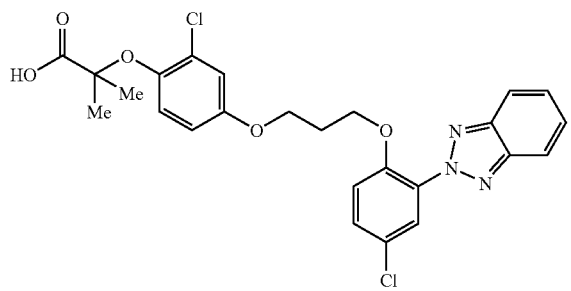

The same protocol as described for compound 500 was applied using 2-(2-chloro-4-Hydroxy-phenoxy)-2-methyl-propionic acid ethyl ester and compound 30 to yield compound 7400. $^1$H NMR (400 MHz, DMSO) δ 13.09 (1H, br), 7.94~7.92 (2H, m), 7.81 (1H, d, J=2.4 Hz), 7.65 (1H, dd, J=8.8, 2.8 Hz), 7.49~7.47 (2H, m), 7.42 (1H, d, J=9.6 Hz), 6.90 (1H, d, J=9.2 Hz), 6.91 (1H, s), 6.66 (1H, dd, J=8.8, 3.2 Hz), 4.21 (2H, t, J=6 Hz), 3.89 (2H, t, J=6.4 Hz), 1.97~1.94 (2H, m), 1.44 (6H, s).

Example 28

{4-[3-(2-Benzotriazol-2-yl-4-fluoro-phenoxy)-propoxy]-phenyl}-acetic acid (Compound 12210)

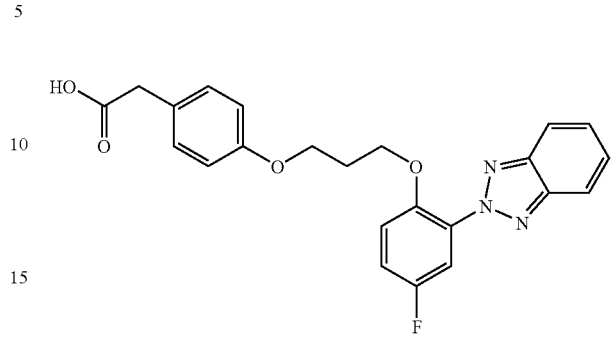

The same protocol as described for compound 100 was applied using compound 60A and 2-benzotriazol-2-yl-4-fluoro-phenol to yield compound 12210. $^1$H NMR (400 MHz, DMSO) δ 7.96~7.9 (2H, m), 7.67 (1H, dd, J=8.4, 2.8 Hz), 7.52~7.46 (3H, m), 7.43 (1H, dd, J=9.6, 5.2 Hz), 7.08 (2H, d, J=8.4 Hz), 6.7 (2H, d, J=8.8 Hz), 4.2 (2H, t, J=6 Hz), 3.89 (2H, t, J=6.4 Hz), 3.45 (2H, s), 2~1.92 (2H, m).

Example 29

2-{4-[3-(2-Benzotriazol-2-yl-4-chloro-phenoxy)-propoxy]-phenyl}-propionic acid (Compound 13000)

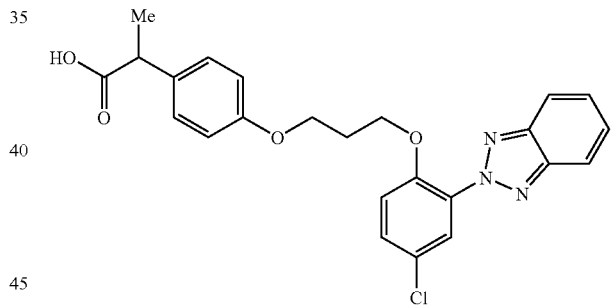

To a solution of Compound 490 (0.45 g, 1 mmol) in THF (15 mL) was added KHMDS (3 mL, 1.5 mmol) at −78° C. under N$_2$. The mixture was stirred at −78° for 0.5 hr and MeI (0.56g, 4 mmol) was added. The mixture was stirred at −78° for 2 hrs and was quenched with saturated aqueous NH$_4$Cl, diluted with EtOAc organic layer was dried over NaSO$_4$, evaporated and the residue was purified by flash chromatography on silica gel to afford 0.36g desired product.

To a solution of compound obtained above (0.36g, 0.77 mmol) in THF (4 mL) was added aqueous LiOH (2 mL, 2 mmol). The mixture was stirred at room temperature for 2 hrs, acidified with 1N HCl, extracted with EtOAc. The organic phase was washed with brine, dried and concentrated. The residue was recrystallized from hexanes and ethyl acetate to give 0.3 g of compound as a white solid. $^1$H NMR (400 MHz, DMSO) δ 7.96~7.9 (2H, m), 7.81 (1H, d, J=2.8 Hz), 7.65 (1H, dd, J=9.2, 2.8 Hz), 7.42 (1H, d, J=9.2 Hz), 751~7.46 (2H, m), 7.12~7.08 (2H, m), 6.74~6.68 (2H, m), 4.22 (2H, t, J=6Hz), 3.9 (2H, t, J=6.4 Hz), 3.56 (1H, q, J=7.2 Hz), 2~1.92 (2H, m), 1.3 (3H, d, J=6.8 Hz).

Example 30

2-{4-[3-(2-Benzotriazol-2-yl-4-chloro-phenoxy)-propoxy]-phenyl}-2-methyl-propionic acid (Compound 13100)

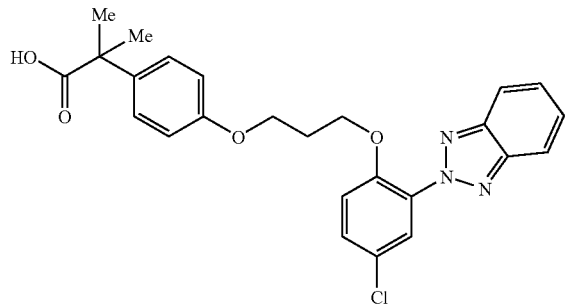

The same protocol as described for compound 500 was applied using 2-(4-Hydroxy-phenyl)-2-methyl-propionic acid methyl ester and compound 30 to yield compound 13100. $^1$H NMR (400 MHz, CDCl$_3$) δ 7.92~7.87 (2H, m), 7.71 (1H, d, J=2.4 Hz), 7.46~7.4 (3H, m), 7.24~7.2 (2H, m), 7.09 (1H, d, J=9.2 Hz), 6.76~6.7 (2H, m), 4.23 (2H, t, J=6 Hz), 3.97 (2H, t, J=6.4 Hz), 2.18~2.1 (2H, m), 1.56 (6H, s).

Example 31

{4-[3-(3-Benzooxazol-2-yl-phenoxy)-propylsulfanyl]-2-methyl-phenoxy}-acetic acid (Compound 21200)

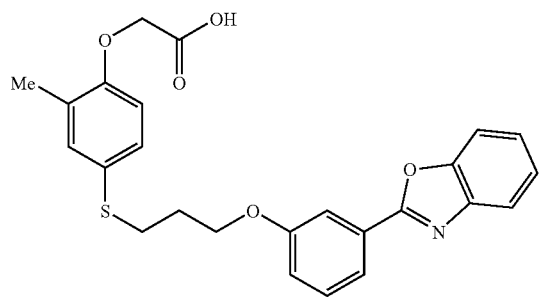

The same protocol as described for compound 100 was applied using compound 10 and 3-benzooxazol-2-yl-phenol to yield compound 21200. $^1$H NMR (400 MHz, DMSO) δ 7.82~7.74 (3H, m), 7.66 (1H, s), 7.50 (1H, t, J=8 Hz), 7.46~7.37 (2H, m), 7.23~7.14 (3H, m), 6.75 (1H, d, J=8.4 Hz), 4.64 (2H, s), 4.16 (2H, t, J=6 Hz), 3.02 (2H, t, J=7 Hz), 2.13 (3H, s), 2~1.9 (2H, m).

Example 32

(4-{3-[3-(4,5-Dimethyl-oxazol-2-yl)-phenoxy]-propylsulfanyl}-2-methyl-phenoxy)-acetic acid (Compound 21300)

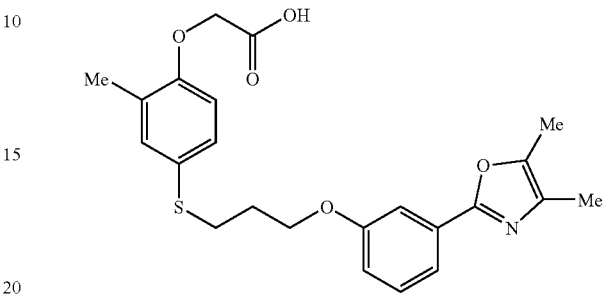

The same protocol as described for compound 100 was applied using compound 10 and 3-(4,5-Dimethyl-oxazol-2-yl)-phenol to yield compound 21300. $^1$H NMR (400 MHz, DMSO) δ 7.46~7.34 (3H, m), 7.2 (1H, s), 7.16 (1H, dd, J=8.4, 2 Hz), 6.99 (1H, dd, J=8.4, 2 Hz), 6.75 (1H, d, J=8.8 Hz), 4.64 (2H, s), 4.09 (2H, t, J=6 Hz), 2.99 (2H, t, J=7.2 Hz), 2.29 (3H, s), 2.13 (3H, s), 2.07 (3H, s), 1.98~1.9 (2H, m).

Example 33

{4-[3-(2-Benzotriazol-2-yl-4-chloro-phenoxy)-propoxy]-3-methoxy-phenyl}-acetic acid (Compound 21400)

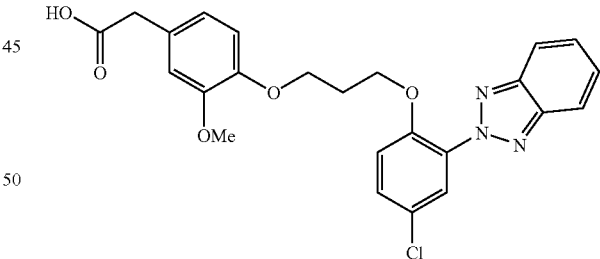

The same protocol as described for compound 500 was applied using 4-hydroxy-3-methoxy-phenyl-acetic acid methyl ester and compound 30 to yield compound 21400. $^1$H NMR (400 MHz, CDCl$_3$) δ 7.92~7.88 (2H, m), 7.7 (1H, d, J=2.8 Hz), 7.45~7.41 (3H, m), 7.10 (1H, d, J=2 Hz), 6.76 (1H, m), 6.66 (1H, d, J=1.2 Hz), 4.25 (2H, t, J=6.4 Hz), 4.03 (2H, t, J=6 Hz), 3.79 (3H, s), 3.56 (2H, s), 2.19 (2H, m).

Example 34

{4-[3-(2-Benzotriazol-2-yl-4-chloro-phenoxy)-propoxy]-3-Bromo-phenyl}-acetic acid (Compound 21500)

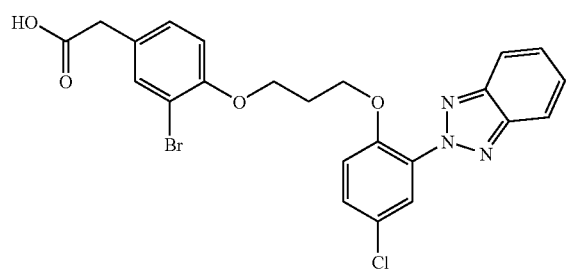

The same protocol as described for compound 500 was applied using 3-Bromo-4-hydroxy-phenyl-acetic acid methyl ester and compound 30 to yield compound 21500. $^1$H NMR (400 MHz, DMSO) δ 7.96~7.9 (2H, m), 7.81 (1H, d, J=2.8 Hz), 7.66 (1H, dd, J=9.2, 2.8 Hz), 7.52~7.46 (2H, m), 7.43 (1H, d, J=8.8, 2 Hz), 7.11 (1H, dd, J 8.4, 1.6 Hz), 6.82 (1H, d, J=8.8 Hz), 4.27 (2H, t, J=6 Hz), 3.99 (2H, t, J=6 Hz), 3.47 (2H, s), 2.14~2.08 (2H, m).

Example 35

{3-[3-(2-Benzotriazol-2-yl-4-chloro-phenoxy)-propoxy]-phenyl}-acetic acid (Compound 21600)

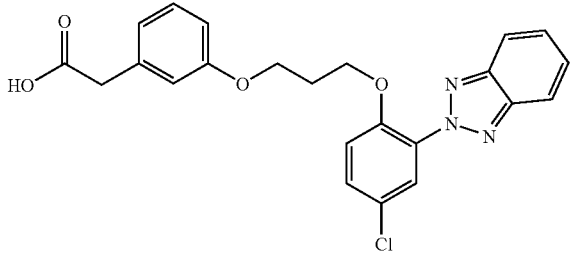

The same protocol as described for compound 500 was applied using 3-hydroxy-phenyl-acetic acid methyl ester and compound 30 to yield compound 21600. $^1$H NMR (400 MHz, CDCl$_3$) δ 7.94~7.88 (2H, m), 7.71 (1H, d, J=2.4 Hz), 7.46~7.4 (3H, m), 7.17 (1H, t, J=8 Hz), 7.1 (1H, d, J=9.2 Hz), 6.83 (1H, d, J=7.2 Hz), 6.75 (1H, t, J=2 Hz), 6.72~6.68 (1H, m), 4.23 (2H, t, J=6 Hz), 3.92 (2H, t, J=6 Hz), 3.56 (3H, s), 2.18~2.1 (2H, m).

Example 36

{4-[3-(2-Benzothiazol-2-yl-4-chloro-phenoxy)-propoxy]-phenyl}-acetic acid (Compound 21700)

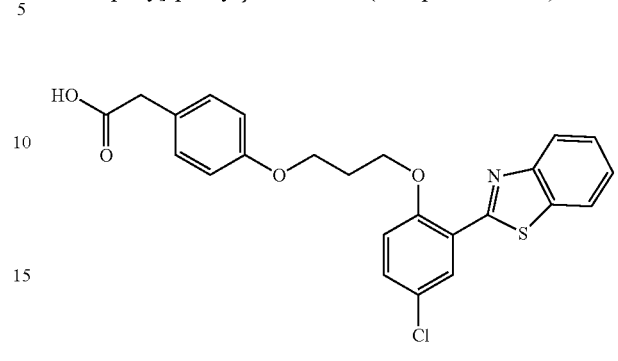

The same protocol as described for compound 100 was applied using compound 60 and 2-benzothiazol-2-yl-4-chloro-phenol to yield compound 21700. $^1$H NMR (400 MHz, DMSO) δ 8.38 (1H, d, J=2.8 Hz), 8.06 (2H, d, J=8.8 Hz), 7.57 (1H, dd, J=8.8, 2.8 Hz), 7.54 (1H, t, J=8.4 hz), 7.44 (1H, t, J=8.4 Hz), 7.13 (2H, d, J=8.8 Hz), 6.99 (2H, d, J=8.4 Hz), 4.44 (2H, t, J=6 Hz), 4.25 (2H, t, J=6Hz), 3.45 (2H, s), 2.42~2.34 (2H, m).

Example 37

{4-[3-(2-Benzooxazol-2-yl-4-bromo-phenoxy)-propoxy]-phenyl}-acetic acid (Compound 21800)

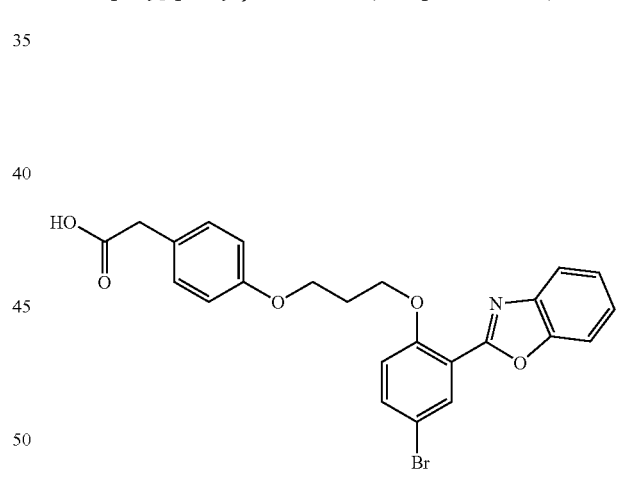

The same protocol as described for compound 100 was applied using compound 60 and 2-Benzooxazol-2-yl-4-bromo-phenol to yield compound 21800. $^1$H NMR (400 MHz, CDCl$_3$) δ 8.25 (1H, d, J=2.4 Hz), 7.79~7.74 (1H, m), 7.56 (1H, dd, J=8.8, 2.8 Hz), 7.52~7.47 (1H, m), 7.37~7.32 (2H, m), 7.17~7.12 (2h, m), 6.97 (1H, d, J=8.8 Hz), 6.88~6.84 (2H, m), 4.31 (2H, t, J=6 Hz), 4.27 (2H, t, J=6.4 Hz), 3.56 (2H, s), 2.18~2.1 (2H, m).

Example 38

{4-[3-(2-Benzooxazol-2-yl-4-thiophen-2-yl-phenoxy)-propoxy]-phenyl}-acetic acid (1100A 21900)

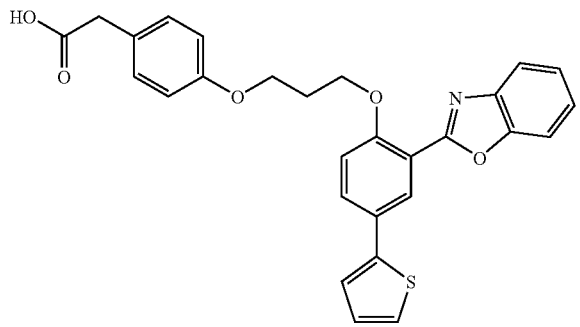

The same protocol as described for compound 1100 was applied using ester of compound 21800 to yield compound 21900. $^1$H NMR (400 MHz, CDCl$_3$) δ 8.35 (1H, d, J=2.4 Hz), 7.8~7.77 (1H, m), 7.7 (1H, dd, J=8.8, 2.4 Hz), 7.54~7.5 (1H, m), 7.36~7.32 (3H, m), 7.28~7.26 (1H, m), 7.15 (2H, d, J=9.2 Hz), 7.11 (1H, d, J=9.2 Hz), 7.08 (1H, dd, J=5.2, 3.2 Hz), 4.36 (2H, t, J=6.4 Hz), 4.29 (2H, t, J=6.4 Hz), 3.57 (2H, s), 2.4~2.34 (2H, m).

Example 39

(4-{3-[2-(4,5,6,7-Tetrahydro-benzotriazol-2-yl)-phenoxy]-propoxy}-phenyl)-acetic acid (Compound 22000)

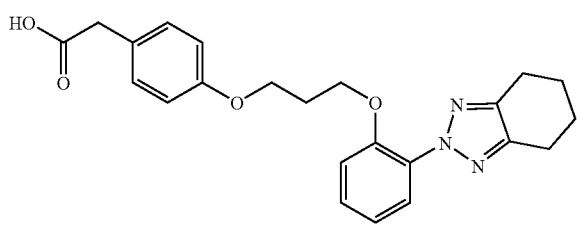

The mixture of compound 500, 10% Pd/C in EtOAc was hydrogenated under H$_2$ (50 Psi) for 24 hours. The mixture was filtered through a pad of Celite, washed with EtOAc, the solvent was evaporated and residue was purified by chromatography to afford desired product. $^1$H NMR (400 MHz, DMSO) δ 12.21 (1H, br), 7.45~7.38 (2H, m), 7.26 (1H, d, J=8 Hz), 7.13 (2H, d, J=8.4 Hz), 707~7.02 (1H, m), 6.81 (2H, d, J=8.4 Hz), 4.17 (2H, t, J=6 Hz), 4.03 (2H, t, J=6 Hz), 3.46 (2H, s), 2.68~2.6 (4H, m), 2.08~2 (2H, m), 1.8~1.72 (4H, m).

Example 40

(4-{3-[4-Fluoro-2-(4,5,6,7-tetrahydro-benzotriazol-2-yl)-phenoxy]-propoxy}-phenyl)-acetic acid (Compound 22100)

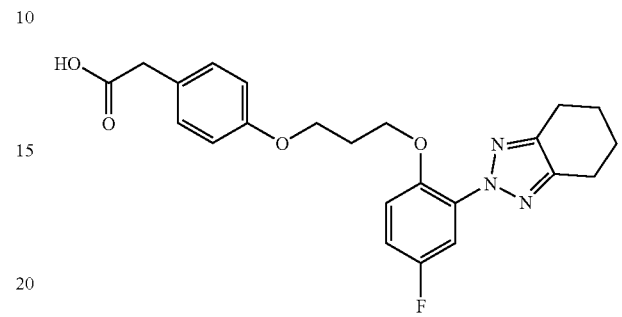

The same protocol as described for compound 1200 was applied using ester of compound 12210 to yield compound 22100. $^1$H NMR (400 MHz, CDCl$_3$) δ 7.3 (1H, dd, J=8.4, 2.4 Hz), 7.16 (2H, d, J=8.4 Hz), 7.06~7(2H, m), 6.82 (2H, d, J=8.8 Hz), 4.17 (2H, t, J=6 Hz), 4.06 (2H, t, J=6 Hz), 3.57 (2H, s), 2.78~2.7 (4H, m), 2.22~2.14 (2H, m), 1.19~1.8 (4H, m).

Example 41

(4-{3-[4-Chloro-2-(4,5-dimethyl-[1,2,3]triazol-2-yl)-phenoxy]-propoxy}-phenyl)-acetic acid (Compound 22200)

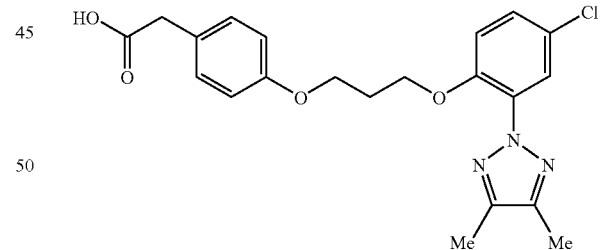

The same protocol as described for compound 100 was applied using compound 60 and 4-Chloro-2-(4,5-dimethyl-[1,2,3]triazol-2-yl)-phenol to yield compound 22200. $^1$H NMR (400 MHz, CDCl$_3$) δ 7.51 (1H, d, J=2.4 Hz), 7.29 (1H, dd, J=9, 2.6 Hz), 7.18~7.14 (2H, m), 6.99 (1H, d, J=8.8 Hz), 6.84~6.8 (2H, m), 4.18 (2H, t, J=6Hz), 4.05 (2H, t, J=6.4 Hz), 3.57 (2H, s), 2.27 (6H, s), 2.22~2.16 (2H, m).

Example 42

{4-[3-(2-Benzotriazol-2-yl-4-chloro-phenoxy)-propoxy]-phenyl}-methoxy-acetic acid (Compound 22300)

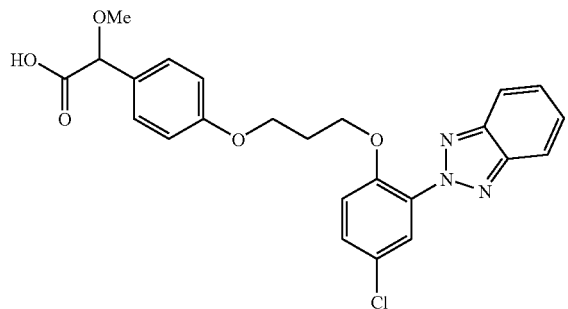

The same protocol as described for compound 500 was applied using (4-Hydroxy-phenyl)-methoxy-acetic acid Methyl ester and compound 30 to yield compound 22300. $^1$H NMR (400 MHz, DMSO) δ 12.73 (1H, br), 7.94~7.89 (2H, m), 7.81 (1H, d, J=2.8 Hz), 7.66 (1H, dd, J=9.2, 2.8 Hz), 7.5~7.44 (2H, m), 7.43 (1H, d, J=9.6 Hz), 7.24~7.19 (2H, m), 6.78~6.74 (2H, m), 4.65 (1H, s), 4.23 (2H, t, J=6 Hz), 3.92 (2H, t, J=6 Hz), 3.25 (3H, s), 2.02~1.94 (2H, m).

Example 43

4-[3-(2-Benzotriazol-2-yl-4-chloro-phenoxy)-propoxy]-3-chloro-benzoic acid 82 and intermediate (Compound 22400)

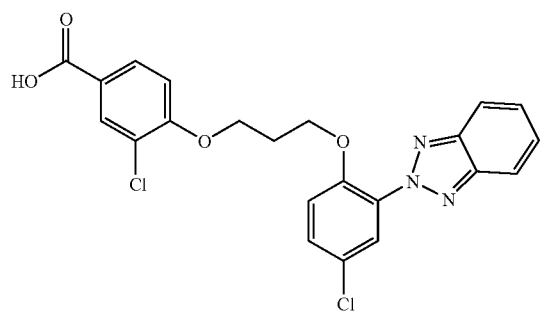

To compound 80 (2g, 4.5 mmol), in CH$_2$Cl$_2$ (30 mL) was added mCPBA (1.67 g, 70%, 6.75 mmol) at 0° C. The mixture was stirred over night at room temperature, quenched with aqueous Na$_2$S$_2$O$_3$, washed with NaHCO$_3$, brine and dried over Na$_2$SO$_4$. The volatile was evaporated. The residue was purified by flash chromatography on silica gel to give 0.65 g intermediate 82 and 0.34 g Compound 22400. Compound 22400: $^1$H NMR (400 MHz, DMSO) δ 7.96~7.9 (2H, m), 7.84 (1H, d, J=2 Hz), 7.81 (1H, d, J=2.8 Hz), 7.9 (1H, dd, J=8.8, 2 Hz), 7.5~7.44 (2H, m), 7.44 (1H, d, J=8.8 Hz), 7.02 (1H, d, J=8.8 Hz), 4.27 (2H, t, J=6 Hz), 4.11 (2H, t, J=6 Hz), 2.15~2.11 (2H, m).

Example 44

Synthesis of (Compound 22500 and 22600)

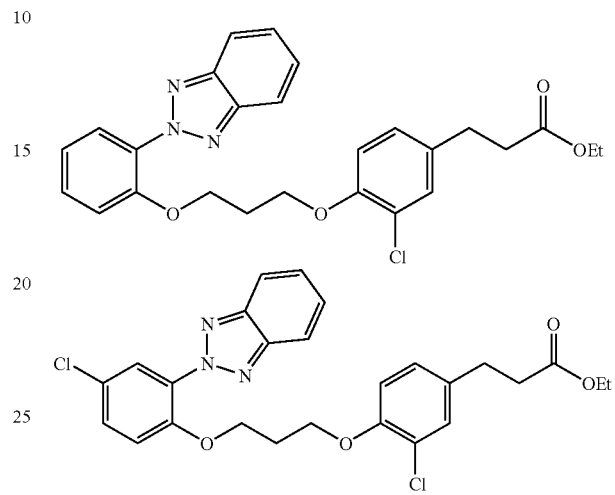

The mixture of compound 81 (0.6g), 10% Pd/C (100 mg) in EtOAc (20 mL) was hydrogenated under H$_2$ for 3 hours. The mixture was filtered through a pad of Celite, washed with EtOAc, the solvent was evaporated and residue was purified by chromatography to afford compound 22500 (0.14 g) and compound 22600 (0.15 g).

Example 45

{4-[3-(2-Benzotriazol-2-yl-4-chloro-phenoxy)-propoxy]-3-chloro-phenoxy}-acetic acid (Compound 22700)

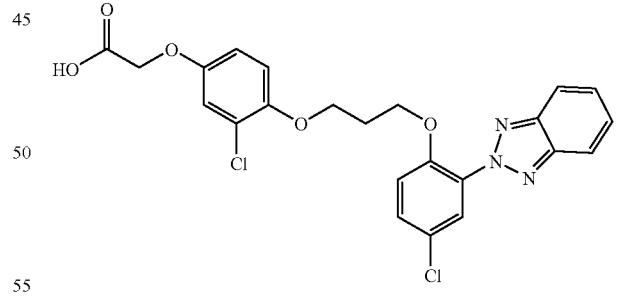

To a mixture of ethyl bromoacetate (0.18 g, 1.1 mmol) and compound 82 (0.43 g, 1 mmol) in MeCN (5 mL) was added Cs$_2$CO$_3$ (0.39 g, 1.2 mmol). The mixture was stirred at room temperature for 3 hrs. The mixture was filtrated through Celite and washed with ethyl acetate. The solvent was evaporated and the residue was purified by flash chromatography on silica gel to give 0.41 g ester.

To a solution of the ester in THF (4 mL) was added aqueous LiOH (3 mL, 3 mmol). The mixture was stirred at room temperature for 2 hrs, acidified with 1N HCl, extracted with EtOAc. The organic phase was washed with brine, dried and concentrated. The residue was recrystallized from hexanes and ethyl acetate to give 0.25 g of compound 22700 as a white solid. $^1$H NMR (400 MHz, CDCl$_3$) δ 7.94~7.88 (2H, m), 7.71 (1H, d, J=2.4 Hz), 7.46~7.4 (3H, m), 7.13 (1H, d, J=9.2 Hz), 6.94 (1H, d, J=2.8 Hz), 6.7~6.63 (2H, m), 4.59 (2H, s), 4.29 (2H, t, J=6 Hz), 3.99 (2H, t, J=6 Hz), 2.2~2.14 (2H, m).

Example 46

3-(3-Chloro-4-{3-[2-(4,5,6,7-tetrahydro-benzotriazol-2-yl)-phenoxy]-propoxy}-phenyl)-propionic acid (Compound 22800)

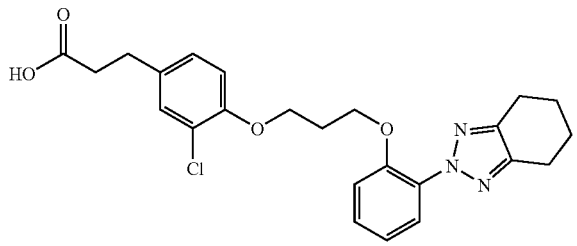

To a solution of Compound 22500 (0.14 g, 0.29 mmol) in THF (2 mL) was added aqueous LiOH (1 mL, 1 mmol). The mixture was stirred at room temperature for 2 hrs, acidified with 1N HCl, extracted with EtOAc. The organic phase was washed with brine, dried and concentrated. The residue was recrystallized from hexanes and ethyl acetate to give 90 mg of compound 22800 as a white solid. $^1$H NMR (400 MHz, CDCl$_3$) δ 7.48 (1H, dd, J=7.6, 1.6 Hz), 7.34 (1H, ddd, J=8.4, 7.6, 1.6 Hz), 7.18 (1H, d, J=2.4 Hz), 7.09 (1H, dd, J=8.4, 1 Hz), 7.02 (1H, td, J=7.6, 1.2 Hz), 6.99 (1H, dd, J=8.4, 2 Hz), 6.81 (1H, d, J=8 Hz), 4.24 (2H, t, J=6Hz), 4.1 (2H, t, J=6 Hz), 2.84 (2H, t, J=7.6 Hz), 2.8~2.73 (4H, m), 2.59 (2H, t, J=7.6 Hz), 2.26~2.2 (2H, m), 1.89~1.82 (4H, m).

Example 47

3-(3-Chloro-4-{3-[4-chloro-2-(4,5,6,7-tetrahydro-benzotriazol-2-yl)-phenoxy]-propoxy}-phenyl)-propionic acid (Compound 22900)

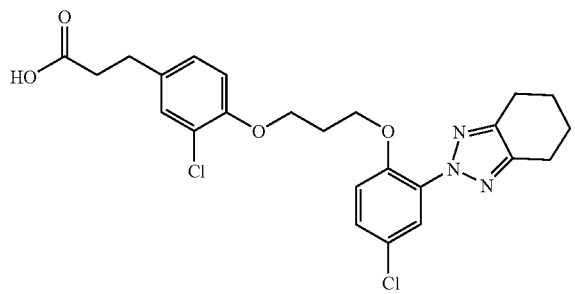

To a solution of Compound 22600 (0.15 g, 0.29 mmol) in THF (2 mL) was added aqueous LiOH (1 mL, 1 mmol). The mixture was stirred at room temperature for 2 hrs, acidified with 1N HCl, extracted with EtOAc. The organic phase was washed with brine, dried and concentrated. The residue was recrystallized from hexanes and ethyl acetate to give 80 mg of compound 22900 as a white solid. $^1$H NMR (400 MHz, DMSO) δ 7.53 (1H, d, J=2.4 Hz), 7.28 (1H, dd, J=8.8, 2.8 Hz), 7.18 (1H, d, J=2 Hz), 7.03 (1H, d, J=9.2 Hz),7 (1H, dd, J=8, 2.4 Hz), 6.81 (1H, d, J=8 Hz), 4.23 (2H, t, J=6Hz), 4.11 (2H, t, J=6 Hz), 2.84 (2H, t, J=7.6 Hz), 2.8~2.72 (4H, m), 2.6 (2H, t, J=7.6 Hz), 2.26~2.2 (2H, m), 1.89~1.82 (4H, m).

Example 48

Measurement of PPARγ, δ, and α Transactivation Activity

Chimeric receptors were constructed in which the yeast transcription factor GAL4 DNA binding domain was fused to the ligand binding domain of either mouse PPARγ, mouse PPAR δ or mouse PPAR α in order to assess the ability of the compounds of the present invention to activate gene expression in a PPAR-dependent manner. The chimeric receptor expression plasmids (GAL4-mPPARγ, GAL4-mPPAR δ and GAL4-PPAR α) and the reporter plasmid containing 5×GAL4 binding site (pFR-Luc, obtained from Stratagene) were transfected into HEK293T cells using the Lipofectamine 2000 reagent (Invitrogen), according to the manufacturers instructions. Six hours after transfection, the culture medium was renewed and the cells were incubated for 20 hours in presence of either 1) DMSO (vehicle), 2) a compound of the invention or 3) a reference compound for comparison. Rosiglitazone (obtained from WDF Pharma) was used as a reference compound for the PPARγ assay; GW501516 (prepared as described in Sznaidman et al. *Bioorg. Med. Chem. Lett.* (2003) 13:1517-1521) was used as a reference compound for the PPAR δ assay and GW7647 (obtained from Sigma) was used as a reference compound for the PPAR α assay. Luciferase activity was measured as a reporter of gene expression. Luciferase activity on the cell lysates using the Steady-Glo reagent was measured according to the manufacturers instructions.

TABLE 1

Results of the PPARs transactivation assay for selected compounds from FIG. 1.

| Compounds | Gene Activation Assay: EC$_{50}$ (≦10 μM) | | |
|---|---|---|---|
| | PPAR alpha | PPAR delta | PPAR gamma |
| 2100 | − | + | − |
| 2200 | − | − | + |
| 1800 | − | + | + |
| 400 | − | + | + |
| 1900 | − | + | + |
| 300 | + | + | + |
| 600 | + | + | + |
| 500 | + | + | + |
| 1700 | ND | + | + |
| 2300 | ND | + | + |
| 2400 | − | + | + |
| 2500 | − | + | + |
| 700 | + | + | + |
| 2600 | ND | + | + |
| 2700 | ND | + | + |
| 2800 | − | + | + |
| 2900 | + | + | + |
| 3000 | − | − | + |
| 900 | ND | + | + |
| 800 | − | + | + |
| 1300 | − | + | + |
| 1400 | − | + | + |
| 1500 | − | + | + |
| 3100 | + | + | + |
| 1600 | + | + | + |
| 1200 | + | + | + |

ND: no activity detected @ 30 μM

As is apparent from the test results above, the compounds of the invention are excellent modulators of PPAR.

While embodiments of the invention have been illustrated and described, it is not intended that these embodiments illustrate and describe all possible forms of the invention. Rather, the words used in the specification are words of description rather than limitation and is understood that various changes may be made without departing from the spirit and scope of the invention.

What is claimed is:

1. A compound having the formula:

$$Z—K—Ar^1—L—Ar^2—R^1 \qquad (I)$$

wherein

Ar$^1$ is selected from the group consisting of benzene, imidazole, indole and indazole, each of which is optionally substituted with a R$^2$ substituent, a R$^3$ substituent or a combination thereof;

Ar$^2$ is benzene, which is optionally substituted with from one to two R$^4$ substituents;

K is absent or is a linking group selected from the group consisting of —CH$_2$—, —CH$_2$CH$_2$, —CH$_2$O—, —CH(CH$_3$)O—, —C(CH$_3$)$_2$O—, —CH(CH$_3$)—, —CH(OCH$_3$)— and —C(CH$_3$)$_2$— wherein K can be attached to any available ring member of Ar$^1$;

L is a linking group joining Ar$^1$ and Ar$^2$ and is selected from the group consisting of —O(CH$_2$)$_3$O—, —O(CH$_2$)$_2$O—, —S(CH$_2$)$_3$O—, and —S(CH$_2$)$_2$O— wherein L can be attached to any available ring member of Ar$^1$ and to any available ring member of Ar$^2$;

Z is CO$_2$R$^8$;

R$^1$ is a member independently selected from the group consisting of:

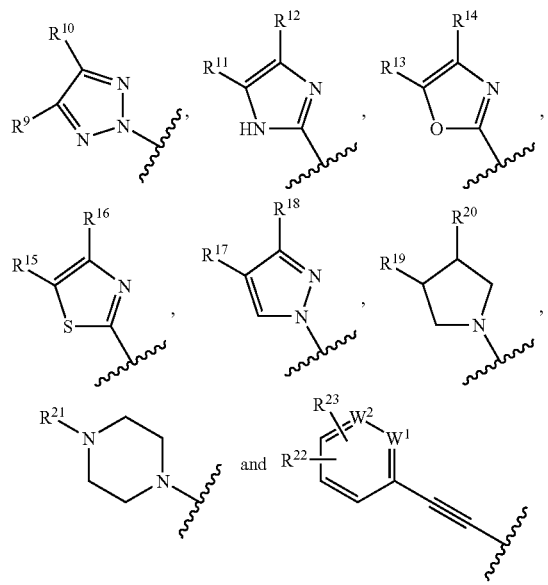

each R$^2$ or R$^3$ is independently selected from the group consisting of halogen, (C$_1$-C$_8$)alkyl, halo(C$_1$-C$_8$)alkyl, —OR$^7$, (C$_2$-C$_8$)alkenyl, (C$_2$-C$_8$)alkynyl, (C$_3$-C$_7$)cycloalkyl, (C$_3$-C$_7$)cycloalkyl(C$_1$-C$_4$)alkyl, aryl, aryl(C$_1$-C$_4$)alkyl, aryl(C$_2$-C$_8$)alkenyl, aryl(C$_2$-C$_8$)alkynyl, heterocyclyl, heterocyclyl(C$_1$-C$_4$)alkyl, —COR$^7$, —CO$_2$R$^7$, —NR$^7$R$^{24}$, —NO$_2$, —CN, —S(O)$_{r1}$R$^7$, —X$^1$OR$^7$, —X$^1$COR$^7$, —X$^1$CO$_2$R$^7$, —X$^1$NR$^7$R$^{24}$, —X$^1$NO$_2$, —X$^1$CN and —X$^1$S(O)$_{r1}$R$^7$;

each R$^4$ is independently selected from the group consisting of halogen, (C$_1$-C$_8$)alkyl, halo(C$_1$-C$_8$)alkyl, —OR$^7$, (C$_2$-C$_8$)alkenyl, (C$_2$-C$_8$)alkynyl, (C$_3$-C$_7$)cycloalkyl, (C$_3$-C$_7$)cycloalkyl(C$_1$-C$_4$)alkyl, aryl(C$_1$-C$_4$)alkyl, aryl (C$_2$-C$_8$)alkenyl, aryl(C$_2$-C$_8$)alkynyl, heterocyclyl, heterocyclyl(C$_1$-C$_4$)alkyl, —COR$^7$, —CO$_2$R$^7$, —NR$^7$R$^{24}$, —NO$_2$, —CN, —S(O)$_{r1}$R$^7$, —X$^2$OR$^7$, —X$^2$COR$^7$, —X$^2$CO$_2$R$^7$, —X$^2$NR$^7$R$^{24}$, —X$^2$NO$_2$, —X$^2$CN, —X$^2$S(O)$_{r1}$R$^7$,

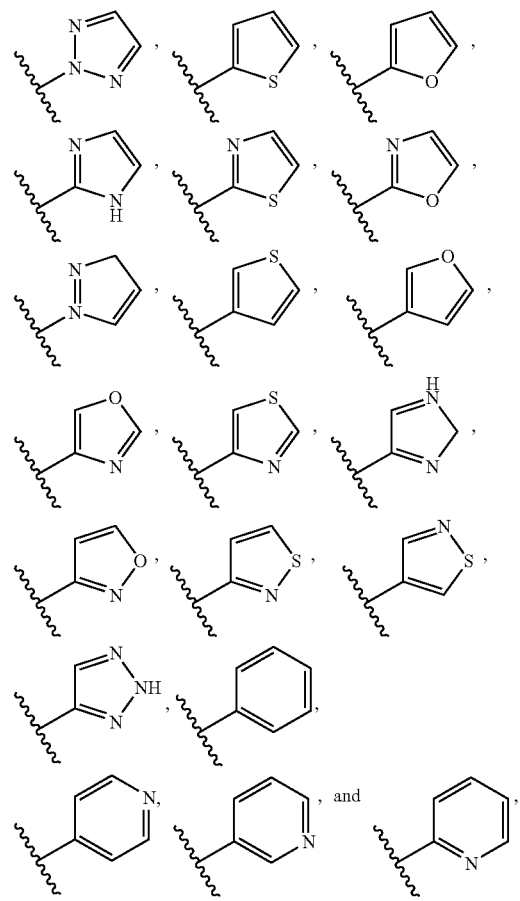

each ring of which is optionally substituted with from one to two substituents independently selected from the group consisting of halo and (C$_1$-C$_8$)alkyl;

each R$^7$ and R$^{24}$ is a member independently selected from the group consisting of H, (C$_1$-C$_8$)alkyl, halo(C$_1$-C$_8$) alkyl, —X$^3$OR$^{25}$, —CO, aryl, aryl(C$_1$-C$_4$)alkyl and heteroaryl or optionally, if both are present on the same substituent, may be joined together to form a three- to eight-membered ring;

each R$^8$ is a member independently selected from the group consisting of H, (C$_1$-C$_8$)alkyl, halo(C$_1$-C$_8$)alkyl, —X$^4$OR$^7$, —X$^4$NR$^7$R$^{24}$, (C$_2$-C$_8$)alkenyl, (C$_3$-C$_7$)cycloalkyl, heterocyclyl, heteroaryl, aryl, aryl(C$_1$-C$_4$)alkyl and aryl(C$_2$-C$_8$)alkenyl each R$^9$ or R$^{10}$ is independently selected from the group consisting of H, (C$_1$-C$_8$)alkyl, halo and (C$_1$-C$_8$)haloalkyl or is joined together with the triazole ring to form a triazolopyridine, benzotriazole or tetrahydrobenzotriazole ring optionally substituted with from one to two substituents independently selected from the group consisting of —OR⁷, —CO₂R⁷, —NR⁷R²⁴, —CN, S(O)$_{r1}$R⁷, halo, (C₁-C₈)alkyl and (C₁-C₈)haloalkyl;

each R¹¹ or R¹² is independently selected from the group consisting of H, (C₁-C₈)alkyl, halo and (C₁-C₈)haloalkyl or is joined together with the imidazole ring to form a benzimidazolyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹³ or R¹⁴ is independently selected from the group consisting of H, (C₁-C₈)alkyl, halo and (C₁-C₈)haloalkyl or is joined together with the oxazole ring to form a benzoxazolyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁵ or R¹⁶ is independently selected from the group consisting of H, (C₁-C₈)alkyl, halo and (C₁-C₈)haloalkyl or is joined together with the thiazole ring to form a benzothiazoyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁷ or R¹⁸ is independently selected from the group consisting of H, (C₁-C₈)alkyl, halo and (C₁-C₈)haloalkyl or is joined together with the pyrazole ring to form a indazoyl ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

each R¹⁹ or R²⁰ is independently selected from the group consisting of H, (C₁-C₈)alkyl, halo and (C₁-C₈)haloalkyl or is joined together with the pyrrolidine ring to form a dihydroisoindole ring, optionally substituted with from one to two substituents independently selected from the group consisting of —OR⁷, —CO₂R⁷, —NR⁷R²⁴, —CN, —S(O)$_{r1}$R⁷, halo, (C₁-C₈)alkyl and (C₁-C₈)haloalkyl;

R²¹ is CH₃, phenyl or pyridyl, wherein the phenyl and pyridyl substituents are, optionally substituted with from one to two substituents independently selected from the group consisting of —OR⁷, halo, (C₁-C₈)alkyl and (C₁-C₈)haloalkyl;

each of R²² or R²³ is independently selected from the group consisting of H, (C₁-C₈)alkyl, —OR⁷, halo and (C₁-C₉)haloalkyl;

R²⁵ is a member selected from the group consisting of H, (C₁-C₈)alkyl, halo(C₁-C₈)alkyl, aryl, aryl(C₁-C₄)alkyl and heteroaryl;

each W¹ or W² is independently N or CR²²;

each X¹, X², X³ and X⁴ is a member independently selected from the group consisting of (C₁-C₄)alkylene, (C₂-C₄)alkenylene and (C₂-C₄)alkynylene;

the subscript r1 is an integer of from 0 to 2; and pharmaceutically acceptable salts thereof.

2. A compound of claim 1, wherein R⁸ is H.

3. A compound of claim 1, wherein Ar¹ is selected from the group consisting of:

(i) an indole ring, optionally substituted with a R² substituent, a R³ substituent or a combination thereof; and (ii) an indazole ring, optionally substituted with a R² substituent, a R³ substituent or a combination thereof;

wherein each R² or R³ is independently selected from the group consisting of halogen, (C₁-C₈)alkyl, halo(C₁-C₈)alkyl and —OR⁷.

4. A compound of claim 1, wherein Ar¹ is

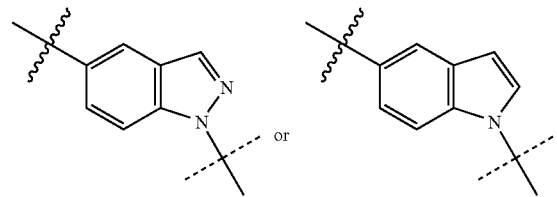

optionally substituted with a R² substituent, a R³ substituent or a combination thereof;

wherein each R² or R³ is independently selected from the group consisting of halogen, (C₁-C₈)alkyl, halo(C₁-C₈)alkyl and —OR⁷; and the dashed line indicates the point of attachment to K and the wavy line indicates the point of attachment to L.

5. A compound of claim 1, wherein Ar¹ is

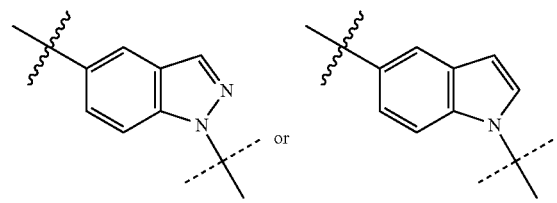

optionally substituted with a R² substituent, a R³ substituent or a combination thereof;

wherein each R² or R³ is independently selected from the group consisting of halogen, (C₁-C₈)alkyl, halo(C₁-C₈)alkyl and —OR⁷; and the dashed line indicates the point of attachment to L and the wavy line indicates the point of attachment to K.

6. A compound of claim 4, wherein Ar¹ is

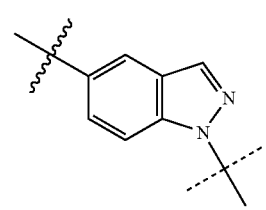

optionally substituted with a R² substituent, a R³ substituent or a combination thereof;

wherein each R² or R³ is independently selected from the group consisting of halogen, (C₁-C₈)alkyl, halo(C₁-C₈)alkyl and —OR⁷; and the dashed line indicates the point of attachment to K and the wavy line indicates the point of attachment to L.

7. A compound of claim 5, wherein Ar$^1$ is

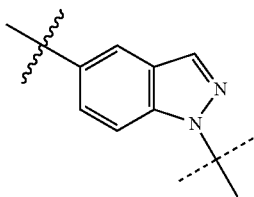

optionally substituted with a R$^2$ substituent, a R$^3$ substituent or a combination thereof;

wherein the dashed line indicates the point of attachment to L and the wavy line indicates the point of attachment to K.

8. A compound of claim 6, wherein the compound is

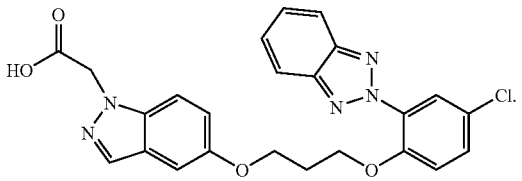

9. A compound of claim 4, wherein Ar$^1$ is

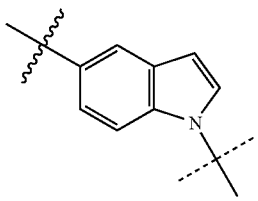

optionally substituted with a R$^2$ substituent, a R$^3$ substituent or a combination thereof;

wherein each R$^2$ or R$^3$ is independently selected from the group consisting of halogen, (C$_1$-C$_8$)alkyl, halo(C$_1$-C$_8$)alkyl and —OR$^7$; and the dashed line indicates the point of attachment to K and the wavy line indicates the point of attachment to L.

10. A compound of claim 5, wherein Ar$^1$ is

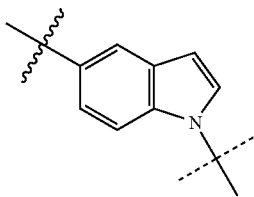

optionally substituted with a R$^2$ substituent, a R$^3$ substituent or a combination thereof;

wherein the dashed line indicates the point of attachment to L and the wavy line indicates the point of attachment to K.

11. A compound of claim 9, wherein the compound is

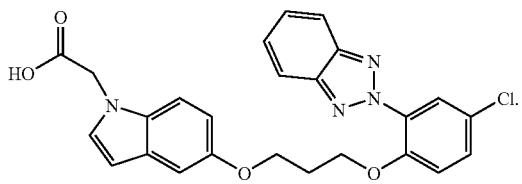

12. A compound of claim 9, wherein the compound is

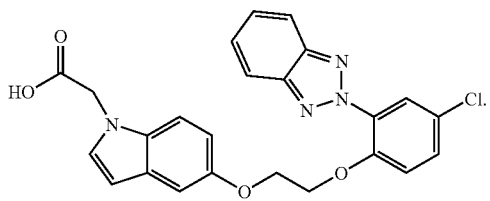

13. A compound of claim 1, wherein Ar$^1$ is benzene, optionally substituted with a R$^2$ substituent, a R$^3$ substituent or a combination thereof;

wherein each R$^2$ or R$^3$ is independently selected from the group consisting of halogen, (C$_1$-C$_8$)alkyl, halo(C$_1$-C$_8$)alkyl, —OR$^7$.

14. A compound of claim 1, wherein Ar$^2$ is benzene, optionally substituted with from one to two R$^4$ substituents;

wherein each R$^4$ substituent is a member independently selected from the group consisting of halogen, (C$_1$-C$_8$)alkyl, halo(C$_1$-C$_8$)alkyl, —OR$^7$,

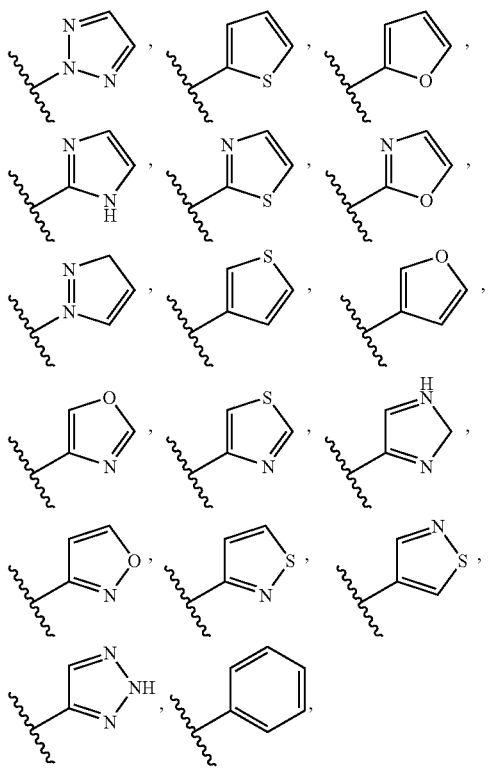

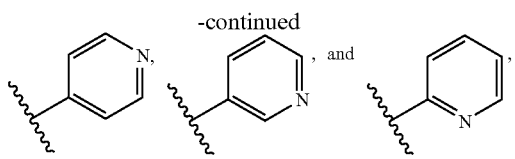

wherein the wavy line indicates the point of attachment to Ar², each ring of which is optionally substituted with from one to two substituents independently selected from the group consisting of halo and (C₁-C₈)alkyl.

15. A compound of claim 14, wherein Ar² has the formula:

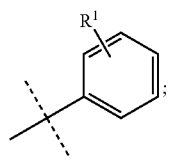

which is optionally substituted with from one to two R⁴ substituents wherein each R⁴ substituent is a member independently selected from the group consisting of halogen, (C₁-C₈)alkyl, halo(C₁-C₈)alkyl, —OR⁷,

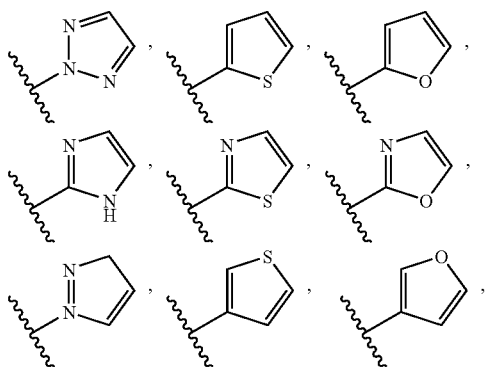

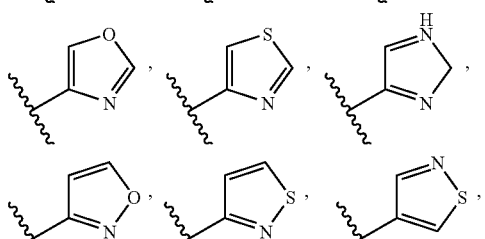

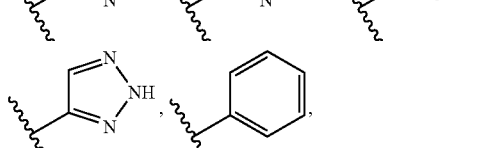

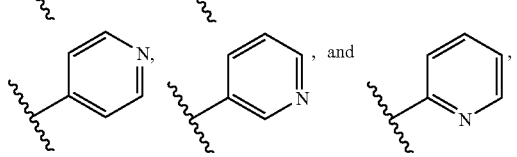

each ring of which is optionally substituted with from one to two substituents independently selected from the group consisting of halo and (C₁-C₈)alkyl; wherein the dashed line indicates the point of 2 attachment to L and the wavy line indicates the point of attachment to Ar².

16. A compound of claim 15, wherein Ar² has the formula:

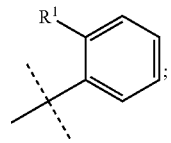

which is optionally substituted with from one to two R⁴ substituents wherein each R⁴ substituent is a member independently selected from the group consisting of halogen, (C₁-C₈)alkyl, halo(C₁-C₈)alkyl, —OR⁷,

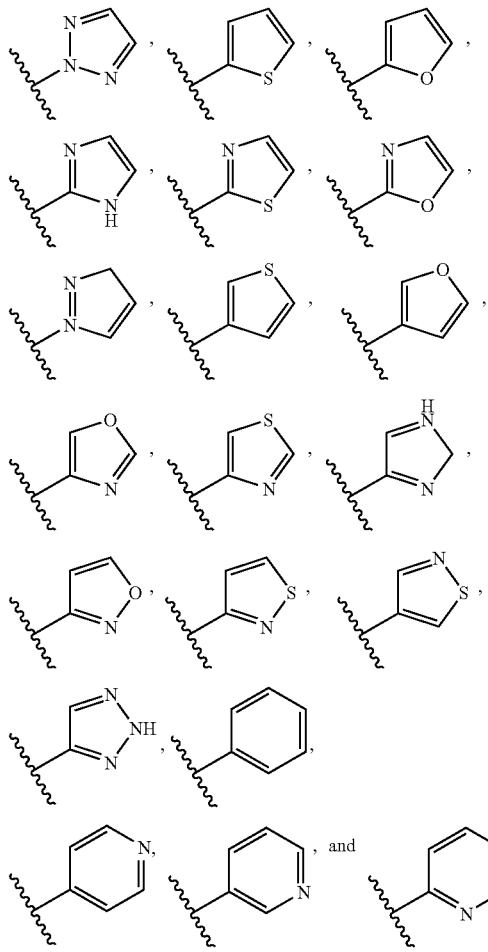

each ring of which is optionally substituted with from one to two substituents independently selected from the group consisting of halo and (C₁-C₈)alkyl; wherein the dashed line indicates the point of attachment to L and the wavy line indicates the point of attachment to Ar².

17. A compound of claim 1, wherein R¹ is a member selected from the group consisting of:

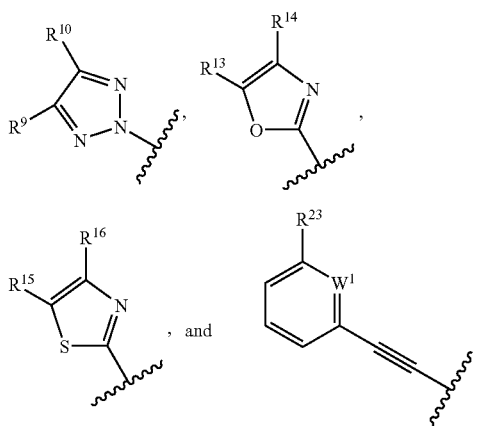

wherein
each $R^9$ or $R^{10}$ is independently $CH_3$, halo or is joined together with the triazole ring to form a triazolopyridine, benzotriazole or tetrahydrobenzotriazole ring optionally substituted with from one to two substituents independently selected from the group consisting of halo and $(C_1-C_8)$alkyl;

each $R^{13}$ or $R^{14}$ is independently $CH_3$, halo or is joined together with the oxazole ring to form a benzoxazolyl ring, optionally substituted with from one to two substituents independently selected from the group consisting of halo and $(C_1-C_8)$alkyl;

each $R^{15}$ or $R^{16}$ is independently H, $(C_1-C_8)$alkyl, halo, $(C_1-C_8)$haloalkyl or is joined together with the thiazole ring to form a benzothiazoyl ring, optionally substituted with from one to two substituents independently selected from the group consisting of —$OR^7$, halo, $(C_1-C_8)$alkyl and $(C_1-C_8)$haloalkyl;

$R^{22}$ is H, $(C_1-C_8)$alkyl, —$OR^7$, halo or $(C_1-C_8)$haloalkyl;

$R^{23}$ is halo or $(C_1-C_9)$alkoxy;

$W^1$ is N or $CR^{22}$; and the wavy line indicates the point of attachment to the rest of the molecule.

18. A compound of claim 17, wherein $R^1$ has the formula:

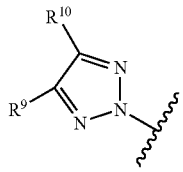

wherein
each $R^9$ or $R^{10}$ is independently $CH_3$, halo or is joined together with the triazole ring to form a triazolopyridine, benzotriazole or tetrahydrobenzotriazole ring optionally substituted with from one to two substituents independently selected from the group consisting of halo and $(C_1-C_8)$alkyl.

19. A compound of claim 17, wherein $R^1$ has the formula:

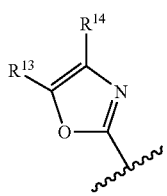

wherein
each $R^{13}$ or $R^{14}$ is independently $CH_3$, halo or is joined together with the oxazole ring to form a benzoxazolyl ring, optionally substituted with from one to two substituents independently selected from the group consisting of halo and $(C_1-C_8)$alkyl.

20. A compound of claim 17, wherein $R^1$ has the formula:

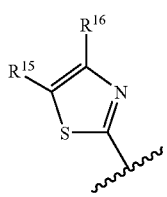

wherein
each $R^{15}$ or $R^{16}$ is independently H, $(C_1-C_8)$alkyl, halo, $(C_1-C_8)$haloalkyl or is joined together with the thiazole ring to form a benzothiazoyl ring, optionally substituted with from one to two substituents independently selected from the group consisting of —$OR^7$, halo, $(C_1-C_8)$alkyl and $(C_1-C_8)$haloalkyl.

21. A compound of claim 17, wherein $R^1$ is a member selected from the group consisting of:

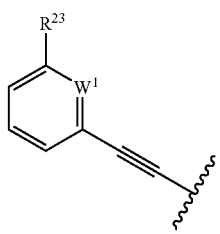

wherein
$R^{22}$ is H, $(C_1-C_8)$alkyl, —$OR^7$, halo or $(C_1-C_8)$haloalkyl;
$R^{23}$ is halo or $(C_1-C_8)$alkoxy; and
$W^1$ is N or $CR^{22}$.

22. A compound of claim 1, wherein the compound is

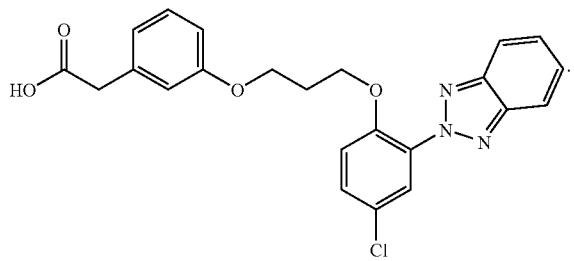

23. A compound of claim 1, wherein the compound is

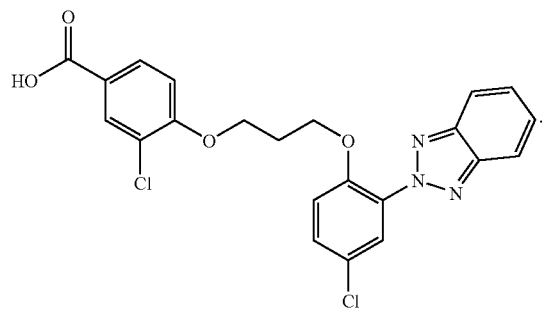

24. A compound of claim 1, wherein $R^1$ has the formula:

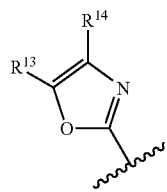

wherein
each $R^{13}$ or $R^{14}$ is $CH_3$, halo or is joined together with the oxazole ring to form a benzoxazolyl ring, optionally substituted with from one to two substituents independently selected from the group consisting of halo and $(C_1$-$C_8)$alkyl.

25. A compound of claim 24, wherein the compound is

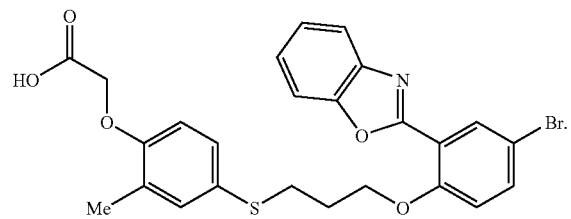

26. A compound of claim 24, wherein the compound is

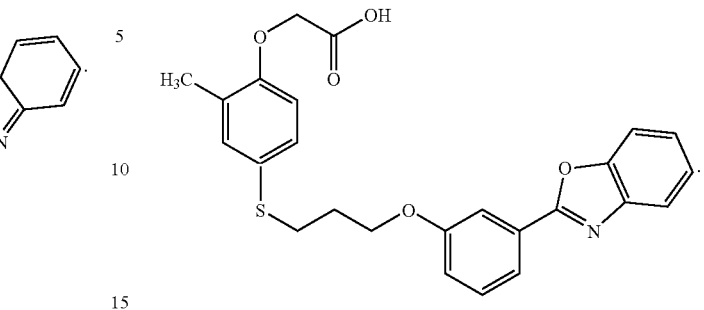

27. A compound of claim 24, wherein the compound is

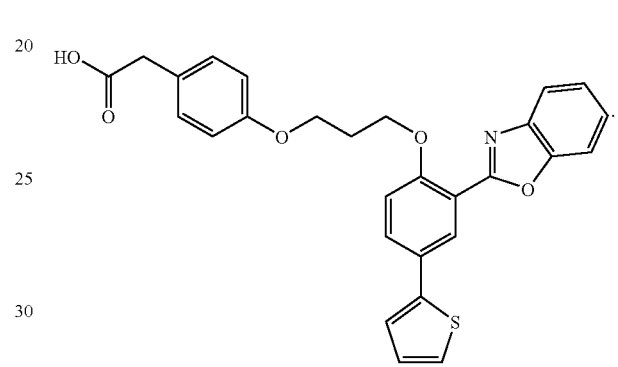

28. A compound of claim 24, wherein the compound is

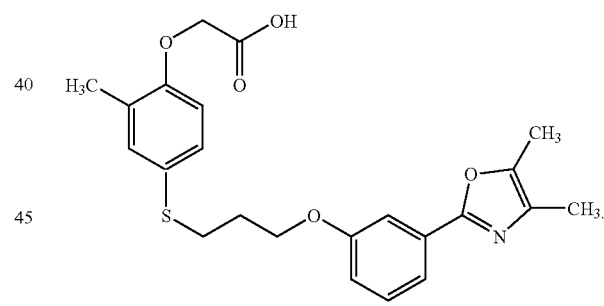

29. A compound of claim 24, wherein the compound is

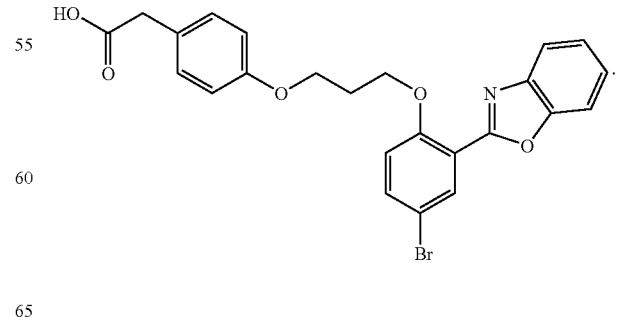

30. A compound of claim 1, wherein R¹ has the formula:

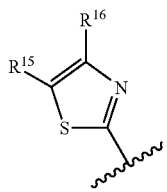

wherein
each $R^{15}$ or $R^{16}$ is independently selected from the group consisting of H, $(C_1-C_8)$alkyl, halo and $(C_1-C_8)$haloalkyl or is joined together with the thiazole ring to form a benzothiazoyl ring, optionally substituted with from one to two substituents independently selected from the group consisting of —$OR^7$, —$CO_2R^7$, —$NR^7R^{24}$, —CN, —$S(O)_{r1}R^7$, halo, $(C_1-C_8)$alkyl and $(C_1-C_8)$haloalkyl.

31. A compound of claim 30, wherein the compound is

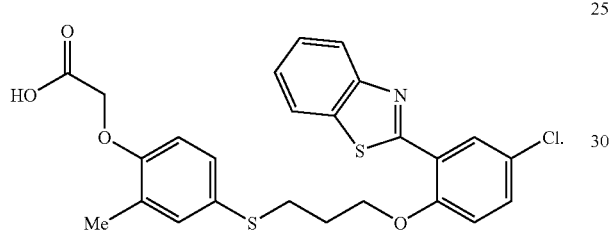

32. A compound of claim 30, wherein the compound is

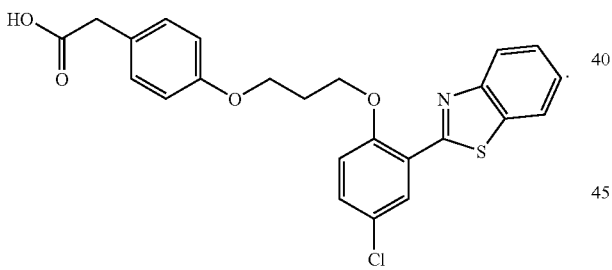

33. A compound of claim 1, wherein R¹ has the formula:

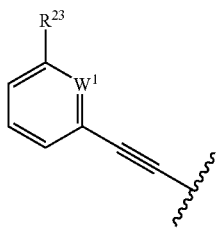

wherein
$R^{22}$ is H, $(C_1-C_8)$alkyl, —$OR^7$, halo or $(C_1-C_8)$haloalkyl;
$R^{23}$ is halo or $(C_1-C_8)$alkoxy; and
$W^1$ is N or $CR^{22}$.

34. A compound of claim 33, wherein the compound is

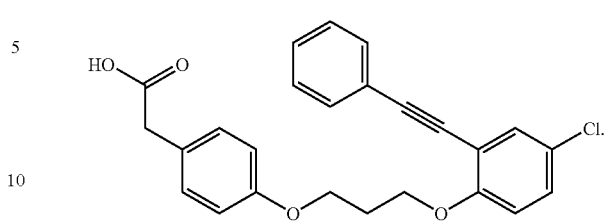

35. A compound of claim 33, wherein the compound is

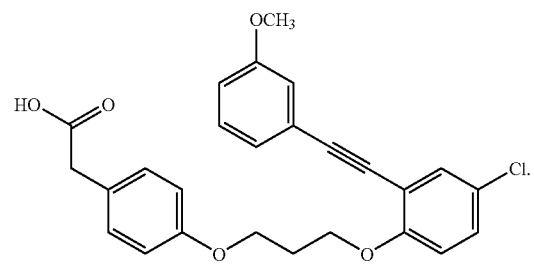

36. A compound of claim 33, wherein the compound is

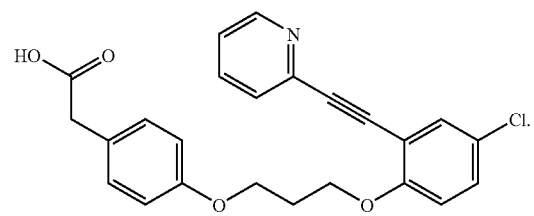

37. A compound of claim 1, wherein R¹ has the formula:

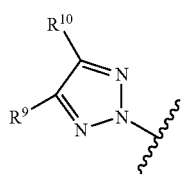

wherein
each $R^9$ or $R^{10}$ is $CH_3$, halo or is joined together with the triazole ring to form a triazolopyridine, benzotriazole or tetrahydrobenzotriazole ring optionally substituted with from one to two substituents independently selected from the group consisting of halo and $(C_1-C_8)$alkyl.

38. A compound of claim 37, wherein the compound is

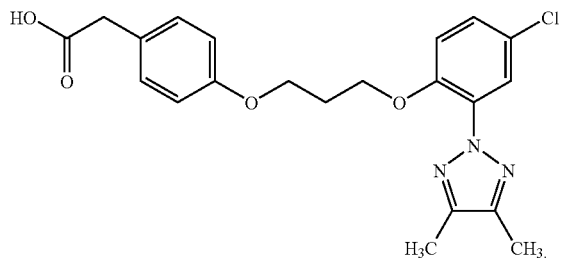

39. A compound of claim 1, wherein the compound is

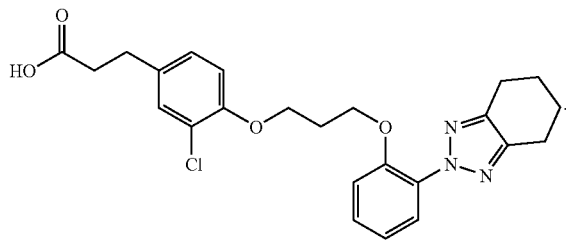

40. A compound of claim 1, wherein the compound is

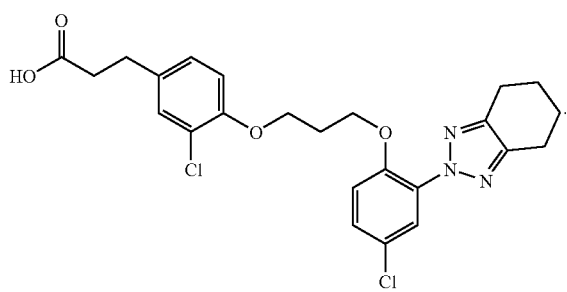

41. A compound of claim 1, wherein the compound is

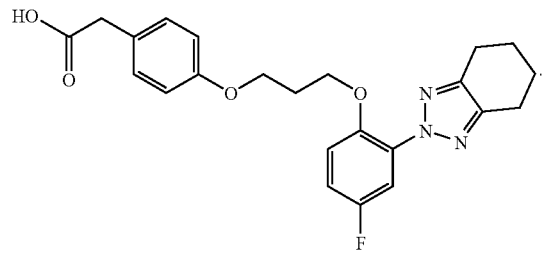

42. A compound of claim 1, wherein the compound is

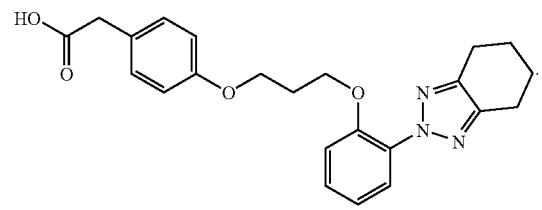

43. A compound of claim 1, wherein the compound is

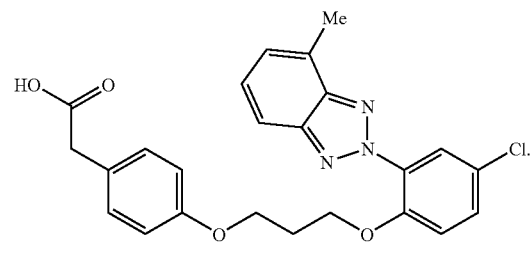

44. A compound of claim 1, wherein the compound is

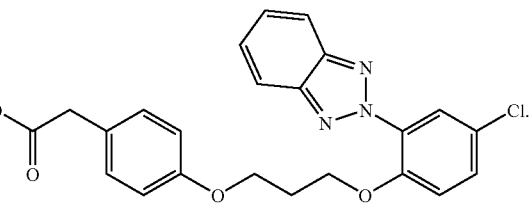

45. A compound of claim 1, wherein the compound is

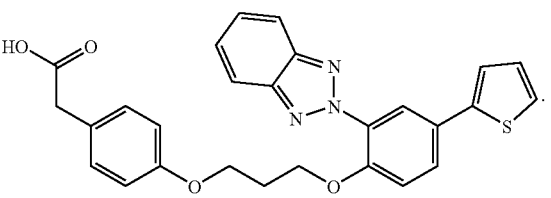

46. A compound of claim 1, wherein the compound is

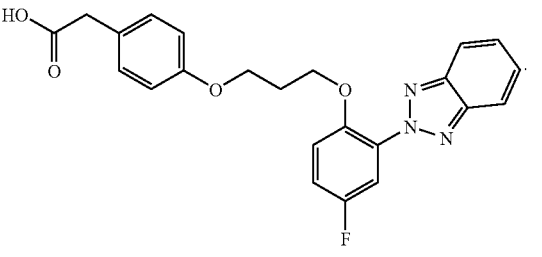

47. A compound of claim 1, wherein the compound is

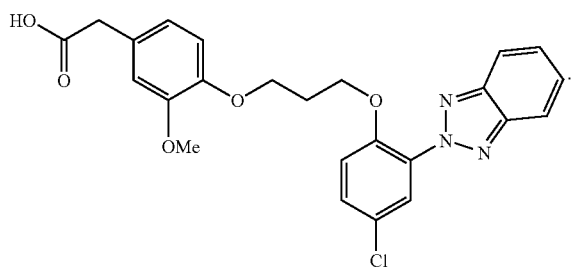

48. A compound of claim 1, wherein the compound is

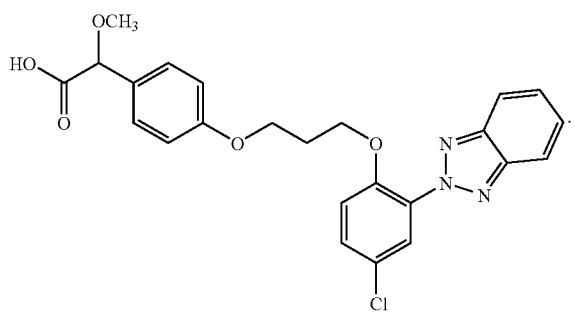

49. A compound of claim 1, wherein the compound is

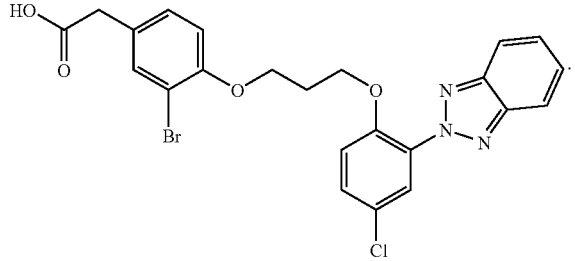

50. A compound of claim 1, wherein the compound is

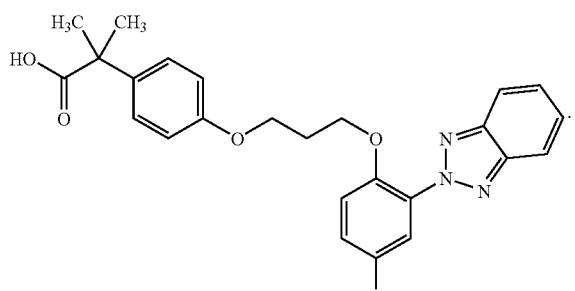

51. A compound of claim 1, wherein the compound is

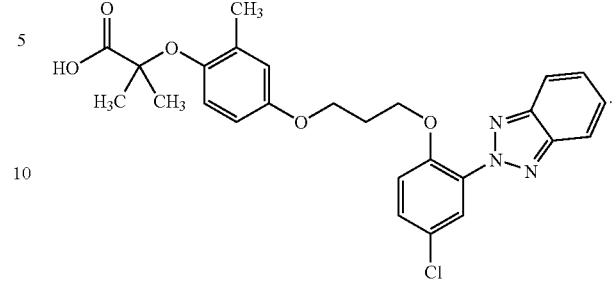

52. A compound of claim 1, wherein the compound is

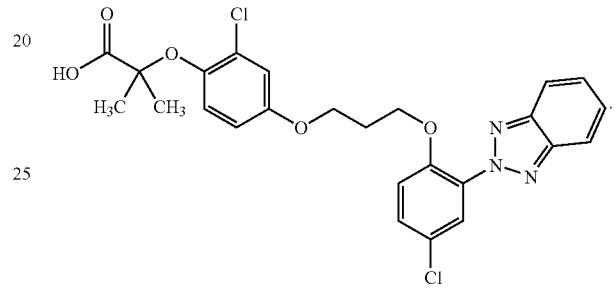

53. A compound of claim 1, wherein the compound is

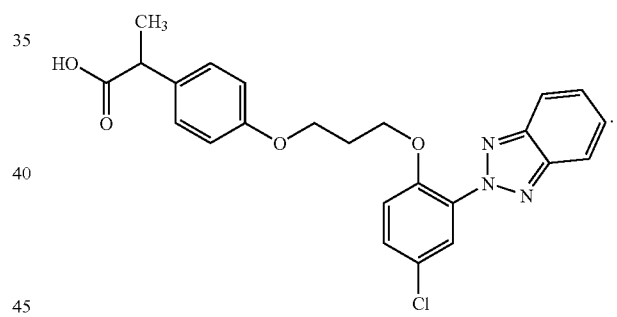

54. A compound of claim 1, wherein the compound is

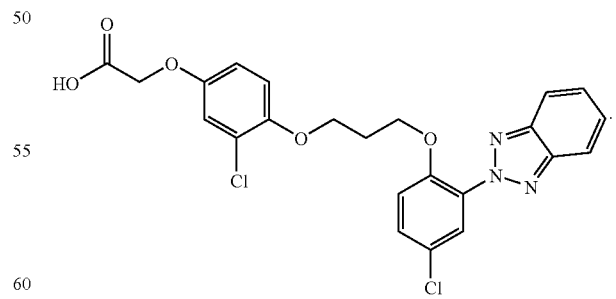

55. A compound selected from the group consisting of:
{4-[3-(2-Benzotriazol-2-yl-4-chloro-phenoxy)-propylsulfanyl]-2-methyl-phenoxy}-acetic acid;
{4-[3-(2-Benzooxazol-2-yl-4-bromo-phenoxy)-propyl-sulfanyl]-2-methyl-phenoxy}-acetic acid;

{4-[2-(2-Benzotriazol-2-yl-4-chloro-phenoxy)-ethylsulfanyl]-2-methyl-phenoxy}-acetic acid;
{4-[3-(2-Benzotriazol-2-yl-4-chloro-phenoxy)-propoxy]-3-propyl-phenyl}-acetic acid;
{4-[3-(2-Benzotriazol-2-yl-4-chloro-phenoxy)-propoxy]-3-chloro-phenyl}-acetic acid;
{4-[2-(2-Benzotriazol-2-yl-4-chloro-phenoxy)-ethoxy]-phenyl}-acetic acid;
{4-[2-(2-Benzotriazol-2-yl-4-chloro-phenoxy)-ethoxy]-3-isopropyl-phenyl}-acetic acid;
(4-{3-[4-Chloro-2-(4,5,6,7-tetrahydro-benzotriazol-2-yl)-phenoxy]-propoxy}-phenyl)-acetic acid;
{4-[3-(4-Chloro-2-phenylethynyl-phenoxy)-propoxy]-phenyl}-acetic acid;
(4-{3-[4-Chloro-2-(3-methoxy-phenylethynyl)-phenoxy]-propoxy}-phenyl)-acetic acid;
{4-[3-(4-Chloro-2-pyridin-2-ylethynyl-phenoxy)-propoxy]-phenyl}-acetic acid;
(4-{3-[4-Chloro-2-(4-methyl-benzotriazol-2-yl)-phenoxy]-propoxy}-phenyl)-acetic acid;
{5-[3-(2-Benzotriazol-2-yl-4-chloro-phenoxy)-propoxy]-indazol-1-yl}-acetic acid;
{5-[3-(2-Benzotriazol-2-yl-4-chloro-phenoxy)-propoxy]-indol-1-yl}-acetic acid;
{5-[2-(2-Benzotriazol-2-yl-4-chloro-phenoxy)-ethoxy]-indol-1-yl}-acetic acid;
{5-[3-(3-Benzooxazol-2-yl-phenoxy)-propoxy]-indol-1-yl}-acetic acid;
{4-[3-(3-Benzooxazol-2-yl-phenoxy)-propylsulfanyl]-2-methyl-phenoxy}-acetic acid;
(4-{3-[3-(4,5-Dimethyl-oxazol-2-yl)-phenoxy]-propylsulfanyl}-2-methyl-phenoxy)-acetic acid;
{1-[3-(2-Benzotriazol-2-yl-4-chloro-phenoxy)-propyl]-1H-indol-5-yloxy}-acetic acid;
4-[3-(2-Benzotriazol-2-yl-4-chloro-phenoxy)-propoxy]-3-chloro-benzoic acid;
{4-[3-(2-Benzotriazol-2-yl-4-chloro-phenoxy)-propoxy]-3-chloro-phenoxy}-acetic acid;
3-(3-Chloro-4-{3-[2-(4,5,6,7-tetrahydro-benzotriazol-2-yl)-phenoxy]-propoxy}-phenyl)-propionic acid;
3-(3-Chloro-4-{3-[4-chloro-2-(4,5,6,7-tetrahydro-benzotriazol-2-yl)-phenoxy]-propoxy}-phenyl)-propionic acid;
{4-[3-(2-Benzotriazol-2-yl-4-chloro-phenoxy)-propoxy]-phenoxy}-acetic acid;
{4-[3-(2-Benzotriazol-2-yl-4-thiophen-2-yl-phenoxy)-propoxy]-phenyl}-acetic acid;
[5-(2-Benzotriazol-2-yl-4-chloro-phenoxymethyl)-indol-1-yl]-acetic acid;
{4-[3-(2-Benzotriazol-2-yl-4-methoxy-phenoxy)-propoxy]-phenyl}-acetic acid;
(4-{3-[4-Chloro-2-(4-methyl-benzotriazol-2-yl)-phenoxy]-propoxy}-phenyl)-acetic acid ethyl ester;
{4-[3-(4-Chloro-2-phenylethynyl-phenoxy)-propoxy]-phenyl}-acetic acid ethyl ester;
(4-{3-[4-Chloro-2-(4,5,6,7-tetrahydro-benzotriazol-2-yl)-phenoxy]-propoxy}-phenyl)-acetic acid ethyl ester;
{4-[2-(2-Benzotriazol-2-yl-4-thiophen-2-yl-phenoxy)-ethoxy]-3-propyl-phenyl}-acetic acid ethyl ester;
{4-[3-(2-Benzotriazol-2-yl-4-chloro-phenoxy)-propoxy]-phenyl}-acetic acid methyl ester;
{4-[3-(2-Benzotriazol-2-yl-4-chloro-phenoxy)-propoxy]-phenyl}-acetic acid;
{4-[3-(2-Benzotriazol-2-yl-4-chloro-phenoxy)-propylsulfanyl]-2-methyl-phenoxy}-acetic acid ethyl ester;
{4-[3-(3-Benzooxazol-2-yl-phenoxy)-propylsulfanyl]-2-methyl-phenoxy}-acetic acid;
(4-{3-[3-(4,5-Dimethyl-oxazol-2-yl)-phenoxy]-propylsulfanyl}-2-methyl-phenoxy)-acetic acid;
(4-{3-[4-Chloro-2-(4,5-dimethyl-[1,2,3]triazol-2-yl)-phenoxy]-propoxy}-phenyl)-acetic acid;
{4-[3-(2-Benzooxazol-2-yl-4-bromo-phenoxy)-propoxy]-phenyl}-acetic acid;
{4-[3-(2-Benzotriazol-2-yl-4-fluoro-phenoxy)-propoxy]-phenyl}-acetic acid;
{4-[3-(2-Benzothiazol-2-yl-4-chloro-phenoxy)-propoxy]-phenyl}-acetic acid;
{4-[3-(2-Benzotriazol-2-yl-4-chloro-phenoxy)-propoxy]-3-methoxy-phenyl}-acetic acid;
{4-[3-(2-Benzotriazol-2-yl-4-chloro-phenoxy)-propoxy]-phenyl}-methoxy-acetic acid;
{4-[3-(2-Benzotriazol-2-yl-4-chloro-phenoxy)-propoxy]-3-Bromo-phenyl}-acetic acid;
{3-[3-(2-Benzotriazol-2-yl-4-chloro-phenoxy)-propoxy]-phenyl}-acetic acid;
2-{4-[3-(2-Benzotriazol-2-yl-4-chloro-phenoxy)-propoxy]-phenyl}-2-methyl-propionic acid;
2-{4-[3-(2-Benzotriazol-2-yl-4-chloro-phenoxy)-propoxy]-2-methyl-phenoxy}-2-methyl-propionic acid;
2-{4-[3-(2-Benzotriazol-2-yl-4-chloro-phenoxy)-propoxy]-2-chloro-phenoxy}-2-methyl-propionic acid;
2-{4-[3-(2-Benzotriazol-2-yl-4-chloro-phenoxy)-propoxy]-phenyl}-propionic acid;
{4-[3-(2-Benzooxazol-2-yl-4-thiophen-2-yl-phenoxy)-propoxy]-phenyl}-acetic acid;
(4-{3-[4-Fluoro-2-(4,5,6,7-tetrahydro-benzotriazol-2-yl)-phenoxy]-propoxy}-phenyl)-acetic acid;
(4-{3-[2-(4,5,6,7-Tetrahydro-benzotriazol-2-yl)-phenoxy]-propoxy}-phenyl)-acetic acid;
4-[3-(2-Benzotriazol-2-yl-4-chloro-phenoxy)-propoxy]-3-chloro-benzoic acid;
{4-[3-(2-Benzotriazol-2-yl-4-chloro-phenoxy)-propoxy]-3-chloro-phenoxy}-acetic acid;
3-(3-Chloro-4-{3-[2-(4,5,6,7-tetrahydro-benzotriazol-2-yl)-phenoxy]-propoxy}-phenyl)-propionic acid; and
3-(3-Chloro-4-{3-[4-chloro-2-(4,5,6,7-tetrahydro-benzotriazol-2-yl)-phenoxy]-propoxy}-phenyl)-propionic acid.

56. A compound selected from the group consisting of:
{4-[3-(2-Benzotriazol-2-yl-4-chloro-phenoxy)-propoxy]-phenyl}-acetic acid and {4-[3-(2-benzotriazol-2-yl-4-thiophen-2-yl-phenoxy)-propoxy]-phenyl}-acetic acid.

57. A composition comprising one or more pharmaceutically acceptable carriers, diluents or excipients and a compound of claim 1.

* * * * *

UNITED STATES PATENT AND TRADEMARK OFFICE
CERTIFICATE OF CORRECTION

PATENT NO.       : 7,622,491 B2                                                    Page 1 of 1
APPLICATION NO.  : 11/202963
DATED            : November 24, 2009
INVENTOR(S)      : Zhu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 751 days.

Signed and Sealed this

Twenty-sixth Day of October, 2010

David J. Kappos
*Director of the United States Patent and Trademark Office*